(12) United States Patent
Hiraoka et al.

(10) Patent No.: US 7,700,754 B1
(45) Date of Patent: Apr. 20, 2010

(54) POLYPEPTIDE FOR UNSTABILIZING PROTEIN IN CELLS UNDER AEROBIC CONDITIONS AND DNA ENCODING THE SAME

(75) Inventors: Masahiro Hiraoka, 33, Iwakura, Minamiyonnotsubo-cho, Sakyo-ku, Kyoto-shi, Kyoto 606-0033 (JP); Shinae Kondoh, 18, Okazaki, Kitagosho-machi, Sakyo-ku, Kyoto-shi, Kyoto 606-8336 (JP); Hiroshi Harada, Yokohama (JP)

(73) Assignees: Masahiro Hiraoka, Kyoto (JP); Shinae Kondoh, Kyoto (JP)

( * ) Notice: Subject to any disclaimer, the term of this patent is extended or adjusted under 35 U.S.C. 154(b) by 1832 days.

(21) Appl. No.: 10/479,700

(22) PCT Filed: Jun. 4, 2002

(86) PCT No.: PCT/JP02/05482

§ 371 (c)(1),
(2), (4) Date: Dec. 5, 2003

(87) PCT Pub. No.: WO02/099104

PCT Pub. Date: Dec. 12, 2002

(30) Foreign Application Priority Data

Jun. 5, 2001 (JP) ............................. 2001-169948
Jun. 5, 2001 (JP) ............................. 2001-169949

(51) Int. Cl.
*C07H 21/04* (2006.01)
*C07H 21/02* (2006.01)
*C07K 14/00* (2006.01)

(52) U.S. Cl. .................. 536/23.7; 536/23.1; 536/24.32; 530/300; 530/350

(58) Field of Classification Search ................ 536/23.1, 536/23.7, 24.32; 530/300, 350
See application file for complete search history.

(56) References Cited

U.S. PATENT DOCUMENTS 5,804,604 A  9/1998  Frankel et al.
5,882,914 A *  3/1999  Semenza .................. 435/252.3

FOREIGN PATENT DOCUMENTS

WO  WO 94/04686  2/1994
WO  WO 99/10376  3/1999
WO  WO 00/69908  11/2000
WO  WO 01/19393 A1  3/2001

OTHER PUBLICATIONS

Ema et al., "Molecular mechanisms of transcription activation by HLF and HIFα in response to hypoxia: their stabilization and redox signal-induced interaction with CBP/p300" *The EMBO Journal* 18(7):1905-1914 (1999).

Harada et al., "Antitumor Effect of TAT-Oxygen-dependent Degradation-Caspase-3 Fusion Protein Specifically Stabilized and Activated in Hypoxic Tumor Cells" *Cancer Research* 62:2013-1018 (Apr. 1, 2002).

Huang et al., "Regulation of hypoxia-inducible factor 1α is mediated by an $O_2$-dependent degradation domain via the ubiquitin-proteasome pathway" *Proc. Natl. Acad. Sci.* USA 95:7987-7992 (Jul. 1998).

Li et al., "Induction of Phosphoglycerate Kinase 1 Gene Expression by Hypoxia" *The Journal of Biological Chemistry* 271(35):21262-21267 (Aug. 30, 1996).

Pugh et al., "Activation of Hypoxia-inducible Factor-1; Definition of Regulatory Domains within the α Subunit" *The Journal of Biological Chemistry* 272(17):11205-11214 (Apr. 25, 1997).

Jiang et al. "Transactivation and Inhibitory Domains of Hypoxia-inducible Factor 1α", *The Journal of Biological Chemistry*, Aug. 1, 1997, pp. 19253-19260, vol. 272, No. 31.

O'Rourke et al. "Oxygen-regulated and Transactivating Domains in Endothelial PAS Protein 1: Comparison with Hypoxia-inducible Factor-1α", *The Journal of Biological Chemistry*, Jan. 22, 1999, pp. 2060-2071, vol. 274, No. 4.

"Human hypoxia-inducible factor 1 alpha (HIF-1 alpha)mRNA, complete cds" Database EMBL Accession No. U22431, Mar. 4, 2000.

* cited by examiner

*Primary Examiner*—Rodney P. Swartz
(74) *Attorney, Agent, or Firm*—Knobbe Martens Olson & Bear LLP

(57) ABSTRACT

To identify a domain in HIF-1α protein, which participates in stabilization of a fused protein, DNA encoding the following polypeptide (A) or (B) is provided:
(A) a polypeptide having the amino acid sequence of SEQ ID NO: 1
(B) a polypeptide having an amino acid sequence comprising at least 16 amino acid residues in the amino acid sequence of SEQ ID NO: 1, and imparting stability dependent on an oxygen concentration to other protein in a cell harboring a fused protein, when the polypeptide is fused with a nuclear localization signal and the other protein to form the fused protein.

47 Claims, 9 Drawing Sheets

A) HEK293 / pCH110 (-Cbz-LLL)

B) HEK293 / pCH110 (+Cbz-LLL)

C) HEK293 / pCH/3-0 (-Cbz-LLL)

D) HEK293 / pCH3-0 (+Cbz-LLL)

A) P.C. β-gal/(-Cbz-LLL)

B) P.C. β-gal/(+Cbz-LLL)

C) 3-0 β-gal/(-Cbz-LLL)

D) 3-0 β-gal/(+Cbz-LLL)

Well No. 1      Well No. 2      Well No. 3

Well No. 4      Well No. 5      Well No. 6

SEQUENCE LISTING

<160> NUMBER OF SEQ ID NOS: 55

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: polypeptide encoded by synthetic DNA

<400> SEQUENCE: 1

Leu Asp Leu Glu Met Leu Ala Pro Tyr Ile Pro Met Asp Asp Asp Phe
 1               5                  10                  15

Gln Leu

<210> SEQ ID NO 2
<211> LENGTH: 54
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 2
ttagacttgg agatgttagc tccctatatc ccaatggatg atgacttcca gtta         54

<210> SEQ ID NO 3
<211> LENGTH: 168
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 3
aacccatttt ctactcagga cacagattta gacttggaga tgttagctcc ctatatccca    60
atggatgatg acttccagtt acgttccttc gatcagttgt caccattaga aagcagttcc   120
gcaagccctg aaagcgcaag tcctcaaagc acagttacag tattccag               168

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: polipeptide
      encoded by synthetic DNA

<400> SEQUENCE: 4

Tyr Gly Arg Lys Lys Arg Arg Gln Arg Arg Arg
 1               5                  10

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 5
tatggtcgta agaaacgtcg ccaacgtcgc cga                                 33

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 6
atggcgccta agaagaagag gaag                                           24

<210> SEQ ID NO 7
<211> LENGTH: 41
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 7
taagcttgac atggcgccta agaagaagag gaagagatct g                           41

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 8
cagatctctt cctcttcttc ttaggcgcca tgtcaagctt a                           41

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 9
gagatctgcc ccagccgctg gagacacaa                                         29

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 10
ggagatcttt ggcaatgtct ccattaccca cc                                     32

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 11
ggagatctcc tagtccttcc gatggaagca ct                                     32

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 12
ggagatctaa cccattttct actcaggaca ca                                     32

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: synthetic
       DNA

<400> SEQUENCE: 13
ggagatctca gttgtcacca ttagaaagca gt                                    32

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: synthetic
       DNA

<400> SEQUENCE: 14
aggtacctgc tggaatactg taactgtgc                                        29

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: synthetic
       DNA

<400> SEQUENCE: 15
aaggtacctg atttatattc tgtaattttt cgtt                                  34

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: synthetic
       DNA

<400> SEQUENCE: 16
aaggtacctg tgtctgatcc tgaatctggg gcat                                  34

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: synthetic
       DNA

<400> SEQUENCE: 17
aaggtacctg ctttgcttct gtgtcttcag caaa                                  34

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: synthetic
       DNA

<400> SEQUENCE: 18
aaggtacctg taatggtgac aactgatcga agga                                  34

<210> SEQ ID NO 19

```
<211> LENGTH: 66
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 19
gatctttaga cttggagatg ttagctccct atatcccaat ggatgatgac ttccagttac     60
aggtac                                                                66

<210> SEQ ID NO 20
<211> LENGTH: 58
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 20
ctgtaactgg aagtcatcat ccattgggat atagggagct aacatctcca agtct aaa      58

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 21
gatctttagc tccctatatc ccaatggatc aggtac                               36

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 22
ctgatccatt gggatatagg gagctaaa                                        28

<210> SEQ ID NO 23
<211> LENGTH: 57
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 23
gatctttaga cttggagatg ttagctccct atatcccaat ggatgatgac caggtac        57

<210> SEQ ID NO 24
<211> LENGTH: 49
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 24
ctggtcatca tccattggga tagggagc taacatctcc aagtctaaa                   49
```

```
<210> SEQ ID NO 25
<211> LENGTH: 57
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 25
gatctgagat gttagctccc tatatcccaa tggatgatga cttccagtta caggtac        57

<210> SEQ ID NO 26
<211> LENGTH: 49
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 26
ctgtaactgg aagtcatcat ccattgggat atagggagct aacatctca                 49

<210> SEQ ID NO 27
<211> LENGTH: 66
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 27
gatctttaga cttggagatg ttagctcccg ctatcccaat ggatgatgac ttccagttac     60
aggtac                                                                66

<210> SEQ ID NO 28
<211> LENGTH: 58
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 28
ctgtaactgg aagtcatcat ccattgggat agcgggagct aacatctcca agtctaaa      58

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: polipeptide
      encoded by synthetic DNA

<400> SEQUENCE: 29

Leu Ala Pro Tyr Ile Pro Met Asp
  1               5

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 30
agcttgacat ggcga                                                      15
```

```
<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 31
gatctcgcca tgtca                                                        15

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 32
gatcatatgg tcgtaagaaa cgtcgccaac gtcgccgaa                              39

<210> SEQ ID NO 33
<211> LENGTH: 39
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 33
gatcttcggc gacgttggcg acgtttctta cgaccatat                              39

<210> SEQ ID NO 34
<211> LENGTH: 39
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 34
agcttgacat ggcgcctaag aagaagagga agcaggtac                              39

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 35
ctgcttcctc ttcttcttag gcgccatgtc a                                      31

<210> SEQ ID NO 36
<211> LENGTH: 42
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 36
gatatggtcg taagaaacgt cgccaacgtc gccgacaggt ac                          42
```

<210> SEQ ID NO 37
<211> LENGTH: 42
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 37
ctgtcggcga cgttggcgac gtttcttacg accatatcgt ac                          42

<210> SEQ ID NO 38
<211> LENGTH: 7173
<212> TYPE: DNA
<213> ORGANISM: Artificial Sequence
<220> FEATURE:
<223> OTHER INFORMATION: Description of Artificial Sequence: synthetic
      DNA
<220> FEATURE:
<221> NAME/KEY: CDS
<222> LOCATION: (10)..(3384)
<220> FEATURE:
<223> OTHER INFORMATION: Description of Artificial Sequence: fusion gene
      of 00 and 11

<400> SEQUENCE: 38 aagcttgac atg gcg cct aag aag aag agg aag aga tca tat ggt cgt aag        51
           Met Ala Pro Lys Lys Lys Arg Lys Arg Ser Tyr Gly Arg Lys
             1               5                  10 aaa cgt cgc caa cgt cgc cga aga tct aac cca ttt tct act cag gac          99
Lys Arg Arg Gln Arg Arg Arg Arg Ser Asn Pro Phe Ser Thr Gln Asp
 15                  20                  25                  30 aca gat tta gac ttg gag atg tta gct ccc tat atc cca atg gat gat         147
Thr Asp Leu Asp Leu Glu Met Leu Ala Pro Tyr Ile Pro Met Asp Asp
                 35                  40                  45 gac ttc cag tta cgt tcc ttc gat cag ttg tca cca tta gaa agc agt         195
Asp Phe Gln Leu Arg Ser Phe Asp Gln Leu Ser Pro Leu Glu Ser Ser
             50                  55                  60 tcc gca agc cct gaa agc gca agt cct caa agc aca gtt aca gta ttc         243
Ser Ala Ser Pro Glu Ser Ala Ser Pro Gln Ser Thr Val Thr Val Phe
         65                  70                  75 cag cag gta ccg gtg ggt gaa gac cag aaa cag cac ctc gaa ctg agc         291
Gln Gln Val Pro Val Gly Glu Asp Gln Lys Gln His Leu Glu Leu Ser
     80                  85                  90 cgc gat att gcc cag cgt ttc aac gcg ctg tat ggc gag atc gat ccc         339
Arg Asp Ile Ala Gln Arg Phe Asn Ala Leu Tyr Gly Glu Ile Asp Pro
 95                 100                 105                 110 gtc gtt tta caa cgt cgt gac tgg gaa aac cct ggc gtt acc caa ctt         387
Val Val Leu Gln Arg Arg Asp Trp Glu Asn Pro Gly Val Thr Gln Leu
                115                 120                 125 aat cgc ctt gca gca cat ccc cct ttc gcc agc tgg cgt aat agc gaa         435
Asn Arg Leu Ala Ala His Pro Pro Phe Ala Ser Trp Arg Asn Ser Glu
            130                 135                 140 gag gcc cgc acc gat cgc cct tcc caa cag ttg cgc agc ctg aat ggc         483
Glu Ala Arg Thr Asp Arg Pro Ser Gln Gln Leu Arg Ser Leu Asn Gly
        145                 150                 155 gaa tgg cgc ttt gcc tgg ttt ccg gca cca gaa gcg gtg ccg gaa agc         531
Glu Trp Arg Phe Ala Trp Phe Pro Ala Pro Glu Ala Val Pro Glu Ser
    160                 165                 170 tgg ctg gag tgc gat ctt cct gag gcc gat act gtc gtc gtc ccc tca         579
Trp Leu Glu Cys Asp Leu Pro Glu Ala Asp Thr Val Val Val Pro Ser
175                 180                 185                 190 aac tgg cag atg cac ggt tac gat gcg ccc atc tac acc aac gta acc         627

```
                Asn Trp Gln Met His Gly Tyr Asp Ala Pro Ile Tyr Thr Asn Val Thr
                            195                 200                 205 tat ccc att acg gtc aat ccg ccg ttt gtt ccc acg gag aat ccg acg        675
Tyr Pro Ile Thr Val Asn Pro Pro Phe Val Pro Thr Glu Asn Pro Thr
            210                 215                 220 ggt tgt tac tcg ctc aca ttt aat gtt gat gaa agc tgg cta cag gaa        723
Gly Cys Tyr Ser Leu Thr Phe Asn Val Asp Glu Ser Trp Leu Gln Glu
        225                 230                 235 ggc cag acg cga att att ttt gat ggc gtt aac tcg gcg ttt cat ctg        771
Gly Gln Thr Arg Ile Ile Phe Asp Gly Val Asn Ser Ala Phe His Leu
    240                 245                 250 tgg tgc aac ggg cgc tgg gtc ggt tac ggc cag gac agt cgt ttg ccg        819
Trp Cys Asn Gly Arg Trp Val Gly Tyr Gly Gln Asp Ser Arg Leu Pro
255                 260                 265                 270 tct gaa ttt gac ctg agc gca ttt tta cgc gcc gga gaa aac cgc ctc        867
Ser Glu Phe Asp Leu Ser Ala Phe Leu Arg Ala Gly Glu Asn Arg Leu
                275                 280                 285 gcg gtg atg gtg ctg cgt tgg agt gac ggc agt tat ctg gaa gat cag        915
Ala Val Met Val Leu Arg Trp Ser Asp Gly Ser Tyr Leu Glu Asp Gln
            290                 295                 300 gat atg tgg cgg atg agc ggc att ttc cgt gac gtc tcg ttg ctg cat        963
Asp Met Trp Arg Met Ser Gly Ile Phe Arg Asp Val Ser Leu Leu His
        305                 310                 315 aaa ccg act aca caa atc agc gat ttc cat gtt gcc act cgc ttt aat       1011
Lys Pro Thr Thr Gln Ile Ser Asp Phe His Val Ala Thr Arg Phe Asn
    320                 325                 330 gat gat ttc agc cgc gct gta ctg gag gct gaa gtt cag atg tgc ggc       1059
Asp Asp Phe Ser Arg Ala Val Leu Glu Ala Glu Val Gln Met Cys Gly
335                 340                 345                 350 gag ttg cgt gac tac cta cgg gta aca gtt tct tta tgg cag ggt gaa       1107
Glu Leu Arg Asp Tyr Leu Arg Val Thr Val Ser Leu Trp Gln Gly Glu
                355                 360                 365 acg cag gtc gcc agc ggc acc gcg cct ttc ggc ggt gaa att atc gat       1155
Thr Gln Val Ala Ser Gly Thr Ala Pro Phe Gly Gly Glu Ile Ile Asp
            370                 375                 380 gag cgt ggt ggt tat gcc gat cgc gtc aca cta cgt ctg aac gtc gaa       1203
Glu Arg Gly Gly Tyr Ala Asp Arg Val Thr Leu Arg Leu Asn Val Glu
        385                 390                 395 aac ccg aaa ctg tgg agc gcc gaa atc ccg aat ctc tat cgt gcg gtg       1251
Asn Pro Lys Leu Trp Ser Ala Glu Ile Pro Asn Leu Tyr Arg Ala Val
    400                 405                 410 gtt gaa ctg cac acc gcc gac ggc acg ctg att gaa gca gaa gcc tgc       1299
Val Glu Leu His Thr Ala Asp Gly Thr Leu Ile Glu Ala Glu Ala Cys
415                 420                 425                 430 gat gtc ggt ttc cgc gag gtg cgg att gaa aat ggt ctg ctg ctg ctg       1347
Asp Val Gly Phe Arg Glu Val Arg Ile Glu Asn Gly Leu Leu Leu Leu
                435                 440                 445 aac ggc aag ccg ttg ctg att cga ggc gtt aac cgt cac gag cat cat       1395
Asn Gly Lys Pro Leu Leu Ile Arg Gly Val Asn Arg His Glu His His
            450                 455                 460 cct ctg cat ggt cag gtc atg gat gag cag acg atg gtg cag gat atc       1443
Pro Leu His Gly Gln Val Met Asp Glu Gln Thr Met Val Gln Asp Ile
        465                 470                 475 ctg ctg atg aag cag aac aac ttt aac gcc gtg cgc tgt tcg cat tat       1491
Leu Leu Met Lys Gln Asn Asn Phe Asn Ala Val Arg Cys Ser His Tyr
    480                 485                 490 ccg aac cat ccg ctg tgg tac acg ctg tgc gac cgc tac ggc ctg tat       1539
Pro Asn His Pro Leu Trp Tyr Thr Leu Cys Asp Arg Tyr Gly Leu Tyr
495                 500                 505                 510
```

```
gtg gtg gat gaa gcc aat att gaa acc cac ggc atg gtg cca atg aat        1587
Val Val Asp Glu Ala Asn Ile Glu Thr His Gly Met Val Pro Met Asn
            515                 520                 525 cgt ctg acc gat gat ccg cgc tgg cta ccg gcg atg agc gaa cgc gta        1635
Arg Leu Thr Asp Asp Pro Arg Trp Leu Pro Ala Met Ser Glu Arg Val
        530                 535                 540 acg cga atg gtg cag cgc gat cgt aat cac ccg agt gtg atc atc tgg        1683
Thr Arg Met Val Gln Arg Asp Arg Asn His Pro Ser Val Ile Ile Trp
    545                 550                 555 tcg ctg ggg aat gaa tca ggc cac ggc gct aat cac gac gcg ctg tat        1731
Ser Leu Gly Asn Glu Ser Gly His Gly Ala Asn His Asp Ala Leu Tyr
560                 565                 570 cgc tgg atc aaa tct gtc gat cct tcc cgc ccg gtg cag tat gaa ggc        1779
Arg Trp Ile Lys Ser Val Asp Pro Ser Arg Pro Val Gln Tyr Glu Gly
575                 580                 585                 590 ggc gga gcc gac acc acg gcc acc gat att att tgc ccg atg tac gcg        1827
Gly Gly Ala Asp Thr Thr Ala Thr Asp Ile Ile Cys Pro Met Tyr Ala
                595                 600                 605 cgc gtg gat gaa gac cag ccc ttc ccg gct gtg ccg aaa tgg tcc atc        1875
Arg Val Asp Glu Asp Gln Pro Phe Pro Ala Val Pro Lys Trp Ser Ile
            610                 615                 620 aaa aaa tgg ctt tcg cta cct gga gag acg cgc ccg ctg atc ctt tgc        1923
Lys Lys Trp Leu Ser Leu Pro Gly Glu Thr Arg Pro Leu Ile Leu Cys
        625                 630                 635 gaa tac gcc cac gcg atg ggt aac agt ctt ggc ggt ttc gct aaa tac        1971
Glu Tyr Ala His Ala Met Gly Asn Ser Leu Gly Gly Phe Ala Lys Tyr
    640                 645                 650 tgg cag gcg ttt cgt cag tat ccc cgt tta cag ggc ggc ttc gtc tgg        2019
Trp Gln Ala Phe Arg Gln Tyr Pro Arg Leu Gln Gly Gly Phe Val Trp
655                 660                 665                 670 gac tgg gtg gat cag tcg ctg att aaa tat gat gaa aac ggc aac ccg        2067
Asp Trp Val Asp Gln Ser Leu Ile Lys Tyr Asp Glu Asn Gly Asn Pro
                675                 680                 685 tgg tcg gct tac ggc ggt gat ttt ggc gat acg ccg aac gat cgc cag        2115
Trp Ser Ala Tyr Gly Gly Asp Phe Gly Asp Thr Pro Asn Asp Arg Gln
            690                 695                 700 ttc tgt atg aac ggt ctg gtc ttt gcc gac cgc acg ccg cat cca gcg        2163
Phe Cys Met Asn Gly Leu Val Phe Ala Asp Arg Thr Pro His Pro Ala
        705                 710                 715 ctg acg gaa gca aaa cac cag cag cag ttt ttc cag ttc cgt tta tcc        2211
Leu Thr Glu Ala Lys His Gln Gln Gln Phe Phe Gln Phe Arg Leu Ser
    720                 725                 730 ggg caa acc atc gaa gtg acc agc gaa tac ctg ttc cgt cat agc gat        2259
Gly Gln Thr Ile Glu Val Thr Ser Glu Tyr Leu Phe Arg His Ser Asp
735                 740                 745                 750 aac gag ctc ctg cac tgg atg gtg gcg ctg gat ggt aag ccg ctg gca        2307
Asn Glu Leu Leu His Trp Met Val Ala Leu Asp Gly Lys Pro Leu Ala
                755                 760                 765 agc ggt gaa gtg cct ctg gat gtc gct cca caa ggt aaa cag ttg att        2355
Ser Gly Glu Val Pro Leu Asp Val Ala Pro Gln Gly Lys Gln Leu Ile
            770                 775                 780 gaa ctg cct gaa cta ccg cag ccg gag agc gcc ggg caa ctc tgg ctc        2403
Glu Leu Pro Glu Leu Pro Gln Pro Glu Ser Ala Gly Gln Leu Trp Leu
        785                 790                 795 aca gta cgc gta gtg caa ccg aac gcg acc gca tgg tca gaa gcc ggg        2451
Thr Val Arg Val Val Gln Pro Asn Ala Thr Ala Trp Ser Glu Ala Gly
    800                 805                 810 cac atc agc gcc tgg cag cag tgg cgt ctg gcg gaa aac ctc agt gtg        2499
His Ile Ser Ala Trp Gln Gln Trp Arg Leu Ala Glu Asn Leu Ser Val
815                 820                 825                 830
```

```
                                                                    -continued acg ctc ccc gcc gcg tcc cac gcc atc ccg cat ctg acc acc agc gaa    2547
Thr Leu Pro Ala Ala Ser His Ala Ile Pro His Leu Thr Thr Ser Glu
                835                 840                 845 atg gat ttt tgc atc gag ctg ggt aat aag cgt tgg caa ttt aac cgc    2595
Met Asp Phe Cys Ile Glu Leu Gly Asn Lys Arg Trp Gln Phe Asn Arg
        850                 855                 860 cag tca ggc ttt ctt tca cag atg tgg att ggc gat aaa aaa caa ctg    2643
Gln Ser Gly Phe Leu Ser Gln Met Trp Ile Gly Asp Lys Lys Gln Leu
    865                 870                 875 ctg acg ccg ctg cgc gat cag ttc acc cgt gca ccg ctg gat aac gac    2691
Leu Thr Pro Leu Arg Asp Gln Phe Thr Arg Ala Pro Leu Asp Asn Asp
880                 885                 890 att ggc gta agt gaa gcg acc cgc att gac cct aac gcc tgg gtc gaa    2739
Ile Gly Val Ser Glu Ala Thr Arg Ile Asp Pro Asn Ala Trp Val Glu
895                 900                 905                 910 cgc tgg aag gcg gcg ggc cat tac cag gcc gaa gca gcg ttg ttg cag    2787
Arg Trp Lys Ala Ala Gly His Tyr Gln Ala Glu Ala Ala Leu Leu Gln
                915                 920                 925 tgc acg gca gat aca ctt gct gat gcg gtg ctg att acg acc gct cac    2835
Cys Thr Ala Asp Thr Leu Ala Asp Ala Val Leu Ile Thr Thr Ala His
        930                 935                 940 gcg tgg cag cat cag ggg aaa acc tta ttt atc agc cgg aaa acc tac    2883
Ala Trp Gln His Gln Gly Lys Thr Leu Phe Ile Ser Arg Lys Thr Tyr
    945                 950                 955 cgg att gat ggt agt ggt caa atg gcg att acc gtt gat gtt gaa gtg    2931
Arg Ile Asp Gly Ser Gly Gln Met Ala Ile Thr Val Asp Val Glu Val
960                 965                 970 gcg agc gat aca ccg cat ccg gcg cgg att ggc ctg aac tgc cag ctg    2979
Ala Ser Asp Thr Pro His Pro Ala Arg Ile Gly Leu Asn Cys Gln Leu
975                 980                 985                 990 gcg cag gta gca gag cgg gta aac tgg ctc gga tta ggg ccg caa gaa    3027
Ala Gln Val Ala Glu Arg Val Asn Trp Leu Gly Leu Gly Pro Gln Glu
                995                 1000                1005 aac tat ccc gac cgc ctt act gcc gcc tgt ttt gac cgc tgg gat ctg    3075
Asn Tyr Pro Asp Arg Leu Thr Ala Ala Cys Phe Asp Arg Trp Asp Leu
        1010                1015                1020 cca ttg tca gac atg tat acc ccg tac gtc ttc ccg agc gaa aac ggt    3123
Pro Leu Ser Asp Met Tyr Thr Pro Tyr Val Phe Pro Ser Glu Asn Gly
    1025                1030                1035 ctg cgc tgc ggg acg cgc gaa ttg aat tat ggc cca cac cag tgg cgc    3171
Leu Arg Cys Gly Thr Arg Glu Leu Asn Tyr Gly Pro His Gln Trp Arg
    1040                1045                1050 ggc gac ttc cag ttc aac atc agc cgc tac agt caa cag caa ctg atg    3219
Gly Asp Phe Gln Phe Asn Ile Ser Arg Tyr Ser Gln Gln Gln Leu Met
1055                1060                1065                1070 gaa acc agc cat cgc cat ctg ctg cac gcg gaa gaa ggc aca tgg ctg    3267
Glu Thr Ser His Arg His Leu Leu His Ala Glu Glu Gly Thr Trp Leu
                1075                1080                1085 aat atc gac ggt ttc cat atg ggg att ggt ggc gac gac tcc tgg agc    3315
Asn Ile Asp Gly Phe His Met Gly Ile Gly Gly Asp Asp Ser Trp Ser
        1090                1095                1100 ccg tca gta tcg gcg gaa ttc cag ctg agc gcc ggt cgc tac cat tac    3363
Pro Ser Val Ser Ala Glu Phe Gln Leu Ser Ala Gly Arg Tyr His Tyr
    1105                1110                1115 cag ttg gtc tgg tgt caa aaa taataataac cgggcaggcc atgtctgccc      3414
Gln Leu Val Trp Cys Gln Lys
    1120                1125 gtatttcgcg taaggaaatc cattatgtac tatttaaaaa acacaaactt ttggatgttc   3474
```

-continued

```
ggtttattct ttttcttttta ctttttatc atgggagcct acttcccgtt tttcccgatt     3534
tggctacatg acatcaacca tatcagcaaa agtgatacgg gtattatttt tgccgctatt     3594
tctctgttct cgctattatt ccaaccgctg tttggtctgc tttctgacaa actcggaact     3654
tgtttattgc agcttataat ggttacaaat aaagcaatag catcacaaat ttcacaaata     3714
aagcattttt ttcactgcat tctagttgtg gtttgtccaa actcatcaat gtatcttatc     3774
atgtctggat ccccaggaag ctcctctgtg tcctcataaa ccctaacctc ctctacttga     3834
gaggacattc caatcatagg ctgcccatcc accctctgtg tcctcctgtt aattaggtca     3894
cttaacaaaa aggaaattgg gtaggggttt ttcacagacc gctttctaag ggtaatttta     3954
aaatatctgg gaagtccctt ccactgctgt gttccagaag tgttggtaaa cagcccacaa     4014
atgtcaacag cagaaacata caagctgtca gctttgcaca agggcccaac ccctgctca      4074
tcaagaagca ctgtggttgc tgtgttagta atgtgcaaaa caggaggcac attttcccca     4134
cctgtgtagg ttccaaaata tctagtgttt tcatttttac ttggatcagg aacccagcac     4194
tccactggat aagcattatc cttatccaaa acagccttgt ggtcagtgtt catctgctga     4254
ctgtcaactg tagcattttt tggggttaca gtttgagcag gatatttggt cctgtagttt     4314
gctaacacac cctgcagctc caaaggttcc ccaccaacag caaaaaaatg aaaatttgac     4374
ccttgaatgg gttttccagc accattttca tgagtttttt gtgtccctga atgcaagttt     4434
aacatagcag ttaccccaat aacctcagtt ttaacagtaa cagcttccca catcaaaata     4494
tttccacagg ttaagtcctc atttaaatta ggcaaaggaa ttcttgaaga cgaaagggcc     4554
tcgtgatacg cctattttta taggttaatg tcatgataat aatggtttct tagacgtcag     4614
gtggcacttt tcggggaaat gtgcgcggaa cccctatttg tttattttc taaatacatt     4674
caaatatgta tccgctcatg agacaataac cctgataaat gcttcaataa tattgaaaaa     4734
ggaagagtat gagtattcaa catttccgtg tcgcccttat tccctttttt gcggcatttt     4794
gccttcctgt ttttgctcac ccagaaacgc tggtgaaagt aaaagatgct gaagatcagt     4854
tgggtgcacg agtgggttac atcgaactgg atctcaacag cggtaagatc cttgagagtt     4914
ttcgccccga agaacgtttt ccaatgatga gcacttttaa agttctgcta tgtggcgcgg     4974
tattatcccg tgttgacgcc gggcaagagc aactcggtcg ccgcatacac tattctcaga     5034
atgacttggt tgagtactca ccagtcacag aaaagcatct tacggatggc atgacagtaa     5094
gagaattatg cagtgctgcc ataaccatga gtgataacac tgcggccaac ttacttctga     5154
caacgatcgg aggaccgaag gagctaaccg cttttttgca caacatgggg gatcatgtaa     5214
ctcgccttga tcgttgggaa ccggagctga atgaagccat accaaacgac gagcgtgaca     5274
ccacgatgcc tgcagcaatg gcaacaacgt tgcgcaaact attaactggc gaactactta     5334
ctctagcttc ccggcaacaa ttaatagact ggatggaggc ggataaagtt gcaggaccac     5394
ttctgcgctc ggcccttccg gctggctggt ttattgctga taaatctgga gccggtgagc     5454
gtgggtctcg cggtatcatt gcagcactgg ggccagatgg taagccctcc cgtatcgtag     5514
ttatctacac gacggggagt caggcaacta tggatgaacg aaatagacag atcgctgaga     5574
taggtgcctc actgattaag cattggtaac tgtcagacca agtttactca tatatacttt     5634
agattgattt aaaacttcat ttttaattta aaaggatcta ggtgaagatc cttttttgata     5694
atctcatgac caaaatccct taacgtgagt tttcgttcca ctgagcgtca gaccccgtag     5754
aaaagatcaa aggatcttct tgagatcctt ttttctgcg cgtaatctgc tgcttgcaaa     5814
caaaaaaacc accgctacca gcggtggttt gtttgccgga tcaagagcta ccaactcttt     5874
```

-continued

```
ttccgaaggt aactggcttc agcagagcgc agataccaaa tactgtcctt ctagtgtagc     5934
cgtagttagg ccaccacttc aagaactctg tagcaccgcc tacatacctc gctctgctaa     5994
tcctgttacc agtggctgct gccagtggcg ataagtcgtg tcttaccggg ttggactcaa     6054
gacgatagtt accggataag cgcagcggt cgggctgaac ggggggttcg tgcacacagc      6114
ccagcttgga gcgaacgacc tacaccgaac tgagatacct acagcgtgag cattgagaaa     6174
gcgccacgct tcccgaaggg agaaaggcgg acaggtatcc ggtaagcggc agggtcggaa     6234
caggagagcg cacgagggag cttccagggg gaaacgcctg gtatctttat agtcctgtcg     6294
ggtttcgcca cctctgactt gagcgtcgat ttttgtgatg ctcgtcaggg gggcggagcc     6354
tatgaaaaaa cgccagcaac gcggccttt tacggttcct ggccttttgc tggccttttg      6414
ctcacatgtt ctttcctgcg ttatcccctg attctgtgga taaccgtatt accgcctttg     6474
agtgagctga taccgctcgc cgcagccgaa cgaccgagcg cagcgagtca gtgagcgagg     6534
aagcggaaga gcgcctgatg cggtattttc tccttacgca tctgtgcggt atttcacacc     6594
gcatatggtg cactctcagt acaatctgct ctgatgccgc atagttaagc cagtatacac     6654
tccgctatcg ctacgtgact gggtcatggc tgcgccccga cacccgccaa cacccgctga     6714
cgcgccctga cgggcttgtc tgctcccggc atccgcttac agacaagctg tgaccgtctc     6774
cgggagctgc atgtgtcaga ggttttcacc gtcatcaccg aaacgcgcga ggcagctgtg     6834
gaatgtgtgt cagttagggt gtggaaagtc cccaggctcc ccagcaggca gaagtatgca     6894
aagcatgcat ctcaattagt cagcaaccag gtgtggaaag tccccaggct ccccagcagg     6954
cagaagtatg caaagcatgc atctcaatta gtcagcaacc atagtcccgc ccctaactcc     7014
gcccatcccg cccctaactc cgcccagttc cgcccattct ccgccccatg ctgactaat      7074 tttttttatt tatgcagagg ccgaggccgc ctcggcctct gagctattcc agaagtagtg     7134
aggaggcttt tttggaggcc taggcttttg caaaaagct                            7173
```

<210> SEQ ID NO 39
<211> LENGTH: 1125
<212> TYPE: PRT
<213> ORGANISM: Artificial Sequence
<220> FEATURE:
<223> OTHER INFORMATION: Description of Artificial Sequence: fusion
    protein comprising a nuclear localization signal from SV40 large T
    antigen, a TAT signal sequence from HIV, a region of the human
    HIF-1alpha gene, and the Beta-galactosidase protein from E. coli.

<400> SEQUENCE: 39

```
Met Ala Pro Lys Lys Arg Lys Arg Ser Tyr Gly Arg Lys Lys Arg
1               5                   10                  15

Arg Gln Arg Arg Arg Ser Asn Pro Phe Ser Thr Gln Asp Thr Asp
            20                  25                  30

Leu Asp Leu Glu Met Leu Ala Pro Tyr Ile Pro Met Asp Asp Phe
        35                  40                  45

Gln Leu Arg Ser Phe Asp Gln Leu Ser Pro Leu Glu Ser Ser Ala
    50                  55                  60

Ser Pro Glu Ser Ala Ser Pro Gln Ser Thr Val Thr Val Phe Gln Gln
65                  70                  75                  80

Val Pro Val Gly Glu Asp Gln Lys Gln His Leu Glu Leu Ser Arg Asp
                85                  90                  95

Ile Ala Gln Arg Phe Asn Ala Leu Tyr Gly Glu Ile Asp Pro Val Val
            100                 105                 110
```

```
Leu Gln Arg Arg Asp Trp Glu Asn Pro Gly Val Thr Gln Leu Asn Arg
        115                 120                 125

Leu Ala Ala His Pro Pro Phe Ala Ser Trp Arg Asn Ser Glu Glu Ala
    130                 135                 140

Arg Thr Asp Arg Pro Ser Gln Gln Leu Arg Ser Leu Asn Gly Glu Trp
145                 150                 155                 160

Arg Phe Ala Trp Phe Pro Ala Pro Glu Ala Val Pro Glu Ser Trp Leu
                165                 170                 175

Glu Cys Asp Leu Pro Glu Ala Asp Thr Val Val Pro Ser Asn Trp
                180                 185                 190

Gln Met His Gly Tyr Asp Ala Pro Ile Tyr Thr Asn Val Thr Tyr Pro
        195                 200                 205

Ile Thr Val Asn Pro Pro Phe Val Pro Thr Glu Asn Pro Thr Gly Cys
    210                 215                 220

Tyr Ser Leu Thr Phe Asn Val Asp Glu Ser Trp Leu Gln Glu Gly Gln
225                 230                 235                 240

Thr Arg Ile Ile Phe Asp Gly Val Asn Ser Ala Phe His Leu Trp Cys
                245                 250                 255

Asn Gly Arg Trp Val Gly Tyr Gly Gln Asp Ser Arg Leu Pro Ser Glu
            260                 265                 270

Phe Asp Leu Ser Ala Phe Leu Arg Ala Gly Glu Asn Arg Leu Ala Val
        275                 280                 285

Met Val Leu Arg Trp Ser Asp Gly Ser Tyr Leu Glu Asp Gln Asp Met
    290                 295                 300

Trp Arg Met Ser Gly Ile Phe Arg Asp Val Ser Leu Leu His Lys Pro
305                 310                 315                 320

Thr Thr Gln Ile Ser Asp Phe His Val Ala Thr Arg Phe Asn Asp Asp
                325                 330                 335

Phe Ser Arg Ala Val Leu Glu Ala Glu Val Gln Met Cys Gly Glu Leu
            340                 345                 350

Arg Asp Tyr Leu Arg Val Thr Val Ser Leu Trp Gln Gly Glu Thr Gln
        355                 360                 365

Val Ala Ser Gly Thr Ala Pro Phe Gly Gly Glu Ile Ile Asp Glu Arg
    370                 375                 380

Gly Gly Tyr Ala Asp Arg Val Thr Leu Arg Leu Asn Val Glu Asn Pro
385                 390                 395                 400

Lys Leu Trp Ser Ala Glu Ile Pro Asn Leu Tyr Arg Ala Val Val Glu
                405                 410                 415

Leu His Thr Ala Asp Gly Thr Leu Ile Glu Ala Glu Ala Cys Asp Val
            420                 425                 430

Gly Phe Arg Glu Val Arg Ile Glu Asn Gly Leu Leu Leu Leu Asn Gly
        435                 440                 445

Lys Pro Leu Leu Ile Arg Gly Val Asn Arg His Glu His His Pro Leu
    450                 455                 460

His Gly Gln Val Met Asp Glu Gln Thr Met Val Gln Asp Ile Leu Leu
465                 470                 475                 480

Met Lys Gln Asn Asn Phe Asn Ala Val Arg Cys Ser His Tyr Pro Asn
                485                 490                 495

His Pro Leu Trp Tyr Thr Leu Cys Asp Arg Tyr Gly Leu Tyr Val Val
            500                 505                 510

Asp Glu Ala Asn Ile Glu Thr His Gly Met Val Pro Met Asn Arg Leu
        515                 520                 525

Thr Asp Asp Pro Arg Trp Leu Pro Ala Met Ser Glu Arg Val Thr Arg
```

-continued

```
            530                 535                 540
Met Val Gln Arg Asp Arg Asn His Pro Ser Val Ile Ile Trp Ser Leu
545                 550                 555                 560

Gly Asn Glu Ser Gly His Gly Ala Asn His Asp Ala Leu Tyr Arg Trp
                565                 570                 575

Ile Lys Ser Val Asp Pro Ser Arg Pro Val Gln Tyr Glu Gly Gly Gly
                580                 585                 590

Ala Asp Thr Thr Ala Thr Asp Ile Ile Cys Pro Met Tyr Ala Arg Val
                595                 600                 605

Asp Glu Asp Gln Pro Phe Pro Ala Val Pro Lys Trp Ser Ile Lys Lys
610                 615                 620

Trp Leu Ser Leu Pro Gly Glu Thr Arg Pro Leu Ile Leu Cys Glu Tyr
625                 630                 635                 640

Ala His Ala Met Gly Asn Ser Leu Gly Gly Phe Ala Lys Tyr Trp Gln
                645                 650                 655

Ala Phe Arg Gln Tyr Pro Arg Leu Gln Gly Gly Phe Val Trp Asp Trp
                660                 665                 670

Val Asp Gln Ser Leu Ile Lys Tyr Asp Glu Asn Gly Asn Pro Trp Ser
                675                 680                 685

Ala Tyr Gly Gly Asp Phe Gly Asp Thr Pro Asn Asp Arg Gln Phe Cys
                690                 695                 700

Met Asn Gly Leu Val Phe Ala Asp Arg Thr Pro His Pro Ala Leu Thr
705                 710                 715                 720

Glu Ala Lys His Gln Gln Gln Phe Phe Gln Phe Arg Leu Ser Gly Gln
                725                 730                 735

Thr Ile Glu Val Thr Ser Glu Tyr Leu Phe Arg His Ser Asp Asn Glu
                740                 745                 750

Leu Leu His Trp Met Val Ala Leu Asp Gly Lys Pro Leu Ala Ser Gly
                755                 760                 765

Glu Val Pro Leu Asp Val Ala Pro Gln Gly Lys Gln Leu Ile Glu Leu
                770                 775                 780

Pro Glu Leu Pro Gln Pro Glu Ser Ala Gly Gln Leu Trp Leu Thr Val
785                 790                 795                 800

Arg Val Val Gln Pro Asn Ala Thr Ala Trp Ser Glu Ala Gly His Ile
                805                 810                 815

Ser Ala Trp Gln Gln Trp Arg Leu Ala Glu Asn Leu Ser Val Thr Leu
                820                 825                 830

Pro Ala Ala Ser His Ala Ile Pro His Leu Thr Thr Ser Glu Met Asp
                835                 840                 845

Phe Cys Ile Glu Leu Gly Asn Lys Arg Trp Gln Phe Asn Arg Gln Ser
850                 855                 860

Gly Phe Leu Ser Gln Met Trp Ile Gly Asp Lys Lys Gln Leu Leu Thr
865                 870                 875                 880

Pro Leu Arg Asp Gln Phe Thr Arg Ala Pro Leu Asp Asn Asp Ile Gly
                885                 890                 895

Val Ser Glu Ala Thr Arg Ile Asp Pro Asn Ala Trp Val Glu Arg Trp
                900                 905                 910

Lys Ala Ala Gly His Tyr Gln Ala Glu Ala Ala Leu Leu Gln Cys Thr
                915                 920                 925

Ala Asp Thr Leu Ala Asp Ala Val Leu Ile Thr Thr Ala His Ala Trp
                930                 935                 940

Gln His Gln Gly Lys Thr Leu Phe Ile Ser Arg Lys Thr Tyr Arg Ile
945                 950                 955                 960
```

-continued

```
Asp Gly Ser Gly Gln Met Ala Ile Thr Val Asp Val Glu Val Ala Ser
            965                 970                 975

Asp Thr Pro His Pro Ala Arg Ile Gly Leu Asn Cys Gln Leu Ala Gln
            980                 985                 990

Val Ala Glu Arg Val Asn Trp Leu Gly Leu Gly Pro Gln Glu Asn Tyr
        995                 1000                1005

Pro Asp Arg Leu Thr Ala Ala Cys Phe Asp Arg Trp Asp Leu Pro Leu
    1010                1015                1020

Ser Asp Met Tyr Thr Pro Tyr Val Phe Pro Ser Glu Asn Gly Leu Arg
1025                1030                1035                1040

Cys Gly Thr Arg Glu Leu Asn Tyr Gly Pro His Gln Trp Arg Gly Asp
            1045                1050                1055

Phe Gln Phe Asn Ile Ser Arg Tyr Ser Gln Gln Gln Leu Met Glu Thr
            1060                1065                1070

Ser His Arg His Leu Leu His Ala Glu Glu Gly Thr Trp Leu Asn Ile
        1075                1080                1085

Asp Gly Phe His Met Gly Ile Gly Gly Asp Asp Ser Trp Ser Pro Ser
    1090                1095                1100

Val Ser Ala Glu Phe Gln Leu Ser Ala Gly Arg Tyr His Tyr Gln Leu
1105                1110                1115                1120

Val Trp Cys Gln Lys
            1125

<210> SEQ ID NO 40
<211> LENGTH: 7059
<212> TYPE: DNA
<213> ORGANISM: Artificial Sequence
<220> FEATURE:
<223> OTHER INFORMATION: Description of Artificial Sequence: fusion gene
      of 00 and 11
<220> FEATURE:
<221> NAME/KEY: CDS
<222> LOCATION: (10)..(3270)

<400> SEQUENCE: 40 aagcttgac atg gcg cct aag aag aag agg aag aga tca tat ggt cgt aag      51
           Met Ala Pro Lys Lys Lys Arg Lys Arg Ser Tyr Gly Arg Lys
           1               5                   10 aaa cgt cgc caa cgt cgc cga aga tct tta gac ttg gag atg tta gct       99
Lys Arg Arg Gln Arg Arg Arg Ser Leu Asp Leu Glu Met Leu Ala
 15                  20                  25                  30 ccc tat atc cca atg gat gat gac ttc cag tta cag gta ccg gtg ggt      147
Pro Tyr Ile Pro Met Asp Asp Asp Phe Gln Leu Gln Val Pro Val Gly
                 35                  40                  45 gaa gac cag aaa cag cac ctc gaa ctg agc cgc gat att gcc cag cgt      195
Glu Asp Gln Lys Gln His Leu Glu Leu Ser Arg Asp Ile Ala Gln Arg
             50                  55                  60 ttc aac gcg ctg tat ggc gag atc gat ccc gtc gtt tta caa cgt cgt      243
Phe Asn Ala Leu Tyr Gly Glu Ile Asp Pro Val Val Leu Gln Arg Arg
         65                  70                  75 gac tgg gaa aac cct ggc gtt acc caa ctt aat cgc ctt gca gca cat      291
Asp Trp Glu Asn Pro Gly Val Thr Gln Leu Asn Arg Leu Ala Ala His
     80                  85                  90 ccc cct ttc gcc agc tgg cgt aat agc gaa gag gcc cgc acc gat cgc      339
Pro Pro Phe Ala Ser Trp Arg Asn Ser Glu Glu Ala Arg Thr Asp Arg
 95                 100                 105                 110 cct tcc caa cag ttg cgc agc ctg aat ggc gaa tgg cgc ttt gcc tgg      387
Pro Ser Gln Gln Leu Arg Ser Leu Asn Gly Glu Trp Arg Phe Ala Trp
                115                 120                 125
```

-continued

| | | |
|---|---|---|
| ttt ccg gca cca gaa gcg gtg ccg gaa agc tgg ctg gag tgc gat ctt<br>Phe Pro Ala Pro Glu Ala Val Pro Glu Ser Trp Leu Glu Cys Asp Leu<br>130                        135                      140 | | 435 |
| cct gag gcc gat act gtc gtc gtc ccc tca aac tgg cag atg cac ggt<br>Pro Glu Ala Asp Thr Val Val Val Pro Ser Asn Trp Gln Met His Gly<br>145                        150                      155 | | 483 |
| tac gat gcg ccc atc tac acc aac gta acc tat ccc att acg gtc aat<br>Tyr Asp Ala Pro Ile Tyr Thr Asn Val Thr Tyr Pro Ile Thr Val Asn<br>160                        165                      170 | | 531 |
| ccg ccg ttt gtt ccc acg gag aat ccg acg ggt tgt tac tcg ctc aca<br>Pro Pro Phe Val Pro Thr Glu Asn Pro Thr Gly Cys Tyr Ser Leu Thr<br>175                        180                      190 | | 579 |
| ttt aat gtt gat gaa agc tgg cta cag gaa ggc cag acg cga att att<br>Phe Asn Val Asp Glu Ser Trp Leu Gln Glu Gly Gln Thr Arg Ile Ile<br>                195                      200                      205 | | 627 |
| ttt gat ggc gtt aac tcg gcg ttt cat ctg tgg tgc aac ggg cgc tgg<br>Phe Asp Gly Val Asn Ser Ala Phe His Leu Trp Cys Asn Gly Arg Trp<br>                210                      215                      220 | | 675 |
| gtc ggt tac ggc cag gac agt cgt ttg ccg tct gaa ttt gac ctg agc<br>Val Gly Tyr Gly Gln Asp Ser Arg Leu Pro Ser Glu Phe Asp Leu Ser<br>225                        230                      235 | | 723 |
| gca ttt tta cgc gcc gga gaa aac cgc ctc gcg gtg atg gtg ctg cgt<br>Ala Phe Leu Arg Ala Gly Glu Asn Arg Leu Ala Val Met Val Leu Arg<br>240                        245                      250 | | 771 |
| tgg agt gac ggc agt tat ctg gaa gat cag gat atg tgg cgg atg agc<br>Trp Ser Asp Gly Ser Tyr Leu Glu Asp Gln Asp Met Trp Arg Met Ser<br>255                        260                      265                      270 | | 819 |
| ggc att ttc cgt gac gtc tcg ttg ctg cat aaa ccg act aca caa atc<br>Gly Ile Phe Arg Asp Val Ser Leu Leu His Lys Pro Thr Thr Gln Ile<br>                275                      280                      285 | | 867 |
| agc gat ttc cat gtt gcc act cgc ttt aat gat gat ttc agc cgc gct<br>Ser Asp Phe His Val Ala Thr Arg Phe Asn Asp Asp Phe Ser Arg Ala<br>                290                      295                      300 | | 915 |
| gta ctg gag gct gaa gtt cag atg tgc ggc gag ttg cgt gac tac cta<br>Val Leu Glu Ala Glu Val Gln Met Cys Gly Glu Leu Arg Asp Tyr Leu<br>305                        310                      315 | | 963 |
| cgg gta aca gtt tct tta tgg cag ggt gaa acg cag gtc gcc agc ggc<br>Arg Val Thr Val Ser Leu Trp Gln Gly Glu Thr Gln Val Ala Ser Gly<br>320                        325                      330 | | 1011 |
| acc gcg cct ttc ggc ggt gaa att atc gat gag cgt ggt ggt tat gcc<br>Thr Ala Pro Phe Gly Gly Glu Ile Ile Asp Glu Arg Gly Gly Tyr Ala<br>335                        340                      345                      350 | | 1059 |
| gat cgc gtc aca cta cgt ctg aac gtc gaa aac ccg aaa ctg tgg agc<br>Asp Arg Val Thr Leu Arg Leu Asn Val Glu Asn Pro Lys Leu Trp Ser<br>                355                      360                      365 | | 1107 |
| gcc gaa atc ccg aat ctc tat cgt gcg gtg gtt gaa ctg cac acc gcc<br>Ala Glu Ile Pro Asn Leu Tyr Arg Ala Val Val Glu Leu His Thr Ala<br>                370                      375                      380 | | 1155 |
| gac ggc acg ctg att gaa gca gaa gcc tgc gat gtc ggt ttc cgc gag<br>Asp Gly Thr Leu Ile Glu Ala Glu Ala Cys Asp Val Gly Phe Arg Glu<br>385                        390                      395 | | 1203 |
| gtg cgg att gaa aat ggt ctg ctg ctg ctg aac ggc aag ccg ttg ctg<br>Val Arg Ile Glu Asn Gly Leu Leu Leu Leu Asn Gly Lys Pro Leu Leu<br>400                        405                      410 | | 1251 |
| att cga ggc gtt aac cgt cac gag cat cat cct ctg cat ggt cag gtc<br>Ile Arg Gly Val Asn Arg His Glu His His Pro Leu His Gly Gln Val<br>415                        420                      425                      430 | | 1299 |
| atg gat gag cag acg atg gtg cag gat atc ctg ctg atg aag cag aac<br>Met Asp Glu Gln Thr Met Val Gln Asp Ile Leu Leu Met Lys Gln Asn | | 1347 |

-continued

```
                    435                 440                 445
aac ttt aac gcc gtg cgc tgt tcg cat tat ccg aac cat ccg ctg tgg      1395
Asn Phe Asn Ala Val Arg Cys Ser His Tyr Pro Asn His Pro Leu Trp
            450                 455                 460 tac acg ctg tgc gac cgc tac ggc ctg tat gtg gtg gat gaa gcc aat      1443
Tyr Thr Leu Cys Asp Arg Tyr Gly Leu Tyr Val Val Asp Glu Ala Asn
            465                 470                 475 att gaa acc cac ggc atg gtg cca atg aat cgt ctg acc gat gat ccg      1491
Ile Glu Thr His Gly Met Val Pro Met Asn Arg Leu Thr Asp Asp Pro
        480                 485                 490 cgc tgg cta ccg gcg atg agc gaa cgc gta acg cga atg gtg cag cgc      1539
Arg Trp Leu Pro Ala Met Ser Glu Arg Val Thr Arg Met Val Gln Arg
495                 500                 505                 510 gat cgt aat cac ccg agt gtg atc atc tgg tcg ctg ggg aat gaa tca      1587
Asp Arg Asn His Pro Ser Val Ile Ile Trp Ser Leu Gly Asn Glu Ser
                515                 520                 525 ggc cac ggc gct aat cac gac gcg ctg tat cgc tgg atc aaa tct gtc      1635
Gly His Gly Ala Asn His Asp Ala Leu Tyr Arg Trp Ile Lys Ser Val
            530                 535                 540 gat cct tcc cgc ccg gtg cag tat gaa ggc ggc gga gcc gac acc acg      1683
Asp Pro Ser Arg Pro Val Gln Tyr Glu Gly Gly Gly Ala Asp Thr Thr
            545                 550                 555 gcc acc gat att att tgc ccg atg tac gcg cgc gtg gat gaa gac cag      1731
Ala Thr Asp Ile Ile Cys Pro Met Tyr Ala Arg Val Asp Glu Asp Gln
        560                 565                 570 ccc ttc ccg gct gtg ccg aaa tgg tcc atc aaa aaa tgg ctt tcg cta      1779
Pro Phe Pro Ala Val Pro Lys Trp Ser Ile Lys Lys Trp Leu Ser Leu
575                 580                 585                 590 cct gga gag acg cgc ccg ctg atc ctt tgc gaa tac gcc cac gcg atg      1827
Pro Gly Glu Thr Arg Pro Leu Ile Leu Cys Glu Tyr Ala His Ala Met
                595                 600                 605 ggt aac agt ctt ggc ggt ttc gct aaa tac tgg cag gcg ttt cgt cag      1875
Gly Asn Ser Leu Gly Gly Phe Ala Lys Tyr Trp Gln Ala Phe Arg Gln
            610                 615                 620 tat ccc cgt tta cag ggc ggc ttc gtc tgg gac tgg gtg gat cag tcg      1923
Tyr Pro Arg Leu Gln Gly Gly Phe Val Trp Asp Trp Val Asp Gln Ser
            625                 630                 635 ctg att aaa tat gat gaa aac ggc aac ccg tgg tcg gct tac ggc ggt      1971
Leu Ile Lys Tyr Asp Glu Asn Gly Asn Pro Trp Ser Ala Tyr Gly Gly
        640                 645                 650 gat ttt ggc gat acg ccg aac gat cgc cag ttc tgt atg aac ggt ctg      2019
Asp Phe Gly Asp Thr Pro Asn Asp Arg Gln Phe Cys Met Asn Gly Leu
655                 660                 665                 670 gtc ttt gcc gac cgc acg ccg cat cca gcg ctg acg gaa gca aaa cac      2067
Val Phe Ala Asp Arg Thr Pro His Pro Ala Leu Thr Glu Ala Lys His
                675                 680                 685 cag cag cag ttt ttc cag ttc cgt tta tcc ggg caa acc atc gaa gtg      2115
Gln Gln Gln Phe Phe Gln Phe Arg Leu Ser Gly Gln Thr Ile Glu Val
            690                 695                 700 acc agc gaa tac ctg ttc cgt cat agc gat aac gag ctc ctg cac tgg      2163
Thr Ser Glu Tyr Leu Phe Arg His Ser Asp Asn Glu Leu Leu His Trp
            705                 710                 715 atg gtg gcg ctg gat ggt aag ccg ctg gca agc ggt gaa gtg cct ctg      2211
Met Val Ala Leu Asp Gly Lys Pro Leu Ala Ser Gly Glu Val Pro Leu
        720                 725                 730 gat gtc gct cca caa ggt aaa cag ttg att gaa ctg cct gaa cta ccg      2259
Asp Val Ala Pro Gln Gly Lys Gln Leu Ile Glu Leu Pro Glu Leu Pro
735                 740                 745                 750 cag ccg gag agc gcc ggg caa ctc tgg ctc aca gta cgc gta gtg caa      2307
```

-continued

```
Gln Pro Glu Ser Ala Gly Gln Leu Trp Leu Thr Val Arg Val Val Gln
                755                 760                 765 ccg aac gcg acc gca tgg tca gaa gcc ggg cac atc agc gcc tgg cag    2355
Pro Asn Ala Thr Ala Trp Ser Glu Ala Gly His Ile Ser Ala Trp Gln
                770                 775                 780 cag tgg cgt ctg gcg gaa aac ctc agt gtg acg ctc ccc gcc gcg tcc    2403
Gln Trp Arg Leu Ala Glu Asn Leu Ser Val Thr Leu Pro Ala Ala Ser
                785                 790                 795 cac gcc atc ccg cat ctg acc acc agc gaa atg gat ttt tgc atc gag    2451
His Ala Ile Pro His Leu Thr Thr Ser Glu Met Asp Phe Cys Ile Glu
                800                 805                 810 ctg ggt aat aag cgt tgg caa ttt aac cgc cag tca ggc ttt ctt tca    2499
Leu Gly Asn Lys Arg Trp Gln Phe Asn Arg Gln Ser Gly Phe Leu Ser
815                 820                 825                 830 cag atg tgg att ggc gat aaa aaa caa ctg ctg acg ccg ctg cgc gat    2547
Gln Met Trp Ile Gly Asp Lys Lys Gln Leu Leu Thr Pro Leu Arg Asp
                835                 840                 845 cag ttc acc cgt gca ccg ctg gat aac gac att ggc gta agt gaa gcg    2595
Gln Phe Thr Arg Ala Pro Leu Asp Asn Asp Ile Gly Val Ser Glu Ala
                850                 855                 860 acc cgc att gac cct aac gcc tgg gtc gaa cgc tgg aag gcg gcg ggc    2643
Thr Arg Ile Asp Pro Asn Ala Trp Val Glu Arg Trp Lys Ala Ala Gly
                865                 870                 875 cat tac cag gcc gaa gca gcg ttg ttg cag tgc acg gca gat aca ctt    2691
His Tyr Gln Ala Glu Ala Ala Leu Leu Gln Cys Thr Ala Asp Thr Leu
                880                 885                 890 gct gat gcg gtg ctg att acg acc gct cac gcg tgg cag cat cag ggg    2739
Ala Asp Ala Val Leu Ile Thr Thr Ala His Ala Trp Gln His Gln Gly
895                 900                 905                 910 aaa acc tta ttt atc agc cgg aaa acc tac cgg att gat ggt agt ggt    2787
Lys Thr Leu Phe Ile Ser Arg Lys Thr Tyr Arg Ile Asp Gly Ser Gly
                915                 920                 925 caa atg gcg att acc gtt gat gtt gaa gtg gcg agc gat aca ccg cat    2835
Gln Met Ala Ile Thr Val Asp Val Glu Val Ala Ser Asp Thr Pro His
                930                 935                 940 ccg gcg cgg att ggc ctg aac tgc cag ctg gcg cag gta gca gag cgg    2883
Pro Ala Arg Ile Gly Leu Asn Cys Gln Leu Ala Gln Val Ala Glu Arg
                945                 950                 955 gta aac tgg ctc gga tta ggg ccg caa gaa aac tat ccc gac cgc ctt    2931
Val Asn Trp Leu Gly Leu Gly Pro Gln Glu Asn Tyr Pro Asp Arg Leu
                960                 965                 970 act gcc gcc tgt ttt gac cgc tgg gat ctg cca ttg tca gac atg tat    2979
Thr Ala Ala Cys Phe Asp Arg Trp Asp Leu Pro Leu Ser Asp Met Tyr
975                 980                 985                 990 acc ccg tac gtc ttc ccg agc gaa aac ggt ctg cgc tgc ggg acg cgc    3027
Thr Pro Tyr Val Phe Pro Ser Glu Asn Gly Leu Arg Cys Gly Thr Arg
                995                 1000                1005 gaa ttg aat tat ggc cca cac cag tgg cgc ggc gac ttc cag ttc aac    3075
Glu Leu Asn Tyr Gly Pro His Gln Trp Arg Gly Asp Phe Gln Phe Asn
                1010                1015                1020 atc agc cgc tac agt caa cag caa ctg atg gaa acc agc cat cgc cat    3123
Ile Ser Arg Tyr Ser Gln Gln Gln Leu Met Glu Thr Ser His Arg His
                1025                1030                1035 ctg ctg cac gcg gaa gaa ggc aca tgg ctg aat atc gac ggt ttc cat    3171
Leu Leu His Ala Glu Glu Gly Thr Trp Leu Asn Ile Asp Gly Phe His
                1040                1045                1050 atg ggg att ggt ggc gac gac tcc tgg agc ccg tca gta tcg gcg gaa    3219
Met Gly Ile Gly Gly Asp Asp Ser Trp Ser Pro Ser Val Ser Ala Glu
1055                1060                1065                1070
```

-continued

| | |
|---|---|
| ttc cag ctg agc gcc ggt cgc tac cat tac cag ttg gtc tgg tgt caa<br>Phe Gln Leu Ser Ala Gly Arg Tyr His Tyr Gln Leu Val Trp Cys Gln<br>                    1075                    1080                    1085 | 3267 |
| aaa taataataac cgggcaggcc atgtctgccc gtatttcgcg taaggaaatc<br>Lys | 3320 |
| cattatgtac tatttaaaaa acacaaactt ttggatgttc ggtttattct ttttctttta | 3380 |
| ctttttttatc atgggagcct acttcccgtt tttcccgatt tggctacatg acatcaacca | 3440 |
| tatcagcaaa agtgatacgg gtattatttt tgccgctatt tctctgttct cgctattatt | 3500 |
| ccaaccgctg tttggtctgc tttctgacaa actcggaact tgtttattgc agcttataat | 3560 |
| ggttacaaat aaagcaatag catcacaaat ttcacaaata aagcattttt ttcactgcat | 3620 |
| tctagttgtg gtttgtccaa actcatcaat gtatcttatc atgtctggat ccccaggaag | 3680 |
| ctcctctgtg tcctcataaa ccctaacctc ctctacttga gaggacattc caatcatagg | 3740 |
| ctgcccatcc accctctgtg tcctcctgtt aattaggtca cttaacaaaa aggaaattgg | 3800 |
| gtaggggttt ttcacagacc gctttctaag ggtaatttta aaatatctgg gaagtccctt | 3860 |
| ccactgctgt gttccagaag tgttggtaaa cagcccacaa atgtcaacag cagaaacata | 3920 |
| caagctgtca gctttgcaca agggcccaac accctgctca tcaagaagca ctgtggttgc | 3980 |
| tgtgttagta atgtgcaaaa caggaggcac attttcccca cctgtgtagg ttccaaaata | 4040 |
| tctagtgttt tcattttttac ttggatcagg aacccagcac tccactggat aagcattatc | 4100 |
| cttatccaaa acagccttgt ggtcagtgtt catctgctga ctgtcaactg tagcattttt | 4160 |
| tggggttaca gtttgagcag gatatttggt cctgtagttt gctaacacac cctgcagctc | 4220 |
| caaaggttcc ccaccaacag caaaaaaatg aaaatttgac ccttgaatgg gttttccagc | 4280 |
| accattttca tgagtttttt gtgtccctga atgcaagttt aacatagcag ttaccccaat | 4340 |
| aacctcagtt ttaacagtaa cagcttccca catcaaaata tttccacagg ttaagtcctc | 4400 |
| atttaaatta ggcaaaggaa ttcttgaaga cgaaagggcc tcgtgatacg cctatttta | 4460 |
| taggttaatg tcatgataat aatggtttct tagacgtcag gtggcacttt tcggggaaat | 4520 |
| gtgcgcggaa cccctatttg tttatttttc taaatacatt caaatatgta tccgctcatg | 4580 |
| agacaataac cctgataaat gcttcaataa tattgaaaaa ggaagagtat gagtattcaa | 4640 |
| catttccgtg tcgcccttat tccctttttt gcggcatttt gccttcctgt ttttgctcac | 4700 |
| ccagaaacgc tggtgaaagt aaaagatgct gaagatcagt tgggtgcacg agtgggttac | 4760 |
| atcgaactgg atctcaacag cggtaagatc cttgagagtt ttcgccccga agaacgtttt | 4820 |
| ccaatgatga gcacttttaa agttctgcta tgtggcgcgg tattatcccg tgttgacgcc | 4880 |
| gggcaagagc aactcggtcg ccgcatacac tattctcaga atgacttggt tgagtactca | 4940 |
| ccagtcacag aaaagcatct tacggatggc atgacagtaa gagaattatg cagtgctgcc | 5000 |
| ataaccatga gtgataacac tgcggccaac ttacttctga caacgatcgg aggaccgaag | 5060 |
| gagctaaccg cttttttgca caacatgggg gatcatgtaa ctcgccttga tcgttgggaa | 5120 |
| ccggagctga atgaagccat accaaacgac gagcgtgaca ccacgatgcc tgcagcaatg | 5180 |
| gcaacaacgt tgcgcaaact attaactggc gaactactta ctctagcttc ccggcaacaa | 5240 |
| ttaatagact ggatggaggc ggataaagtt gcaggaccac ttctgcgctc ggcccttccg | 5300 |
| gctggctggt ttattgctga taaatctgga gccggtgagc gtgggtctcg cggtatcatt | 5360 |
| gcagcactgg ggccagatgg taagccctcc cgtatcgtag ttatctacac gacggggagt | 5420 |
| caggcaacta tggatgaacg aaatagacag atcgctgaga taggtgcctc actgattaag | 5480 |

-continued

```
cattggtaac tgtcagacca agtttactca tatatacttt agattgattt aaaacttcat      5540
ttttaattta aaaggatcta ggtgaagatc cttttttgata atctcatgac caaaatccct    5600
taacgtgagt tttcgttcca ctgagcgtca gaccccgtag aaaagatcaa aggatcttct     5660
tgagatcctt tttttctgcg cgtaatctgc tgcttgcaaa caaaaaaacc accgctacca    5720
gcggtggttt gtttgccgga tcaagagcta ccaactcttt ttccgaaggt aactggcttc    5780
agcagagcgc agataccaaa tactgtcctt ctagtgtagc cgtagttagg ccaccacttc    5840
aagaactctg tagcaccgcc tacatacctc gctctgctaa tcctgttacc agtggctgct    5900
gccagtggcg ataagtcgtg tcttaccggg ttggactcaa gacgatagtt accggataag    5960
gcgcagcggt cgggctgaac ggggggttcg tgcacacagc ccagcttgga gcgaacgacc    6020
tacaccgaac tgagatacct acagcgtgag cattgagaaa gcgccacgct tcccgaaggg    6080
agaaaggcgg acaggtatcc ggtaagcggc agggtcggaa caggagagcg cacgagggag    6140
cttccagggg gaaacgcctg gtatctttat agtcctgtcg ggtttcgcca cctctgactt    6200
gagcgtcgat ttttgtgatg ctcgtcaggg gggcggagcc tatggaaaaa cgccagcaac    6260
gcggcctttt tacggttcct ggccttttgc tggccttttg ctcacatgtt ctttcctgcg    6320
ttatcccctg attctgtgga taaccgtatt accgcctttg agtgagctga taccgctcgc    6380
cgcagccgaa cgaccgagcg cagcgagtca gtgagcgagg aagcggaaga gcgcctgatg    6440
cggtattttc tccttacgca tctgtgcggt atttcacacc gcatatggtg cactctcagt    6500
acaatctgct ctgatgccgc atagttaagc cagtatacac tccgctatcg ctacgtgact    6560
gggtcatggc tgcgccccga cacccgccaa cacccgctga cgcgccctga cgggcttgtc    6620
tgctcccggc atccgcttac agacaagctg tgaccgtctc cgggagctgc atgtgtcaga    6680
ggttttcacc gtcatcaccg aaacgcgcga ggcagctgtg aatgtgtgt cagttagggt    6740 gtggaaagtc cccaggctcc ccagcaggca gaagtatgca aagcatgcat ctcaattagt    6800
cagcaaccag gtgtggaaag tccccaggct ccccagcagg cagaagtatg caaagcatgc    6860
atctcaatta gtcagcaacc atagtcccgc ccctaactcc gcccatcccg ccctaactc      6920 cgcccagttc cgcccattct ccgccccatg gctgactaat ttttttttatt tatgcagagg    6980 ccgaggccgc ctcggcctct gagctattcc agaagtagtg aggaggcttt tttggaggcc    7040
taggcttttg caaaaagct                                                  7059
```

<210> SEQ ID NO 41
<211> LENGTH: 1087
<212> TYPE: PRT
<213> ORGANISM: Artificial Sequence
<220> FEATURE:
<223> OTHER INFORMATION: Description of Artificial Sequence: fusion
      protein comprising a nuclear localization signal from SV40 large T
      antigen, a TAT signal sequence from HIV, a region of the human
      HIF-1alpha gene, and the Beta-galactosidase protein from E. coli.

<400> SEQUENCE: 41

```
Met Ala Pro Lys Lys Lys Arg Lys Arg Ser Tyr Gly Arg Lys Lys Arg
  1               5                  10                  15

Arg Gln Arg Arg Arg Arg Ser Leu Asp Leu Glu Met Leu Ala Pro Tyr
             20                  25                  30

Ile Pro Met Asp Asp Asp Phe Gln Leu Gln Val Pro Val Gly Glu Asp
         35                  40                  45

Gln Lys Gln His Leu Glu Leu Ser Arg Asp Ile Ala Gln Arg Phe Asn
     50                  55                  60
```

-continued

```
Ala Leu Tyr Gly Glu Ile Asp Pro Val Val Leu Gln Arg Arg Asp Trp
 65                  70                  75                  80

Glu Asn Pro Gly Val Thr Gln Leu Asn Arg Leu Ala Ala His Pro Pro
                 85                  90                  95

Phe Ala Ser Trp Arg Asn Ser Glu Glu Ala Arg Thr Asp Arg Pro Ser
            100                 105                 110

Gln Gln Leu Arg Ser Leu Asn Gly Glu Trp Arg Phe Ala Trp Phe Pro
        115                 120                 125

Ala Pro Glu Ala Val Pro Glu Ser Trp Leu Glu Cys Asp Leu Pro Glu
130                 135                 140

Ala Asp Thr Val Val Val Pro Ser Asn Trp Gln Met His Gly Tyr Asp
145                 150                 155                 160

Ala Pro Ile Tyr Thr Asn Val Thr Tyr Pro Ile Thr Val Asn Pro Pro
                165                 170                 175

Phe Val Pro Thr Glu Asn Pro Thr Gly Cys Tyr Ser Leu Thr Phe Asn
            180                 185                 190

Val Asp Glu Ser Trp Leu Gln Glu Gly Gln Thr Arg Ile Ile Phe Asp
        195                 200                 205

Gly Val Asn Ser Ala Phe His Leu Trp Cys Asn Gly Arg Trp Val Gly
210                 215                 220

Tyr Gly Gln Asp Ser Arg Leu Pro Ser Glu Phe Asp Leu Ser Ala Phe
225                 230                 235                 240

Leu Arg Ala Gly Glu Asn Arg Leu Ala Val Met Val Leu Arg Trp Ser
                245                 250                 255

Asp Gly Ser Tyr Leu Glu Asp Gln Asp Met Trp Arg Met Ser Gly Ile
            260                 265                 270

Phe Arg Asp Val Ser Leu Leu His Lys Pro Thr Thr Gln Ile Ser Asp
        275                 280                 285

Phe His Val Ala Thr Arg Phe Asn Asp Asp Phe Ser Arg Ala Val Leu
290                 295                 300

Glu Ala Glu Val Gln Met Cys Gly Glu Leu Arg Asp Tyr Leu Arg Val
305                 310                 315                 320

Thr Val Ser Leu Trp Gln Gly Glu Thr Gln Val Ala Ser Gly Thr Ala
                325                 330                 335

Pro Phe Gly Gly Glu Ile Ile Asp Glu Arg Gly Gly Tyr Ala Asp Arg
            340                 345                 350

Val Thr Leu Arg Leu Asn Val Glu Asn Pro Lys Leu Trp Ser Ala Glu
        355                 360                 365

Ile Pro Asn Leu Tyr Arg Ala Val Val Glu Leu His Thr Ala Asp Gly
370                 375                 380

Thr Leu Ile Glu Ala Glu Ala Cys Asp Val Gly Phe Arg Glu Val Arg
385                 390                 395                 400

Ile Glu Asn Gly Leu Leu Leu Leu Asn Gly Lys Pro Leu Leu Ile Arg
                405                 410                 415

Gly Val Asn Arg His Glu His His Pro Leu His Gly Gln Val Met Asp
            420                 425                 430

Glu Gln Thr Met Val Gln Asp Ile Leu Leu Met Lys Gln Asn Asn Phe
        435                 440                 445

Asn Ala Val Arg Cys Ser His Tyr Pro Asn His Pro Leu Trp Tyr Thr
450                 455                 460

Leu Cys Asp Arg Tyr Gly Leu Tyr Val Val Asp Glu Ala Asn Ile Glu
465                 470                 475                 480

Thr His Gly Met Val Pro Met Asn Arg Leu Thr Asp Asp Pro Arg Trp
```

-continued

```
                485                 490                 495
Leu Pro Ala Met Ser Glu Arg Val Thr Arg Met Val Gln Arg Asp Arg
            500                 505                 510
Asn His Pro Ser Val Ile Ile Trp Ser Leu Gly Asn Glu Ser Gly His
        515                 520                 525
Gly Ala Asn His Asp Ala Leu Tyr Arg Trp Ile Lys Ser Val Asp Pro
    530                 535                 540
Ser Arg Pro Val Gln Tyr Glu Gly Gly Gly Ala Asp Thr Thr Ala Thr
545                 550                 555                 560
Asp Ile Ile Cys Pro Met Tyr Ala Arg Val Asp Glu Asp Gln Pro Phe
                565                 570                 575
Pro Ala Val Pro Lys Trp Ser Ile Lys Lys Trp Leu Ser Leu Pro Gly
            580                 585                 590
Glu Thr Arg Pro Leu Ile Leu Cys Glu Tyr Ala His Ala Met Gly Asn
        595                 600                 605
Ser Leu Gly Gly Phe Ala Lys Tyr Trp Gln Ala Phe Arg Gln Tyr Pro
    610                 615                 620
Arg Leu Gln Gly Gly Phe Val Trp Asp Trp Val Asp Gln Ser Leu Ile
625                 630                 635                 640
Lys Tyr Asp Glu Asn Gly Asn Pro Trp Ser Ala Tyr Gly Gly Asp Phe
                645                 650                 655
Gly Asp Thr Pro Asn Asp Arg Gln Phe Cys Met Asn Gly Leu Val Phe
            660                 665                 670
Ala Asp Arg Thr Pro His Pro Ala Leu Thr Glu Ala Lys His Gln Gln
        675                 680                 685
Gln Phe Phe Gln Phe Arg Leu Ser Gly Gln Thr Ile Glu Val Thr Ser
    690                 695                 700
Glu Tyr Leu Phe Arg His Ser Asp Asn Glu Leu Leu His Trp Met Val
705                 710                 715                 720
Ala Leu Asp Gly Lys Pro Leu Ala Ser Gly Glu Val Pro Leu Asp Val
                725                 730                 735
Ala Pro Gln Gly Lys Gln Leu Ile Glu Leu Pro Glu Leu Pro Gln Pro
            740                 745                 750
Glu Ser Ala Gly Gln Leu Trp Leu Thr Val Arg Val Val Gln Pro Asn
        755                 760                 765
Ala Thr Ala Trp Ser Glu Ala Gly His Ile Ser Ala Trp Gln Gln Trp
    770                 775                 780
Arg Leu Ala Glu Asn Leu Ser Val Thr Leu Pro Ala Ala Ser His Ala
785                 790                 795                 800
Ile Pro His Leu Thr Thr Ser Glu Met Asp Phe Cys Ile Glu Leu Gly
                805                 810                 815
Asn Lys Arg Trp Gln Phe Asn Arg Gln Ser Gly Phe Leu Ser Gln Met
            820                 825                 830
Trp Ile Gly Asp Lys Lys Gln Leu Leu Thr Pro Leu Arg Asp Gln Phe
        835                 840                 845
Thr Arg Ala Pro Leu Asp Asn Asp Ile Gly Val Ser Glu Ala Thr Arg
    850                 855                 860
Ile Asp Pro Asn Ala Trp Val Glu Arg Trp Lys Ala Ala Gly His Tyr
865                 870                 875                 880
Gln Ala Glu Ala Ala Leu Leu Gln Cys Thr Ala Asp Thr Leu Ala Asp
                885                 890                 895
Ala Val Leu Ile Thr Thr Ala His Ala Trp Gln His Gln Gly Lys Thr
            900                 905                 910
```

```
Leu Phe Ile Ser Arg Lys Thr Tyr Arg Ile Asp Gly Ser Gly Gln Met
        915                 920                 925

Ala Ile Thr Val Asp Val Glu Val Ala Ser Asp Thr Pro His Pro Ala
        930                 935                 940

Arg Ile Gly Leu Asn Cys Gln Leu Ala Gln Val Ala Glu Arg Val Asn
945                 950                 955                 960

Trp Leu Gly Leu Gly Pro Gln Glu Asn Tyr Pro Asp Arg Leu Thr Ala
                965                 970                 975

Ala Cys Phe Asp Arg Trp Asp Leu Pro Leu Ser Asp Met Tyr Thr Pro
            980                 985                 990

Tyr Val Phe Pro Ser Glu Asn Gly Leu Arg Cys Gly Thr Arg Glu Leu
        995                 1000                1005

Asn Tyr Gly Pro His Gln Trp Arg Gly Asp Phe Gln Phe Asn Ile Ser
    1010                1015                1020

Arg Tyr Ser Gln Gln Gln Leu Met Glu Thr Ser His Arg His Leu Leu
1025                1030                1035                1040

His Ala Glu Glu Gly Thr Trp Leu Asn Ile Asp Gly Phe His Met Gly
            1045                1050                1055

Ile Gly Gly Asp Asp Ser Trp Ser Pro Ser Val Ser Ala Glu Phe Gln
            1060                1065                1070

Leu Ser Ala Gly Arg Tyr His Tyr Gln Leu Val Trp Cys Gln Lys
        1075                1080                1085

<210> SEQ ID NO 42
<211> LENGTH: 7439
<212> TYPE: DNA
<213> ORGANISM: Artificial Sequence
<220> FEATURE:
<223> OTHER INFORMATION: Description of Artificial Sequence: fusion gene
      of 00 and 11
<220> FEATURE:
<221> NAME/KEY: CDS
<222> LOCATION: (320)..(3799)

<400> SEQUENCE: 42
aagaaaccaa ttgtccatat tgcatcagac attgccgtca ctgcgtcttt tactggctct    60
tctcgctaac caaaccggta accccgctta ttaaaagcat tctgtaacaa agcgggacca   120
aagccatgac aaaaacgcgt aacaaaagtg tctataatca cggcagaaaa gtccacattg   180
attatttgca cggcgtcaca ctttgctatg ccatagcatt tttatccata agattagcgg   240
atcctacctg acgctttta tcgcaactct ctactgtttc tccatacccg tttttttggg    300
ctaacaggag gaattaacc atg ggg ggt tct cat cat cat cat cat cat ggt   352
                    Met Gly Gly Ser His His His His His His Gly
                     1               5                  10 atg gct agc atg act ggt gga cag caa atg ggt cgg gat ctg tac gac   400
Met Ala Ser Met Thr Gly Gly Gln Gln Met Gly Arg Asp Leu Tyr Asp
             15                  20                  25 gat gac gat aag gat cag ctt gac atg gcg cct aag aag aag agg aag   448
Asp Asp Asp Lys Asp Gln Leu Asp Met Ala Pro Lys Lys Lys Arg Lys
         30                  35                  40 aga tca tat ggt cgt aag aaa cgt cgc caa cgt cgc cga aga tct aac   496
Arg Ser Tyr Gly Arg Lys Lys Arg Arg Gln Arg Arg Arg Arg Ser Asn
     45                  50                  55 cca ttt tct act cag gac aca gat tta gac ttg gag atg tta gct ccc   544
Pro Phe Ser Thr Gln Asp Thr Asp Leu Asp Leu Glu Met Leu Ala Pro
 60                  65                  70                  75 tat atc cca atg gat gat gac ttc cag tta cgt tcc ttc gat cag ttg   592
```

-continued

```
Tyr Ile Pro Met Asp Asp Asp Phe Gln Leu Arg Ser Phe Asp Gln Leu
            80                  85                  90 tca cca tta gaa agc agt tcc gca agc cct gaa agc gca agt cct caa       640
Ser Pro Leu Glu Ser Ser Ser Ala Ser Pro Glu Ser Ala Ser Pro Gln
                95                 100                 105 agc aca gtt aca gta ttc cag cag gta ccg gtg ggt gaa gac cag aaa       688
Ser Thr Val Thr Val Phe Gln Gln Val Pro Val Gly Glu Asp Gln Lys
            110                 115                 120 cag cac ctc gaa ctg agc cgc gat att gcc cag cgt ttc aac gcg ctg       736
Gln His Leu Glu Leu Ser Arg Asp Ile Ala Gln Arg Phe Asn Ala Leu
        125                 130                 135 tat ggc gag atc gat ccc gtc gtt tta caa cgt cgt gac tgg gaa aac       784
Tyr Gly Glu Ile Asp Pro Val Val Leu Gln Arg Arg Asp Trp Glu Asn
140                 145                 150                 155 cct ggc gtt acc caa ctt aat cgc ctt gca gca cat ccc cct ttc gcc       832
Pro Gly Val Thr Gln Leu Asn Arg Leu Ala Ala His Pro Pro Phe Ala
                160                 165                 170 agc tgg cgt aat agc gaa gag gcc cgc acc gat cgc cct tcc caa cag       880
Ser Trp Arg Asn Ser Glu Glu Ala Arg Thr Asp Arg Pro Ser Gln Gln
            175                 180                 185 ttg cgc agc ctg aat ggc gaa tgg cgc ttt gcc tgg ttt ccg gca cca       928
Leu Arg Ser Leu Asn Gly Glu Trp Arg Phe Ala Trp Phe Pro Ala Pro
        190                 195                 200 gaa gcg gtg ccg gaa agc tgg ctg gag tgc gat ctt cct gag gcc gat       976
Glu Ala Val Pro Glu Ser Trp Leu Glu Cys Asp Leu Pro Glu Ala Asp
205                 210                 215 act gtc gtc gtc ccc tca aac tgg cag atg cac ggt tac gat gcg ccc      1024
Thr Val Val Val Pro Ser Asn Trp Gln Met His Gly Tyr Asp Ala Pro
220                 225                 230                 235 atc tac acc aac gta acc tat ccc att acg gtc aat ccg ccg ttt gtt      1072
Ile Tyr Thr Asn Val Thr Tyr Pro Ile Thr Val Asn Pro Pro Phe Val
                240                 245                 250 ccc acg gag aat ccg acg ggt tgt tac tcg ctc aca ttt aat gtt gat      1120
Pro Thr Glu Asn Pro Thr Gly Cys Tyr Ser Leu Thr Phe Asn Val Asp
            255                 260                 265 gaa agc tgg cta cag gaa ggc cag acg cga att att ttt gat ggc gtt      1168
Glu Ser Trp Leu Gln Glu Gly Gln Thr Arg Ile Ile Phe Asp Gly Val
        270                 275                 280 aac tcg gcg ttt cat ctg tgg tgc aac ggg cgc tgg gtc ggt tac ggc      1216
Asn Ser Ala Phe His Leu Trp Cys Asn Gly Arg Trp Val Gly Tyr Gly
285                 290                 295 cag gac agt cgt ttg ccg tct gaa ttt gac ctg agc gca ttt tta cgc      1264
Gln Asp Ser Arg Leu Pro Ser Glu Phe Asp Leu Ser Ala Phe Leu Arg
300                 305                 310                 315 gcc gga gaa aac cgc ctc gcg gtg atg gtg ctg cgt tgg agt gac ggc      1312
Ala Gly Glu Asn Arg Leu Ala Val Met Val Leu Arg Trp Ser Asp Gly
                320                 325                 330 agt tat ctg gaa gat cag gat atg tgg cgg atg agc ggc att ttc cgt      1360
Ser Tyr Leu Glu Asp Gln Asp Met Trp Arg Met Ser Gly Ile Phe Arg
            335                 340                 345 gac gtc tcg ttg ctg cat aaa ccg act aca caa atc agc gat ttc cat      1408
Asp Val Ser Leu Leu His Lys Pro Thr Thr Gln Ile Ser Asp Phe His
        350                 355                 360 gtt gcc act cgc ttt aat gat gat ttc agc cgc gct gta ctg gag gct      1456
Val Ala Thr Arg Phe Asn Asp Asp Phe Ser Arg Ala Val Leu Glu Ala
365                 370                 375 gaa gtt cag atg tgc ggc gag ttg cgt gac tac cta cgg gta aca gtt      1504
Glu Val Gln Met Cys Gly Glu Leu Arg Asp Tyr Leu Arg Val Thr Val
380                 385                 390                 395
```

```
tct tta tgg cag ggt gaa acg cag gtc gcc agc ggc acc gcg cct ttc    1552
Ser Leu Trp Gln Gly Glu Thr Gln Val Ala Ser Gly Thr Ala Pro Phe
            400                 405                 410 ggc ggt gaa att atc gat gag cgt ggt ggt tat gcc gat cgc gtc aca    1600
Gly Gly Glu Ile Ile Asp Glu Arg Gly Gly Tyr Ala Asp Arg Val Thr
        415                 420                 425 cta cgt ctg aac gtc gaa aac ccg aaa ctg tgg agc gcc gaa atc ccg    1648
Leu Arg Leu Asn Val Glu Asn Pro Lys Leu Trp Ser Ala Glu Ile Pro
    430                 435                 440 aat ctc tat cgt gcg gtg gtt gaa ctg cac acc gcc gac ggc acg ctg    1696
Asn Leu Tyr Arg Ala Val Val Glu Leu His Thr Ala Asp Gly Thr Leu
445                 450                 455 att gaa gca gaa gcc tgc gat gtc ggt ttc cgc gag gtg cgg att gaa    1744
Ile Glu Ala Glu Ala Cys Asp Val Gly Phe Arg Glu Val Arg Ile Glu
460                 465                 470                 475 aat ggt ctg ctg ctg ctg aac ggc aag ccg ttg ctg att cga ggc gtt    1792
Asn Gly Leu Leu Leu Leu Asn Gly Lys Pro Leu Leu Ile Arg Gly Val
            480                 485                 490 aac cgt cac gag cat cat cct ctg cat ggt cag gtc atg gat gag cag    1840
Asn Arg His Glu His His Pro Leu His Gly Gln Val Met Asp Glu Gln
        495                 500                 505 acg atg gtg cag gat atc ctg ctg atg aag cag aac aac ttt aac gcc    1888
Thr Met Val Gln Asp Ile Leu Leu Met Lys Gln Asn Asn Phe Asn Ala
    510                 515                 520 gtg cgc tgt tcg cat tat ccg aac cat ccg ctg tgg tac acg ctg tgc    1936
Val Arg Cys Ser His Tyr Pro Asn His Pro Leu Trp Tyr Thr Leu Cys
525                 530                 535 gac cgc tac ggc ctg tat gtg gtg gat gaa gcc aat att gaa acc cac    1984
Asp Arg Tyr Gly Leu Tyr Val Val Asp Glu Ala Asn Ile Glu Thr His
540                 545                 550                 555 ggc atg gtg cca atg aat cgt ctg acc gat gat ccg cgc tgg cta ccg    2032
Gly Met Val Pro Met Asn Arg Leu Thr Asp Asp Pro Arg Trp Leu Pro
            560                 565                 570 gcg atg agc gaa cgt gta acg cga atg gtg cag cgc gat cgt aat cac    2080
Ala Met Ser Glu Arg Val Thr Arg Met Val Gln Arg Asp Arg Asn His
        575                 580                 585 ccg agt gtg atc atc tgg tcg ctg ggg aat gaa tca ggc cac ggc gct    2128
Pro Ser Val Ile Ile Trp Ser Leu Gly Asn Glu Ser Gly His Gly Ala
    590                 595                 600 aat cac gac gcg ctg tat cgc tgg atc aaa tct gtc gat cct tcc cgc    2176
Asn His Asp Ala Leu Tyr Arg Trp Ile Lys Ser Val Asp Pro Ser Arg
605                 610                 615 ccg gtg cag tat gaa ggc ggc gga gcc gac acc acg gcc acc gat att    2224
Pro Val Gln Tyr Glu Gly Gly Gly Ala Asp Thr Thr Ala Thr Asp Ile
620                 625                 630                 635 att tgc ccg atg tac gcg cgc gtg gat gaa gac cag ccc ttc ccg gct    2272
Ile Cys Pro Met Tyr Ala Arg Val Asp Glu Asp Gln Pro Phe Pro Ala
            640                 645                 650 gtg ccg aaa tgg tcc atc aaa aaa tgg ctt tcg cta cct gga gag acg    2320
Val Pro Lys Trp Ser Ile Lys Lys Trp Leu Ser Leu Pro Gly Glu Thr
        655                 660                 665 cgc ccg ctg atc ctt tgc gaa tac gcc cac gcg atg ggt aac agt ctt    2368
Arg Pro Leu Ile Leu Cys Glu Tyr Ala His Ala Met Gly Asn Ser Leu
    670                 675                 680 ggc ggt ttc gct aaa tac tgg cag gcg ttt cgt cag tat ccc cgt tta    2416
Gly Gly Phe Ala Lys Tyr Trp Gln Ala Phe Arg Gln Tyr Pro Arg Leu
685                 690                 695 cag ggc ggc ttc gtc tgg gac tgg gtg gat cag tcg ctg att aaa tat    2464
Gln Gly Gly Phe Val Trp Asp Trp Val Asp Gln Ser Leu Ile Lys Tyr
700                 705                 710                 715
```

```
gat gaa aac ggc aac ccg tgg tcg gct tac ggc ggt gat ttt ggc gat    2512
Asp Glu Asn Gly Asn Pro Trp Ser Ala Tyr Gly Gly Asp Phe Gly Asp
            720                 725                 730 acg ccg aac gat cgc cag ttc tgt atg aac ggt ctg gtc ttt gcc gac    2560
Thr Pro Asn Asp Arg Gln Phe Cys Met Asn Gly Leu Val Phe Ala Asp
        735                 740                 745 cgc acg ccg cat cca gcg ctg acg gaa gca aaa cac cag cag cag ttt    2608
Arg Thr Pro His Pro Ala Leu Thr Glu Ala Lys His Gln Gln Gln Phe
    750                 755                 760 ttc cag ttc cgt tta tcc ggg caa acc atc gaa gtg acc agc gaa tac    2656
Phe Gln Phe Arg Leu Ser Gly Gln Thr Ile Glu Val Thr Ser Glu Tyr
765                 770                 775 ctg ttc cgt cat agc gat aac gag ctc ctg cac tgg atg gtg gcg ctg    2704
Leu Phe Arg His Ser Asp Asn Glu Leu Leu His Trp Met Val Ala Leu
780                 785                 790                 795 gat ggt aag ccg ctg gca agc ggt gaa gtg cct ctg gat gtc gct cca    2752
Asp Gly Lys Pro Leu Ala Ser Gly Glu Val Pro Leu Asp Val Ala Pro
                800                 805                 810 caa ggt aaa cag ttg att gaa ctg cct gaa cta ccg cag ccg gag agc    2800
Gln Gly Lys Gln Leu Ile Glu Leu Pro Glu Leu Pro Gln Pro Glu Ser
            815                 820                 825 gcc ggg caa ctc tgg ctc aca gta cgc gta gtg caa ccg aac gcg acc    2848
Ala Gly Gln Leu Trp Leu Thr Val Arg Val Val Gln Pro Asn Ala Thr
        830                 835                 840 gca tgg tca gaa gcc ggg cac atc agc gcc tgg cag cag tgg cgt ctg    2896
Ala Trp Ser Glu Ala Gly His Ile Ser Ala Trp Gln Gln Trp Arg Leu
    845                 850                 855 gcg gaa aac ctc agt gtg acg ctc ccc gcc gcg tcc cac gcc atc ccg    2944
Ala Glu Asn Leu Ser Val Thr Leu Pro Ala Ala Ser His Ala Ile Pro
860                 865                 870                 875 cat ctg acc acc agc gaa atg gat ttt tgc atc gag ctg ggt aat aag    2992
His Leu Thr Thr Ser Glu Met Asp Phe Cys Ile Glu Leu Gly Asn Lys
                880                 885                 890 cgt tgg caa ttt aac cgc cag tca ggc ttt ctt tca cag atg tgg att    3040
Arg Trp Gln Phe Asn Arg Gln Ser Gly Phe Leu Ser Gln Met Trp Ile
            895                 900                 905 ggc gat aaa aaa caa ctg ctg acg ccg ctg cgc gat cag ttc acc cgt    3088
Gly Asp Lys Lys Gln Leu Leu Thr Pro Leu Arg Asp Gln Phe Thr Arg
        910                 915                 920 gca ccg ctg gat aac gac att ggc gta agt gaa gcg acc cgc att gac    3136
Ala Pro Leu Asp Asn Asp Ile Gly Val Ser Glu Ala Thr Arg Ile Asp
    925                 930                 935 cct aac gcc tgg gtc gaa cgc tgg aag gcg gcg ggc cat tac cag gcc    3184
Pro Asn Ala Trp Val Glu Arg Trp Lys Ala Ala Gly His Tyr Gln Ala
940                 945                 950                 955 gaa gca gcg ttg ttg cag tgc acg gca gat aca ctt gct gat gcg gtg    3232
Glu Ala Ala Leu Leu Gln Cys Thr Ala Asp Thr Leu Ala Asp Ala Val
                960                 965                 970 ctg att acg acc gct cac gcg tgg cag cat cag ggg aaa acc tta ttt    3280
Leu Ile Thr Thr Ala His Ala Trp Gln His Gln Gly Lys Thr Leu Phe
            975                 980                 985 atc agc cgg aaa acc tac cgg att gat ggt agt ggt caa atg gcg att    3328
Ile Ser Arg Lys Thr Tyr Arg Ile Asp Gly Ser Gly Gln Met Ala Ile
        990                 995                 1000 acc gtt gat gtt gaa gtg gcg agc gat aca ccg cat ccg gcg cgg att    3376
Thr Val Asp Val Glu Val Ala Ser Asp Thr Pro His Pro Ala Arg Ile
    1005                1010                1015 ggc ctg aac tgc cag ctg gcg cag gta gca gag cgg gta aac tgg ctc    3424
Gly Leu Asn Cys Gln Leu Ala Gln Val Ala Glu Arg Val Asn Trp Leu
```

-continued

|     |     |     |     |     |     |     |     |     |     |     |     |     |     |     |     |     |
|---|---|---|---|---|---|---|---|---|---|---|---|---|---|---|---|---|
| 1020 | | | | | 1025 | | | | | 1030 | | | | | 1035 | |

```
gga tta ggg ccg caa gaa aac tat ccc gac cgc ctt act gcc gcc tgt      3472
Gly Leu Gly Pro Gln Glu Asn Tyr Pro Asp Arg Leu Thr Ala Ala Cys
            1040                1045                1050 ttt gac cgc tgg gat ctg cca ttg tca gac atg tat acc ccg tac gtc      3520
Phe Asp Arg Trp Asp Leu Pro Leu Ser Asp Met Tyr Thr Pro Tyr Val
        1055                1060                1065 ttc ccg agc gaa aac ggt ctg cgc tgc ggg acg cgc gaa ttg aat tat      3568
Phe Pro Ser Glu Asn Gly Leu Arg Cys Gly Thr Arg Glu Leu Asn Tyr
    1070                1075                1080 ggc cca cac cag tgg cgc ggc gac ttc cag ttc aac atc agc cgc tac      3616
Gly Pro His Gln Trp Arg Gly Asp Phe Gln Phe Asn Ile Ser Arg Tyr
  1085                1090                1095 agt caa cag caa ctg atg gaa acc agc cat cgc cat ctg ctg cac gcg      3664
Ser Gln Gln Gln Leu Met Glu Thr Ser His Arg His Leu Leu His Ala
1100                1105                1110                1115 gaa gaa ggc aca tgg ctg aat atc gac ggt ttc cat atg ggg att ggt      3712
Glu Glu Gly Thr Trp Leu Asn Ile Asp Gly Phe His Met Gly Ile Gly
            1120                1125                1130 ggc gac gac tcc tgg agc ccg tca gta tcg gcg gaa ttc cag ctg agc      3760
Gly Asp Asp Ser Trp Ser Pro Ser Val Ser Ala Glu Phe Gln Leu Ser
        1135                1140                1145 gcc ggt cgc tac cat tac cag ttg gtc tgg tgt caa aaa taagcttggc      3809
Ala Gly Arg Tyr His Tyr Gln Leu Val Trp Cys Gln Lys
    1150                1155                1160
```

|  |  |
|---|---|
| tgttttggcg atgagagaaa gattttcagc ctgatacaga ttaaatcaga acgcagaagc | 3869 |
| ggtctgataa aacagaattt gcctggcggc agtagcgcgg tggtcccacc tgaccccatg | 3929 |
| ccgaactcag aagtgaaacg ccgtagcgcc gatggtagtg tggggtctcc ccatgcgaga | 3989 |
| gtagggaact gccaggcatc aaataaaacg aaaggctcag tcgaaagact gggcctttcg | 4049 |
| ttttatctgt tgtttgtcgg tgaacgctct cctgagtagg acaaatccgc cgggagcgga | 4109 |
| tttgaacgtt gcgaagcaac ggcccggagg gtggcgggca ggacgcccgc cataaactgc | 4169 |
| caggcatcaa attaagcaga aggccatcct gacggatggc cttttttgcgt ttctacaaac | 4229 |
| tcttttttgtt tattttttcta aatacattca aatatgtatc cgctcatgag acaataaccc | 4289 |
| tgataaatgc ttcaataata ttgaaaaagg aagagtatga gtattcaaca tttccgtgtc | 4349 |
| gcccttattc ccttttttgc ggcattttgc cttcctgttt ttgctcaccc agaaacgctg | 4409 |
| gtgaaagtaa aagatgctga agatcagttg ggtgcacgag tgggttacat cgaactggat | 4469 |
| ctcaacagcg gtaagatcct tgagagtttt cgccccgaag aacgttttcc aatgatgagc | 4529 |
| acttttaaag ttctgctatg tggcgcggta ttatcccgtg ttgacgccgg gcaagagcaa | 4589 |
| ctcggtcgcc gcatacacta ttctcagaat gacttggttg agtactcacc agtcacagaa | 4649 |
| aagcatctta cggatggcat gacagtaaga gaattatgca gtgctgccat aaccatgagt | 4709 |
| gataacactg cggccaactt acttctgaca acgatcggag gaccgaagga gctaaccgct | 4769 |
| tttttgcaca acatggggga tcatgtaact cgccttgatc gttgggaacc ggagctgaat | 4829 |
| gaagccatac caaacgacga gcgtgacacc acgatgcctg tagcaatggc aacaacgttg | 4889 |
| cgcaaactat taactggcga actacttact ctagcttccc ggcaacaatt aatagactgg | 4949 |
| atggaggcgg ataaagttgc aggaccactt ctgcgctcgg cccttccggc tggctggttt | 5009 |
| attgctgata aatctggagc cggtgagcgt gggtctcgcg gtatcattgc agcactgggg | 5069 |
| ccagatggta agccctcccg tatcgtagtt atctacacga cggggagtca ggcaactatg | 5129 |
| gatgaacgaa atagacagat cgctgagata ggtgcctcac tgattaagca ttggtaactg | 5189 |

```
tcagaccaag tttactcata tatactttag attgatttaa aacttcattt ttaatttaaa    5249
aggatctagg tgaagatcct ttttgataat ctcatgacca aaatccctta acgtgagttt    5309
tcgttccact gagcgtcaga ccccgtagaa aagatcaaag gatcttcttg agatcctttt    5369
tttctgcgcg taatctgctg cttgcaaaca aaaaaaccac cgctaccagc ggtggtttgt    5429
ttgccggatc aagagctacc aactctttt ccgaaggtaa ctggcttcag cagagcgcag    5489
ataccaaata ctgtccttct agtgtagccg tagttaggcc accacttcaa gaactctgta    5549
gcaccgccta catacctcgc tctgctaatc ctgttaccag tggctgctgc cagtggcgat    5609
aagtcgtgtc ttaccgggtt ggactcaaga cgatagttac cggataaggc gcagcggtcg    5669
ggctgaacgg ggggttcgtg cacacagccc agcttggagc gaacgaccta caccgaactg    5729
agatacctac agcgtgagct atgagaaagc gccacgcttc ccgaagggag aaaggcggac    5789
aggtatccgg taagcggcag ggtcggaaca ggagagcgca cgagggagct tccaggggga    5849
aacgcctggt atctttatag tcctgtcggg tttcgccacc tctgacttga gcgtcgattt    5909
ttgtgatgct cgtcaggggg gcggagccta tggaaaaacg ccagcaacgc ggccttttta    5969
cggttcctgg ccttttgctg gccttttgct cacatgttct ttcctgcgtt atccctgat    6029
tctgtggata accgtattac cgcctttgag tgagctgata ccgctcgccg cagccgaacg    6089
accgagcgca gcgagtcagt gagcgaggaa gcggaagagc gcctgatgcg gtattttctc    6149
cttacgcatc tgtgcggtat ttcacaccgc atatggtgca ctctcagtac aatctgctct    6209
gatgccgcat agttaagcca gtatacactc cgctatcgct acgtgactgg gtcatggctg    6269
cgccccgaca cccgccaaca cccgctgacg cgccctgacg ggcttgtctg ctcccggcat    6329
ccgcttacag acaagctgtg accgtctccg ggagctgcat gtgtcagagg ttttcaccgt    6389
catcaccgaa acgcgcgagg cagcagatca attcgcgcgc gaaggcgaag cggcatgcat    6449
aatgtgcctg tcaaatggac gaagcaggga ttctgcaaac cctatgctac tccgtcaagc    6509
cgtcaattgt ctgattcgtt accaattatg acaacttgac ggctacatca ttcactttt    6569
cttcacaacc ggcacggaac tcgctcgggc tggccccgt gcattttta atacccgcg     6629
agaaatagag ttgatcgtca aaaccaacat tgcgaccgac ggtggcgata ggcatccggg    6689
tggtgctcaa aagcagcttc gcctggctga tacgttggtc ctcgcgccag cttaagacgc    6749
taatccctaa ctgctggcgg aaaagatgtg acagacgcga cggcgacaag caaacatgct    6809
gtgcgacgct ggcgatatca aaattgctgt ctgccaggtg atcgctgatg tactgacaag    6869
cctcgcgtac ccgattatcc atcggtggat ggagcgactc gttaatcgct tccatgcgcc    6929
gcagtaacaa ttgctcaagc agatttatcg ccagcagctc cgaatagcgc ccttcccctt    6989
gcccggcgtt aatgatttgc ccaaacaggt cgctgaaatg cggctggtgc gcttcatccg    7049
ggcgaaagaa ccccgtattg gcaaatattg acggccagtt aagccattca tgccagtagg    7109
cgcgcggacg aaagtaaacc cactggtgat accattcgcg agcctccgga tgacgaccgt    7169
agtgatgaat ctctcctggc gggaacagca aaatatcacc cggtcggcaa acaaattctc    7229
gtccctgatt tttcaccacc ccctgaccgc gaatggtgag attgagaata taacctttca    7289
ttcccagcgg tcggtcgata aaaaaatcga gataaccgtt ggcctcaatc ggcgttaaac    7349
ccgccaccag atgggcatta aacgagtatc ccggcagcag gggatcattt tgcgcttcag    7409
ccatactttt catactcccg ccattcagag                                   7439
```

<210> SEQ ID NO 43

-continued

```
<211> LENGTH: 1160
<212> TYPE: PRT
<213> ORGANISM: Artificial Sequence
<220> FEATURE:
<223> OTHER INFORMATION: Description of Artificial Sequence: fusion
      protein comprising a poly-histidine region, a nuclear
      localization signal from SV40 large T antigen, a TAT signal
      sequence from HIV, a region of the human HIF-1alpha gene, and the
      Beta-galactosidase protein from E. coli.

<400> SEQUENCE: 43

Met Gly Gly Ser His His His His His Gly Met Ala Ser Met Thr
 1               5                  10                  15

Gly Gly Gln Gln Met Gly Arg Asp Leu Tyr Asp Asp Asp Lys Asp
                20                  25                  30

Gln Leu Asp Met Ala Pro Lys Lys Arg Lys Arg Ser Tyr Gly Arg
            35                  40                  45

Lys Lys Arg Arg Gln Arg Arg Arg Ser Asn Pro Phe Ser Thr Gln
 50                  55                  60

Asp Thr Asp Leu Asp Leu Glu Met Leu Ala Pro Tyr Ile Pro Met Asp
 65                  70                  75                  80

Asp Asp Phe Gln Leu Arg Ser Phe Asp Gln Leu Ser Pro Leu Glu Ser
                85                  90                  95

Ser Ser Ala Ser Pro Glu Ser Ala Ser Pro Gln Ser Thr Val Thr Val
            100                 105                 110

Phe Gln Gln Val Pro Val Gly Glu Asp Gln Lys Gln His Leu Glu Leu
        115                 120                 125

Ser Arg Asp Ile Ala Gln Arg Phe Asn Ala Leu Tyr Gly Glu Ile Asp
    130                 135                 140

Pro Val Val Leu Gln Arg Arg Asp Trp Glu Asn Pro Gly Val Thr Gln
145                 150                 155                 160

Leu Asn Arg Leu Ala Ala His Pro Pro Phe Ala Ser Trp Arg Asn Ser
                165                 170                 175

Glu Glu Ala Arg Thr Asp Arg Pro Ser Gln Gln Leu Arg Ser Leu Asn
            180                 185                 190

Gly Glu Trp Arg Phe Ala Trp Phe Pro Ala Pro Glu Ala Val Pro Glu
        195                 200                 205

Ser Trp Leu Glu Cys Asp Leu Pro Glu Ala Asp Thr Val Val Pro
    210                 215                 220

Ser Asn Trp Gln Met His Gly Tyr Asp Ala Pro Ile Tyr Thr Asn Val
225                 230                 235                 240

Thr Tyr Pro Ile Thr Val Asn Pro Pro Phe Val Pro Thr Glu Asn Pro
                245                 250                 255

Thr Gly Cys Tyr Ser Leu Thr Phe Asn Val Asp Glu Ser Trp Leu Gln
            260                 265                 270

Glu Gly Gln Thr Arg Ile Ile Phe Asp Gly Val Asn Ser Ala Phe His
        275                 280                 285

Leu Trp Cys Asn Gly Arg Trp Val Gly Tyr Gly Gln Asp Ser Arg Leu
    290                 295                 300

Pro Ser Glu Phe Asp Leu Ser Ala Phe Leu Arg Ala Gly Glu Asn Arg
305                 310                 315                 320

Leu Ala Val Met Val Leu Arg Trp Ser Asp Gly Ser Tyr Leu Glu Asp
                325                 330                 335

Gln Asp Met Trp Arg Met Ser Gly Ile Phe Arg Asp Val Ser Leu Leu
            340                 345                 350

His Lys Pro Thr Thr Gln Ile Ser Asp Phe His Val Ala Thr Arg Phe
```

-continued

```
                355                 360                 365
Asn Asp Asp Phe Ser Arg Ala Val Leu Glu Ala Glu Val Gln Met Cys
370                 375                 380

Gly Glu Leu Arg Asp Tyr Leu Arg Val Thr Val Ser Leu Trp Gln Gly
385                 390                 395                 400

Glu Thr Gln Val Ala Ser Gly Thr Ala Pro Phe Gly Gly Glu Ile Ile
                405                 410                 415

Asp Glu Arg Gly Gly Tyr Ala Asp Arg Val Thr Leu Arg Leu Asn Val
                420                 425                 430

Glu Asn Pro Lys Leu Trp Ser Ala Glu Ile Pro Asn Leu Tyr Arg Ala
            435                 440                 445

Val Val Glu Leu His Thr Ala Asp Gly Thr Leu Ile Glu Ala Glu Ala
450                 455                 460

Cys Asp Val Gly Phe Arg Glu Val Arg Ile Glu Asn Gly Leu Leu Leu
465                 470                 475                 480

Leu Asn Gly Lys Pro Leu Leu Ile Arg Gly Val Asn Arg His Glu His
                485                 490                 495

His Pro Leu His Gly Gln Val Met Asp Glu Gln Thr Met Val Gln Asp
            500                 505                 510

Ile Leu Leu Met Lys Gln Asn Asn Phe Asn Ala Val Arg Cys Ser His
            515                 520                 525

Tyr Pro Asn His Pro Leu Trp Tyr Thr Leu Cys Asp Arg Tyr Gly Leu
530                 535                 540

Tyr Val Val Asp Glu Ala Asn Ile Glu Thr His Gly Met Val Pro Met
545                 550                 555                 560

Asn Arg Leu Thr Asp Asp Pro Arg Trp Leu Pro Ala Met Ser Glu Arg
                565                 570                 575

Val Thr Arg Met Val Gln Arg Asp Arg Asn His Pro Ser Val Ile Ile
            580                 585                 590

Trp Ser Leu Gly Asn Glu Ser Gly His Gly Ala Asn His Asp Ala Leu
            595                 600                 605

Tyr Arg Trp Ile Lys Ser Val Asp Pro Ser Arg Pro Val Gln Tyr Glu
610                 615                 620

Gly Gly Gly Ala Asp Thr Thr Ala Thr Asp Ile Ile Cys Pro Met Tyr
625                 630                 635                 640

Ala Arg Val Asp Glu Asp Gln Pro Phe Pro Ala Val Pro Lys Trp Ser
                645                 650                 655

Ile Lys Lys Trp Leu Ser Leu Pro Gly Glu Thr Arg Pro Leu Ile Leu
            660                 665                 670

Cys Glu Tyr Ala His Ala Met Gly Asn Ser Leu Gly Gly Phe Ala Lys
            675                 680                 685

Tyr Trp Gln Ala Phe Arg Gln Tyr Pro Arg Leu Gln Gly Gly Phe Val
690                 695                 700

Trp Asp Trp Val Asp Gln Ser Leu Ile Lys Tyr Asp Glu Asn Gly Asn
705                 710                 715                 720

Pro Trp Ser Ala Tyr Gly Gly Asp Phe Gly Asp Thr Pro Asn Asp Arg
                725                 730                 735

Gln Phe Cys Met Asn Gly Leu Val Phe Ala Asp Arg Thr Pro His Pro
            740                 745                 750

Ala Leu Thr Glu Ala Lys His Gln Gln Gln Phe Phe Gln Phe Arg Leu
            755                 760                 765

Ser Gly Gln Thr Ile Glu Val Thr Ser Glu Tyr Leu Phe Arg His Ser
770                 775                 780
```

```
Asp Asn Glu Leu Leu His Trp Met Val Ala Leu Asp Gly Lys Pro Leu
785                 790                 795                 800

Ala Ser Gly Glu Val Pro Leu Asp Val Ala Pro Gln Gly Lys Gln Leu
            805                 810                 815

Ile Glu Leu Pro Glu Leu Pro Gln Pro Glu Ser Ala Gly Gln Leu Trp
        820                 825                 830

Leu Thr Val Arg Val Val Gln Pro Asn Ala Thr Ala Trp Ser Glu Ala
    835                 840                 845

Gly His Ile Ser Ala Trp Gln Gln Trp Arg Leu Ala Glu Asn Leu Ser
850                 855                 860

Val Thr Leu Pro Ala Ala Ser His Ala Ile Pro His Leu Thr Thr Ser
865                 870                 875                 880

Glu Met Asp Phe Cys Ile Glu Leu Gly Asn Lys Arg Trp Gln Phe Asn
                885                 890                 895

Arg Gln Ser Gly Phe Leu Ser Gln Met Trp Ile Gly Asp Lys Lys Gln
            900                 905                 910

Leu Leu Thr Pro Leu Arg Asp Gln Phe Thr Arg Ala Pro Leu Asp Asn
        915                 920                 925

Asp Ile Gly Val Ser Glu Ala Thr Arg Ile Asp Pro Asn Ala Trp Val
    930                 935                 940

Glu Arg Trp Lys Ala Ala Gly His Tyr Gln Ala Glu Ala Ala Leu Leu
945                 950                 955                 960

Gln Cys Thr Ala Asp Thr Leu Ala Asp Ala Val Leu Ile Thr Thr Ala
                965                 970                 975

His Ala Trp Gln His Gln Gly Lys Thr Leu Phe Ile Ser Arg Lys Thr
            980                 985                 990

Tyr Arg Ile Asp Gly Ser Gly Gln Met Ala Ile Thr Val Asp Val Glu
        995                 1000                1005

Val Ala Ser Asp Thr Pro His Pro Ala Arg Ile Gly Leu Asn Cys Gln
    1010                1015                1020

Leu Ala Gln Val Ala Glu Arg Val Asn Trp Leu Gly Leu Gly Pro Gln
1025                1030                1035                1040

Glu Asn Tyr Pro Asp Arg Leu Thr Ala Ala Cys Phe Asp Arg Trp Asp
                1045                1050                1055

Leu Pro Leu Ser Asp Met Tyr Thr Pro Tyr Val Phe Pro Ser Glu Asn
            1060                1065                1070

Gly Leu Arg Cys Gly Thr Arg Glu Leu Asn Tyr Gly Pro His Gln Trp
        1075                1080                1085

Arg Gly Asp Phe Gln Phe Asn Ile Ser Arg Tyr Ser Gln Gln Gln Leu
    1090                1095                1100

Met Glu Thr Ser His Arg His Leu Leu His Ala Glu Glu Gly Thr Trp
1105                1110                1115                1120

Leu Asn Ile Asp Gly Phe His Met Gly Ile Gly Gly Asp Asp Ser Trp
                1125                1130                1135

Ser Pro Ser Val Ser Ala Glu Phe Gln Leu Ser Ala Gly Arg Tyr His
            1140                1145                1150

Tyr Gln Leu Val Trp Cys Gln Lys
        1155                1160

<210> SEQ ID NO 44
<211> LENGTH: 7325
<212> TYPE: DNA
<213> ORGANISM: Artificial Sequence
<220> FEATURE:
```

<223> OTHER INFORMATION: Description of Artificial Sequence: fusion gene of 00 and 11
<220> FEATURE:
<221> NAME/KEY: CDS
<222> LOCATION: (320)..(3685)

<400> SEQUENCE: 44

```
aagaaaccaa ttgtccatat tgcatcagac attgccgtca ctgcgtcttt tactggctct      60
tctcgctaac caaaccggta accccgctta ttaaaagcat tctgtaacaa agcgggacca     120
aagccatgac aaaaacgcgt aacaaaagtg tctataatca cggcagaaaa gtccacattg     180
attatttgca cggcgtcaca ctttgctatg ccatagcatt tttatccata agattagcgg     240
atcctacctg acgcttttta tcgcaactct ctactgtttc tccatacccg ttttttgggg     300
ctaacaggag gaattaacc atg ggg ggt tct cat cat cat cat cat cat ggt     352
                     Met Gly Gly Ser His His His His His His Gly
                      1               5                  10 atg gct agc atg act ggt gga cag caa atg ggt cgg gat ctg tac gac      400
Met Ala Ser Met Thr Gly Gly Gln Gln Met Gly Arg Asp Leu Tyr Asp
             15                  20                  25 gat gac gat aag gat cag ctt gac atg gcg cct aag aag aag agg aag      448
Asp Asp Asp Lys Asp Gln Leu Asp Met Ala Pro Lys Lys Lys Arg Lys
         30                  35                  40 aga tca tat ggt cgt aag aaa cgt cgc caa cgt cgc cga aga tct tta      496
Arg Ser Tyr Gly Arg Lys Lys Arg Arg Gln Arg Arg Arg Arg Ser Leu
 45                  50                  55 gac ttg gag atg tta gct ccc tat atc cca atg gat gat gac ttc cag      544
Asp Leu Glu Met Leu Ala Pro Tyr Ile Pro Met Asp Asp Asp Phe Gln
 60                  65                  70                  75 tta cag gta ccg gtg ggt gaa gac cag aaa cag cac ctc gaa ctg agc      592
Leu Gln Val Pro Val Gly Glu Asp Gln Lys Gln His Leu Glu Leu Ser
             80                  85                  90 cgc gat att gcc cag cgt ttc aac gcg ctg tat ggc gag atc gat ccc      640
Arg Asp Ile Ala Gln Arg Phe Asn Ala Leu Tyr Gly Glu Ile Asp Pro
             95                 100                 105 gtc gtt tta caa cgt cgt gac tgg gaa aac cct ggc gtt acc caa ctt      688
Val Val Leu Gln Arg Arg Asp Trp Glu Asn Pro Gly Val Thr Gln Leu
    110                 115                 120 aat cgc ctt gca gca cat ccc cct ttc gcc agc tgg cgt aat agc gaa      736
Asn Arg Leu Ala Ala His Pro Pro Phe Ala Ser Trp Arg Asn Ser Glu
125                 130                 135 gag gcc cgc acc gat cgc cct tcc caa cag ttg cgc agc ctg aat ggc      784
Glu Ala Arg Thr Asp Arg Pro Ser Gln Gln Leu Arg Ser Leu Asn Gly
140                 145                 150                 155 gaa tgg cgc ttt gcc tgg ttt ccg gca cca gaa gcg gtg ccg gaa agc      832
Glu Trp Arg Phe Ala Trp Phe Pro Ala Pro Glu Ala Val Pro Glu Ser
                160                 165                 170 tgg ctg gag tgc gat ctt cct gag gcc gat act gtc gtc gtc ccc tca      880
Trp Leu Glu Cys Asp Leu Pro Glu Ala Asp Thr Val Val Val Pro Ser
            175                 180                 185 aac tgg cag atg cac ggt tac gat gcg ccc atc tac acc aac gta acc      928
Asn Trp Gln Met His Gly Tyr Asp Ala Pro Ile Tyr Thr Asn Val Thr
            190                 195                 200 tat ccc att acg gtc aat ccg ccg ttt gtt ccc acg gag aat ccg acg      976
Tyr Pro Ile Thr Val Asn Pro Pro Phe Val Pro Thr Glu Asn Pro Thr
205                 210                 215 ggt tgt tac tcg ctc aca ttt aat gtt gat gaa agc tgg cta cag gaa     1024
Gly Cys Tyr Ser Leu Thr Phe Asn Val Asp Glu Ser Trp Leu Gln Glu
220                 225                 230                 235 ggc cag acg cga att att ttt gat ggc gtt aac tcg gcg ttt cat ctg     1072
```

```
Gly Gln Thr Arg Ile Ile Phe Asp Gly Val Asn Ser Ala Phe His Leu
                240                 245                 250 tgg tgc aac ggg cgc tgg gtc ggt tac ggc cag gac agt cgt ttg ccg      1120
Trp Cys Asn Gly Arg Trp Val Gly Tyr Gly Gln Asp Ser Arg Leu Pro
            255                 260                 265 tct gaa ttt gac ctg agc gca ttt tta cgc gcc gga gaa aac cgc ctc      1168
Ser Glu Phe Asp Leu Ser Ala Phe Leu Arg Ala Gly Glu Asn Arg Leu
        270                 275                 280 gcg gtg atg gtg ctg cgt tgg agt gac ggc agt tat ctg gaa gat cag      1216
Ala Val Met Val Leu Arg Trp Ser Asp Gly Ser Tyr Leu Glu Asp Gln
    285                 290                 295 gat atg tgg cgg atg agc ggc att ttc cgt gac gtc tcg ttg ctg cat      1264
Asp Met Trp Arg Met Ser Gly Ile Phe Arg Asp Val Ser Leu Leu His
300                 305                 310                 315 aaa ccg act aca caa atc agc gat ttc cat gtt gcc act cgc ttt aat      1312
Lys Pro Thr Thr Gln Ile Ser Asp Phe His Val Ala Thr Arg Phe Asn
                320                 325                 330 gat gat ttc agc cgc gct gta ctg gag gct gaa gtt cag atg tgc ggc      1360
Asp Asp Phe Ser Arg Ala Val Leu Glu Ala Glu Val Gln Met Cys Gly
            335                 340                 345 gag ttg cgt gac tac cta cgg gta aca gtt tct tta tgg cag ggt gaa      1408
Glu Leu Arg Asp Tyr Leu Arg Val Thr Val Ser Leu Trp Gln Gly Glu
        350                 355                 360 acg cag gtc gcc agc ggc acc gcg cct ttc ggc ggt gaa att atc gat      1456
Thr Gln Val Ala Ser Gly Thr Ala Pro Phe Gly Gly Glu Ile Ile Asp
    365                 370                 375 gag cgt ggt ggt tat gcc gat cgc gtc aca cta cgt ctg aac gtc gaa      1504
Glu Arg Gly Gly Tyr Ala Asp Arg Val Thr Leu Arg Leu Asn Val Glu
380                 385                 390                 395 aac ccg aaa ctg tgg agc gcc gaa atc ccg aat ctc tat cgt gcg gtg      1552
Asn Pro Lys Leu Trp Ser Ala Glu Ile Pro Asn Leu Tyr Arg Ala Val
                400                 405                 410 gtt gaa ctg cac acc gcc gac ggc acg ctg att gaa gca gaa gcc tgc      1600
Val Glu Leu His Thr Ala Asp Gly Thr Leu Ile Glu Ala Glu Ala Cys
            415                 420                 425 gat gtc ggt ttc cgc gag gtg cgg att gaa aat ggt ctg ctg ctg ctg      1648
Asp Val Gly Phe Arg Glu Val Arg Ile Glu Asn Gly Leu Leu Leu Leu
        430                 435                 440 aac ggc aag ccg ttg ctg att cga ggc gtt aac cgt cac gag cat cat      1696
Asn Gly Lys Pro Leu Leu Ile Arg Gly Val Asn Arg His Glu His His
    445                 450                 455 cct ctg cat ggt cag gtc atg gat gag cag acg atg gtg cag gat atc      1744
Pro Leu His Gly Gln Val Met Asp Glu Gln Thr Met Val Gln Asp Ile
460                 465                 470                 475 ctg ctg atg aag cag aac aac ttt aac gcc gtg cgc tgt tcg cat tat      1792
Leu Leu Met Lys Gln Asn Asn Phe Asn Ala Val Arg Cys Ser His Tyr
                480                 485                 490 ccg aac cat ccg ctg tgg tac acg ctg tgc gac cgc tac ggc ctg tat      1840
Pro Asn His Pro Leu Trp Tyr Thr Leu Cys Asp Arg Tyr Gly Leu Tyr
            495                 500                 505 gtg gtg gat gaa gcc aat att gaa acc cac ggc atg gtg cca atg aat      1888
Val Val Asp Glu Ala Asn Ile Glu Thr His Gly Met Val Pro Met Asn
        510                 515                 520 cgt ctg acc gat gat ccg cgc tgg cta ccg gcg atg agc gaa cgc gta      1936
Arg Leu Thr Asp Asp Pro Arg Trp Leu Pro Ala Met Ser Glu Arg Val
    525                 530                 535 acg cga atg gtg cag cgc gat cgt aat cac ccg agt gtg atc atc tgg      1984
Thr Arg Met Val Gln Arg Asp Arg Asn His Pro Ser Val Ile Ile Trp
540                 545                 550                 555
```

```
                                           -continued
tcg ctg ggg aat gaa tca ggc cac ggc gct aat cac gac gcg ctg tat      2032
Ser Leu Gly Asn Glu Ser Gly His Gly Ala Asn His Asp Ala Leu Tyr
            560                 565                 570 cgc tgg atc aaa tct gtc gat cct tcc cgc ccg gtg cag tat gaa ggc      2080
Arg Trp Ile Lys Ser Val Asp Pro Ser Arg Pro Val Gln Tyr Glu Gly
        575                 580                 585 ggc gga gcc gac acc acg gcc acc gat att att tgc ccg atg tac gcg      2128
Gly Gly Ala Asp Thr Thr Ala Thr Asp Ile Ile Cys Pro Met Tyr Ala
    590                 595                 600 cgc gtg gat gaa gac cag ccc ttc ccg gct gtg ccg aaa tgg tcc atc      2176
Arg Val Asp Glu Asp Gln Pro Phe Pro Ala Val Pro Lys Trp Ser Ile
605                 610                 615 aaa aaa tgg ctt tcg cta cct gga gag acg cgc ccg ctg atc ctt tgc      2224
Lys Lys Trp Leu Ser Leu Pro Gly Glu Thr Arg Pro Leu Ile Leu Cys
620                 625                 630                 635 gaa tac gcc cac gcg atg ggt aac agt ctt ggc ggt ttc gct aaa tac      2272
Glu Tyr Ala His Ala Met Gly Asn Ser Leu Gly Gly Phe Ala Lys Tyr
            640                 645                 650 tgg cag gcg ttt cgt cag tat ccc cgt tta cag ggc ggc ttc gtc tgg      2320
Trp Gln Ala Phe Arg Gln Tyr Pro Arg Leu Gln Gly Gly Phe Val Trp
        655                 660                 665 gac tgg gtg gat cag tcg ctg att aaa tat gat gaa aac ggc aac ccg      2368
Asp Trp Val Asp Gln Ser Leu Ile Lys Tyr Asp Glu Asn Gly Asn Pro
    670                 675                 680 tgg tcg gct tac ggc ggt gat ttt ggc gat acg ccg aac gat cgc cag      2416
Trp Ser Ala Tyr Gly Gly Asp Phe Gly Asp Thr Pro Asn Asp Arg Gln
685                 690                 695 ttc tgt atg aac ggt ctg gtc ttt gcc gac cgc acg ccg cat cca gcg      2464
Phe Cys Met Asn Gly Leu Val Phe Ala Asp Arg Thr Pro His Pro Ala
700                 705                 710                 715 ctg acg gaa gca aaa cac cag cag cag ttt ttc cag ttc cgt tta tcc      2512
Leu Thr Glu Ala Lys His Gln Gln Gln Phe Phe Gln Phe Arg Leu Ser
            720                 725                 730 ggg caa acc atc gaa gtg acc agc gaa tac ctg ttc cgt cat agc gat      2560
Gly Gln Thr Ile Glu Val Thr Ser Glu Tyr Leu Phe Arg His Ser Asp
        735                 740                 745 aac gag ctc ctg cac tgg atg gtg gcg ctg gat ggt aag ccg ctg gca      2608
Asn Glu Leu Leu His Trp Met Val Ala Leu Asp Gly Lys Pro Leu Ala
    750                 755                 760 agc ggt gaa gtg cct ctg gat gtc gct cca caa ggt aaa cag ttg att      2656
Ser Gly Glu Val Pro Leu Asp Val Ala Pro Gln Gly Lys Gln Leu Ile
765                 770                 775 gaa ctg cct gaa cta ccg cag ccg gag agc gcc ggg caa ctc tgg ctc      2704
Glu Leu Pro Glu Leu Pro Gln Pro Glu Ser Ala Gly Gln Leu Trp Leu
780                 785                 790                 795 aca gta cgc gta gtg caa ccg aac gcg acc gca tgg tca gaa gcc ggg      2752
Thr Val Arg Val Val Gln Pro Asn Ala Thr Ala Trp Ser Glu Ala Gly
            800                 805                 810 cac atc agc gcc tgg cag cag tgg cgt ctg gcg gaa aac ctc agt gtg      2800
His Ile Ser Ala Trp Gln Gln Trp Arg Leu Ala Glu Asn Leu Ser Val
        815                 820                 825 acg ctc ccc gcc gcg tcc cac gcc atc ccg cat ctg acc acc agc gaa      2848
Thr Leu Pro Ala Ala Ser His Ala Ile Pro His Leu Thr Thr Ser Glu
    830                 835                 840 atg gat ttt tgc atc gag ctg ggt aat aag cgt tgg caa ttt aac cgc      2896
Met Asp Phe Cys Ile Glu Leu Gly Asn Lys Arg Trp Gln Phe Asn Arg
845                 850                 855 cag tca ggc ttt ctt tca cag atg tgg att ggc gat aaa aaa caa ctg      2944
Gln Ser Gly Phe Leu Ser Gln Met Trp Ile Gly Asp Lys Lys Gln Leu
860                 865                 870                 875
```

| | |
|---|---|
| ctg acg ccg ctg cgc gat cag ttc acc cgt gca ccg ctg gat aac gac<br>Leu Thr Pro Leu Arg Asp Gln Phe Thr Arg Ala Pro Leu Asp Asn Asp<br>880 885 890 | 2992 |
| att ggc gta agt gaa gcg acc cgc att gac cct aac gcc tgg gtc gaa<br>Ile Gly Val Ser Glu Ala Thr Arg Ile Asp Pro Asn Ala Trp Val Glu<br>895 900 905 | 3040 |
| cgc tgg aag gcg gcg ggc cat tac cag gcc gaa gca gcg ttg ttg cag<br>Arg Trp Lys Ala Ala Gly His Tyr Gln Ala Glu Ala Ala Leu Leu Gln<br>910 915 920 | 3088 |
| tgc acg gca gat aca ctt gct gat gcg gtg ctg att acg acc gct cac<br>Cys Thr Ala Asp Thr Leu Ala Asp Ala Val Leu Ile Thr Thr Ala His<br>925 930 935 | 3136 |
| gcg tgg cag cat cag ggg aaa acc tta ttt atc agc cgg aaa acc tac<br>Ala Trp Gln His Gln Gly Lys Thr Leu Phe Ile Ser Arg Lys Thr Tyr<br>940 945 950 955 | 3184 |
| cgg att gat ggt agt ggt caa atg gcg att acc gtt gat gtt gaa gtg<br>Arg Ile Asp Gly Ser Gly Gln Met Ala Ile Thr Val Asp Val Glu Val<br>960 965 970 | 3232 |
| gcg agc gat aca ccg cat ccg gcg cgg att ggc ctg aac tgc cag ctg<br>Ala Ser Asp Thr Pro His Pro Ala Arg Ile Gly Leu Asn Cys Gln Leu<br>975 980 985 | 3280 |
| gcg cag gta gca gag cgg gta aac tgg ctc gga tta ggg ccg caa gaa<br>Ala Gln Val Ala Glu Arg Val Asn Trp Leu Gly Leu Gly Pro Gln Glu<br>990 995 1000 | 3328 |
| aac tat ccc gac cgc ctt act gcc gcc tgt ttt gac cgc tgg gat ctg<br>Asn Tyr Pro Asp Arg Leu Thr Ala Ala Cys Phe Asp Arg Trp Asp Leu<br>1005 1010 1015 | 3376 |
| cca ttg tca gac atg tat acc ccg tac gtc ttc ccg agc gaa aac ggt<br>Pro Leu Ser Asp Met Tyr Thr Pro Tyr Val Phe Pro Ser Glu Asn Gly<br>1020 1025 1030 1035 | 3424 |
| ctg cgc tgc ggg acg cgc gaa ttg aat tat ggc cca cac cag tgg cgc<br>Leu Arg Cys Gly Thr Arg Glu Leu Asn Tyr Gly Pro His Gln Trp Arg<br>1040 1045 1050 | 3472 |
| ggc gac ttc cag ttc aac atc agc cgc tac agt caa cag caa ctg atg<br>Gly Asp Phe Gln Phe Asn Ile Ser Arg Tyr Ser Gln Gln Gln Leu Met<br>1055 1060 1065 | 3520 |
| gaa acc agc cat cgc cat ctg ctg cac gcg gaa gaa ggc aca tgg ctg<br>Glu Thr Ser His Arg His Leu Leu His Ala Glu Glu Gly Thr Trp Leu<br>1070 1075 1080 | 3568 |
| aat atc gac ggt ttc cat atg ggg att ggt ggc gac gac tcc tgg agc<br>Asn Ile Asp Gly Phe His Met Gly Ile Gly Gly Asp Asp Ser Trp Ser<br>1085 1090 1095 | 3616 |
| ccg tca gta tcg gcg gaa ttc cag ctg agc gcc ggt cgc tac cat tac<br>Pro Ser Val Ser Ala Glu Phe Gln Leu Ser Ala Gly Arg Tyr His Tyr<br>1100 1105 1110 1115 | 3664 |
| cag ttg gtc tgg tgt caa aaa taagcttggc tgttttggcg gatgagagaa<br>Gln Leu Val Trp Cys Gln Lys<br>1120 | 3715 |
| gattttcagc ctgatacaga ttaaatcaga acgcagaagc ggtctgataa aacagaattt | 3775 |
| gcctggcggc agtagcgcgg tggtcccacc tgaccccatg ccgaactcag aagtgaaacg | 3835 |
| ccgtagcgcc gatggtagtg tggggtctcc ccatgcgaga gtagggaact gccaggcatc | 3895 |
| aaataaaacg aaaggctcag tcgaaagact gggcctttcg ttttatctgt tgtttgtcgg | 3955 |
| tgaacgctct cctgagtagg acaaatccgc cgggagcgga tttgaacgtt gcgaagcaac | 4015 |
| ggcccgagg gtggcgggca ggacgcccgc cataaactgc caggcatcaa attaagcaga | 4075 |
| aggccatcct gacggatggc cttttttgcgt ttctacaaac tcttttttgtt tatttttcta | 4135 |

```
aatacattca aatatgtatc cgctcatgag acaataaccc tgataaatgc ttcaataata   4195
ttgaaaaagg aagagtatga gtattcaaca tttccgtgtc gcccttattc ccttttttgc   4255
ggcattttgc cttcctgttt ttgctcaccc agaaacgctg gtgaaagtaa aagatgctga   4315
agatcagttg ggtgcacgag tgggttacat cgaactggat ctcaacagcg gtaagatcct   4375
tgagagtttt cgccccgaag aacgttttcc aatgatgagc acttttaaag ttctgctatg   4435
tggcgcggta ttatcccgtg ttgacgccgg gcaagagcaa ctcggtcgcc gcatacacta   4495
ttctcagaat gacttggttg agtactcacc agtcacagaa aagcatctta cggatggcat   4555
gacagtaaga gaattatgca gtgctgccat aaccatgagt gataacactg cggccaactt   4615
acttctgaca acgatcggag gaccgaagga gctaaccgct tttttgcaca acatggggga   4675
tcatgtaact cgccttgatc gttgggaacc ggagctgaat gaagccatac caaacgacga   4735
gcgtgacacc acgatgcctg tagcaatggc aacaacgttg cgcaaactat taactggcga   4795
actacttact ctagcttccc ggcaacaatt aatagactgg atggaggcgg ataaagttgc   4855
aggaccactt ctgcgctcgg cccttccggc tggctggttt attgctgata atctggagc    4915
cggtgagcgt gggtctcgcg gtatcattgc agcactgggg ccagatggta agccctcccg   4975
tatcgtagtt atctacacga cggggagtca ggcaactatg gatgaacgaa atagacagat   5035
cgctgagata ggtgcctcac tgattaagca ttggtaactg tcagaccaag tttactcata   5095
tatactttag attgatttaa aacttcattt ttaatttaaa aggatctagg tgaagatcct   5155
ttttgataat ctcatgacca aaatccctta acgtgagttt tcgttccact gagcgtcaga   5215
ccccgtagaa aagatcaaag gatcttcttg agatcctttt tttctgcgcg taatctgctg   5275
cttgcaaaca aaaaaaccac cgctaccagc ggtggtttgt ttgccggatc aagagctacc   5335
aactcttttt ccgaaggtaa ctggcttcag cagagcgcag ataccaaata ctgtccttct   5395
agtgtagccg tagttaggcc accacttcaa gaactctgta gcaccgccta catacctcgc   5455
tctgctaatc ctgttaccag tggctgctgc cagtggcgat aagtcgtgtc ttaccgggtt   5515
ggactcaaga cgatagttac cggataaggc gcagcggtcg ggctgaacgg ggggttcgtg   5575
cacacagccc agcttggagc gaacgaccta caccgaactg agatacctac agcgtgagct   5635
atgagaaagc gccacgcttc ccgaagggag aaaggcggac aggtatccgg taagcggcag   5695
ggtcggaaca ggagagcgca cgagggagct tccaggggga aacgcctggt atctttatag   5755
tcctgtcggg tttcgccacc tctgacttga gcgtcgattt ttgtgatgct cgtcaggggg   5815
gcggagccta tggaaaaacg ccagcaacgc ggccttttta cggttcctgg ccttttgctg   5875
gccttttgct cacatgttct ttcctgcgtt atcccctgat tctgtggata accgtattac   5935
cgcctttgag tgagctgata ccgctcgccg cagccgaacg accgagcgca gcgagtcagt   5995
gagcgaggaa gcggaagagc gcctgatgcg gtattttctc cttacgcatc tgtgcggtat   6055
ttcacaccgc atatggtgca ctctcagtac aatctgctct gatgccgcat agttaagcca   6115
gtatacactc cgctatcgct acgtgactgg gtcatggctg cgccccgaca cccgccaaca   6175
cccgctgacg cgccctgacg ggcttgtctg ctcccggcat ccgcttacag acaagctgtg   6235
accgtctccg ggagctgcat gtgtcagagg ttttcaccgt catcaccgaa acgcgcgagg   6295
cagcagatca attcgcgcgc gaaggcgaag cggcatgcat aatgtgcctg tcaaatggac   6355
gaagcaggga ttctgcaaac cctatgctac tccgtcaagc cgtcaattgt ctgattcgtt   6415
accaattatg acaacttgac ggctacatca ttcactttt  cttcacaacc ggcacgaac    6475
tcgctcgggc tggccccggt gcatttttta aatacccgcg agaaatagag ttgatcgtca   6535
```

```
aaaccaacat tgcgaccgac ggtggcgata ggcatccggg tggtgctcaa aagcagcttc    6595
gcctggctga tacgttggtc ctcgcgccag cttaagacgc taatccctaa ctgctggcgg    6655
aaaagatgtg acagacgcga cggcgacaag caaacatgct gtgcgacgct ggcgatatca    6715
aaattgctgt ctgccaggtg atcgctgatg tactgacaag cctcgcgtac ccgattatcc    6775
atcggtggat ggagcgactc gttaatcgct tccatgcgcc gcagtaacaa ttgctcaagc    6835
agatttatcg ccagcagctc cgaatagcgc ccttcccctt gcccggcgtt aatgatttgc    6895
ccaaacaggt cgctgaaatg cggctggtgc gcttcatccg ggcgaaagaa ccccgtattg    6955
gcaaatattg acggccagtt aagccattca tgccagtagg cgcgcggacg aaagtaaacc    7015
cactggtgat accattcgcg agcctccgga tgacgaccgt agtgatgaat ctctcctggc    7075
gggaacagca aaatatcacc cggtcggcaa acaaattctc gtccctgatt tttcaccacc    7135
ccctgaccgc gaatggtgag attgagaata taacctttca ttcccagcgg tcggtcgata    7195
aaaaaatcga gataaccgtt ggcctcaatc ggcgttaaac ccgccaccag atgggcatta    7255
aacgagtatc ccggcagcag gggatcattt tgcgcttcag ccatactttt catactcccg    7315
ccattcagag                                                           7325
```

<210> SEQ ID NO 45
<211> LENGTH: 1122
<212> TYPE: PRT
<213> ORGANISM: Artificial Sequence
<220> FEATURE:
<223> OTHER INFORMATION: Description of Artificial Sequence: fusion
   protein comprising a poly-histidine region, a nuclear
   localization signal from SV40 large T antigen, a TAT signal
   sequence from HIV, a region of the human HIF-1alpha gene, and the
   Beta-galactosidase protein from E. coli.

<400> SEQUENCE: 45

```
Met Gly Gly Ser His His His His His Gly Met Ala Ser Met Thr
 1               5                  10                  15

Gly Gly Gln Gln Met Gly Arg Asp Leu Tyr Asp Asp Asp Lys Asp
            20                  25                  30

Gln Leu Asp Met Ala Pro Lys Lys Lys Arg Lys Arg Ser Tyr Gly Arg
        35                  40                  45

Lys Lys Arg Arg Gln Arg Arg Arg Ser Leu Asp Leu Glu Met Leu
    50                  55                  60

Ala Pro Tyr Ile Pro Met Asp Asp Asp Phe Gln Leu Gln Val Pro Val
65                  70                  75                  80

Gly Glu Asp Gln Lys Gln His Leu Glu Leu Ser Arg Asp Ile Ala Gln
                85                  90                  95

Arg Phe Asn Ala Leu Tyr Gly Glu Ile Asp Pro Val Val Leu Gln Arg
            100                 105                 110

Arg Asp Trp Glu Asn Pro Gly Val Thr Gln Leu Asn Arg Leu Ala Ala
        115                 120                 125

His Pro Pro Phe Ala Ser Trp Arg Asn Ser Glu Glu Ala Arg Thr Asp
    130                 135                 140

Arg Pro Ser Gln Gln Leu Arg Ser Leu Asn Gly Glu Trp Arg Phe Ala
145                 150                 155                 160

Trp Phe Pro Ala Pro Glu Ala Val Pro Glu Ser Trp Leu Glu Cys Asp
                165                 170                 175

Leu Pro Glu Ala Asp Thr Val Val Val Pro Ser Asn Trp Gln Met His
            180                 185                 190
```

```
Gly Tyr Asp Ala Pro Ile Tyr Thr Asn Val Thr Tyr Pro Ile Thr Val
        195                 200                 205

Asn Pro Pro Phe Val Pro Thr Glu Asn Pro Thr Gly Cys Tyr Ser Leu
    210                 215                 220

Thr Phe Asn Val Asp Glu Ser Trp Leu Gln Gly Gln Thr Arg Ile
225                 230                 235                 240

Ile Phe Asp Gly Val Asn Ser Ala Phe His Leu Trp Cys Asn Gly Arg
                245                 250                 255

Trp Val Gly Tyr Gly Gln Asp Ser Arg Leu Pro Ser Glu Phe Asp Leu
            260                 265                 270

Ser Ala Phe Leu Arg Ala Gly Glu Asn Arg Leu Ala Val Met Val Leu
        275                 280                 285

Arg Trp Ser Asp Gly Ser Tyr Leu Glu Asp Gln Asp Met Trp Arg Met
    290                 295                 300

Ser Gly Ile Phe Arg Asp Val Ser Leu Leu His Lys Pro Thr Thr Gln
305                 310                 315                 320

Ile Ser Asp Phe His Val Ala Thr Arg Phe Asn Asp Asp Phe Ser Arg
                325                 330                 335

Ala Val Leu Glu Ala Glu Val Gln Met Cys Gly Glu Leu Arg Asp Tyr
            340                 345                 350

Leu Arg Val Thr Val Ser Leu Trp Gln Gly Glu Thr Gln Val Ala Ser
        355                 360                 365

Gly Thr Ala Pro Phe Gly Gly Glu Ile Ile Asp Glu Arg Gly Gly Tyr
    370                 375                 380

Ala Asp Arg Val Thr Leu Arg Leu Asn Val Glu Asn Pro Lys Leu Trp
385                 390                 395                 400

Ser Ala Glu Ile Pro Asn Leu Tyr Arg Ala Val Val Glu Leu His Thr
                405                 410                 415

Ala Asp Gly Thr Leu Ile Glu Ala Glu Ala Cys Asp Val Gly Phe Arg
            420                 425                 430

Glu Val Arg Ile Glu Asn Gly Leu Leu Leu Leu Asn Gly Lys Pro Leu
        435                 440                 445

Leu Ile Arg Gly Val Asn Arg His Glu His His Pro Leu His Gly Gln
    450                 455                 460

Val Met Asp Glu Gln Thr Met Val Gln Asp Ile Leu Leu Met Lys Gln
465                 470                 475                 480

Asn Asn Phe Asn Ala Val Arg Cys Ser His Tyr Pro Asn His Pro Leu
                485                 490                 495

Trp Tyr Thr Leu Cys Asp Arg Tyr Gly Leu Tyr Val Val Asp Glu Ala
            500                 505                 510

Asn Ile Glu Thr His Gly Met Val Pro Met Asn Arg Leu Thr Asp Asp
        515                 520                 525

Pro Arg Trp Leu Pro Ala Met Ser Glu Arg Val Thr Arg Met Val Gln
    530                 535                 540

Arg Asp Arg Asn His Pro Ser Val Ile Ile Trp Ser Leu Gly Asn Glu
545                 550                 555                 560

Ser Gly His Gly Ala Asn His Asp Ala Leu Tyr Arg Trp Ile Lys Ser
                565                 570                 575

Val Asp Pro Ser Arg Pro Val Gln Tyr Glu Gly Gly Gly Ala Asp Thr
            580                 585                 590

Thr Ala Thr Asp Ile Ile Cys Pro Met Tyr Ala Arg Val Asp Glu Asp
        595                 600                 605

Gln Pro Phe Pro Ala Val Pro Lys Trp Ser Ile Lys Lys Trp Leu Ser
```

-continued

```
            610                 615                 620
Leu Pro Gly Glu Thr Arg Pro Leu Ile Leu Cys Glu Tyr Ala His Ala
625                 630                 635                 640

Met Gly Asn Ser Leu Gly Gly Phe Ala Lys Tyr Trp Gln Ala Phe Arg
                645                 650                 655

Gln Tyr Pro Arg Leu Gln Gly Gly Phe Val Trp Asp Trp Val Asp Gln
            660                 665                 670

Ser Leu Ile Lys Tyr Asp Glu Asn Gly Asn Pro Trp Ser Ala Tyr Gly
                675                 680                 685

Gly Asp Phe Gly Asp Thr Pro Asn Asp Arg Gln Phe Cys Met Asn Gly
            690                 695                 700

Leu Val Phe Ala Asp Arg Thr Pro His Pro Ala Leu Thr Glu Ala Lys
705                 710                 715                 720

His Gln Gln Gln Phe Phe Gln Phe Arg Leu Ser Gly Gln Thr Ile Glu
                725                 730                 735

Val Thr Ser Glu Tyr Leu Phe Arg His Ser Asp Asn Glu Leu Leu His
                740                 745                 750

Trp Met Val Ala Leu Asp Gly Lys Pro Leu Ala Ser Gly Glu Val Pro
            755                 760                 765

Leu Asp Val Ala Pro Gln Gly Lys Gln Leu Ile Glu Leu Pro Glu Leu
            770                 775                 780

Pro Gln Pro Glu Ser Ala Gly Gln Leu Trp Leu Thr Val Arg Val Val
785                 790                 795                 800

Gln Pro Asn Ala Thr Ala Trp Ser Glu Ala Gly His Ile Ser Ala Trp
                805                 810                 815

Gln Gln Trp Arg Leu Ala Glu Asn Leu Ser Val Thr Leu Pro Ala Ala
            820                 825                 830

Ser His Ala Ile Pro His Leu Thr Thr Ser Glu Met Asp Phe Cys Ile
            835                 840                 845

Glu Leu Gly Asn Lys Arg Trp Gln Phe Asn Arg Gln Ser Gly Phe Leu
            850                 855                 860

Ser Gln Met Trp Ile Gly Asp Lys Lys Gln Leu Leu Thr Pro Leu Arg
865                 870                 875                 880

Asp Gln Phe Thr Arg Ala Pro Leu Asp Asn Asp Ile Gly Val Ser Glu
                885                 890                 895

Ala Thr Arg Ile Asp Pro Asn Ala Trp Val Glu Arg Trp Lys Ala Ala
            900                 905                 910

Gly His Tyr Gln Ala Glu Ala Ala Leu Leu Gln Cys Thr Ala Asp Thr
            915                 920                 925

Leu Ala Asp Ala Val Leu Ile Thr Thr Ala His Ala Trp Gln His Gln
930                 935                 940

Gly Lys Thr Leu Phe Ile Ser Arg Lys Thr Tyr Arg Ile Asp Gly Ser
945                 950                 955                 960

Gly Gln Met Ala Ile Thr Val Asp Val Glu Val Ala Ser Asp Thr Pro
                965                 970                 975

His Pro Ala Arg Ile Gly Leu Asn Cys Gln Leu Ala Gln Val Ala Glu
                980                 985                 990

Arg Val Asn Trp Leu Gly Leu Gly Pro Gln Glu Asn Tyr Pro Asp Arg
            995                 1000                1005

Leu Thr Ala Ala Cys Phe Asp Arg Trp Asp Leu Pro Leu Ser Asp Met
    1010                1015                1020

Tyr Thr Pro Tyr Val Phe Pro Ser Glu Asn Gly Leu Arg Cys Gly Thr
1025                1030                1035                1040
```

```
Arg Glu Leu Asn Tyr Gly Pro His Gln Trp Arg Gly Asp Phe Gln Phe
            1045                1050                1055

Asn Ile Ser Arg Tyr Ser Gln Gln Leu Met Glu Thr Ser His Arg
        1060                1065                1070

His Leu Leu His Ala Glu Gly Thr Trp Leu Asn Ile Asp Gly Phe
    1075                1080                1085

His Met Gly Ile Gly Gly Asp Asp Ser Trp Pro Ser Val Ser Ala
    1090                1095                1100

Glu Phe Gln Leu Ser Ala Gly Arg Tyr His Tyr Gln Leu Val Trp Cys
1105                1110                1115                1120

Gln Lys

<210> SEQ ID NO 46
<211> LENGTH: 6960
<212> TYPE: DNA
<213> ORGANISM: Artificial Sequence
<220> FEATURE:
<223> OTHER INFORMATION: Description of Artificial Sequence: fusion gene
      of 00 and 11
<220> FEATURE:
<221> NAME/KEY: CDS
<222> LOCATION: (10)..(3171)

<400> SEQUENCE: 46 aagcttgac atg gcg cct aag aag aag agg aag cag gta ccg gtg ggt gaa      51
          Met Ala Pro Lys Lys Lys Arg Lys Gln Val Pro Val Gly Glu
          1               5                   10 gac cag aaa cag cac ctc gaa ctg agc cgc gat att gcc cag cgt ttc        99
Asp Gln Lys Gln His Leu Glu Leu Ser Arg Asp Ile Ala Gln Arg Phe
15                  20                  25                  30 aac gcg ctg tat ggc gag atc gat ccc gtc gtt tta caa cgt cgt gac        147
Asn Ala Leu Tyr Gly Glu Ile Asp Pro Val Val Leu Gln Arg Arg Asp
                35                  40                  45 tgg gaa aac cct ggc gtt acc caa ctt aat cgc ctt gca gca cat ccc        195
Trp Glu Asn Pro Gly Val Thr Gln Leu Asn Arg Leu Ala Ala His Pro
            50                  55                  60 cct ttc gcc agc tgg cgt aat agc gaa gag gcc cgc acc gat cgc cct        243
Pro Phe Ala Ser Trp Arg Asn Ser Glu Glu Ala Arg Thr Asp Arg Pro
        65                  70                  75 tcc caa cag ttg cgc agc ctg aat ggc gaa tgg cgc ttt gcc tgg ttt        291
Ser Gln Gln Leu Arg Ser Leu Asn Gly Glu Trp Arg Phe Ala Trp Phe
    80                  85                  90 ccg gca cca gaa gcg gtg ccg gaa agc tgg ctg gag tgc gat ctt cct        339
Pro Ala Pro Glu Ala Val Pro Glu Ser Trp Leu Glu Cys Asp Leu Pro
95                  100                 105                 110 gag gcc gat act gtc gtc gtc ccc tca aac tgg cag atg cac ggt tac        387
Glu Ala Asp Thr Val Val Val Pro Ser Asn Trp Gln Met His Gly Tyr
                115                 120                 125 gat gcg ccc atc tac acc aac gta acc tat ccc att acg gtc aat ccg        435
Asp Ala Pro Ile Tyr Thr Asn Val Thr Tyr Pro Ile Thr Val Asn Pro
            130                 135                 140 ccg ttt gtt ccc acg gag aat ccg acg ggt tgt tac tcg ctc aca ttt        483
Pro Phe Val Pro Thr Glu Asn Pro Thr Gly Cys Tyr Ser Leu Thr Phe
        145                 150                 155 aat gtt gat gaa agc tgg cta cag gaa ggc cag acg cga att att ttt        531
Asn Val Asp Glu Ser Trp Leu Gln Glu Gly Gln Thr Arg Ile Ile Phe
    160                 165                 170 gat ggc gtt aac tcg gcg ttt cat ctg tgg tgc aac ggg cgc tgg gtc        579
Asp Gly Val Asn Ser Ala Phe His Leu Trp Cys Asn Gly Arg Trp Val
175                 180                 185                 190
```

```
ggt tac ggc cag gac agt cgt ttg ccg tct gaa ttt gac ctg agc gca      627
Gly Tyr Gly Gln Asp Ser Arg Leu Pro Ser Glu Phe Asp Leu Ser Ala
            195                 200                 205 ttt tta cgc gcc gga gaa aac cgc ctc gcg gtg atg gtg ctg cgt tgg      675
Phe Leu Arg Ala Gly Glu Asn Arg Leu Ala Val Met Val Leu Arg Trp
    210                 215                 220 agt gac ggc agt tat ctg gaa gat cag gat atg tgg cgg atg agc ggc      723
Ser Asp Gly Ser Tyr Leu Glu Asp Gln Asp Met Trp Arg Met Ser Gly
225                 230                 235 att ttc cgt gac gtc tcg ttg ctg cat aaa ccg act aca caa atc agc      771
Ile Phe Arg Asp Val Ser Leu Leu His Lys Pro Thr Thr Gln Ile Ser
        240                 245                 250 gat ttc cat gtt gcc act cgc ttt aat gat gat ttc agc cgc gct gta      819
Asp Phe His Val Ala Thr Arg Phe Asn Asp Asp Phe Ser Arg Ala Val
255                 260                 265                 270 ctg gag gct gaa gtt cag atg tgc ggc gag ttg cgt gac tac cta cgg      867
Leu Glu Ala Glu Val Gln Met Cys Gly Glu Leu Arg Asp Tyr Leu Arg
            275                 280                 285 gta aca gtt tct tta tgg cag ggt gaa acg cag gtc gcc agc ggc acc      915
Val Thr Val Ser Leu Trp Gln Gly Glu Thr Gln Val Ala Ser Gly Thr
    290                 295                 300 gcg cct ttc ggc ggt gaa att atc gat gag cgt ggt ggt tat gcc gat      963
Ala Pro Phe Gly Gly Glu Ile Ile Asp Glu Arg Gly Gly Tyr Ala Asp
305                 310                 315 cgc gtc aca cta cgt ctg aac gtc gaa aac ccg aaa ctg tgg agc gcc     1011
Arg Val Thr Leu Arg Leu Asn Val Glu Asn Pro Lys Leu Trp Ser Ala
        320                 325                 330 gaa atc ccg aat ctc tat cgt gcg gtg gtt gaa ctg cac acc gcc gac     1059
Glu Ile Pro Asn Leu Tyr Arg Ala Val Val Glu Leu His Thr Ala Asp
335                 340                 345                 350 ggc acg ctg att gaa gca gaa gcc tgc gat gtc ggt ttc cgc gag gtg     1107
Gly Thr Leu Ile Glu Ala Glu Ala Cys Asp Val Gly Phe Arg Glu Val
            355                 360                 365 cgg att gaa aat ggt ctg ctg ctg ctg aac ggc aag ccg ttg ctg att     1155
Arg Ile Glu Asn Gly Leu Leu Leu Leu Asn Gly Lys Pro Leu Leu Ile
    370                 375                 380 cga ggc gtt aac cgt cac gag cat cat cct ctg cat ggt cag gtc atg     1203
Arg Gly Val Asn Arg His Glu His His Pro Leu His Gly Gln Val Met
385                 390                 395 gat gag cag acg atg gtg cag gat atc ctg ctg atg aag cag aac aac     1251
Asp Glu Gln Thr Met Val Gln Asp Ile Leu Leu Met Lys Gln Asn Asn
        400                 405                 410 ttt aac gcc gtg cgc tgt tcg cat tat ccg aac cat ccg ctg tgg tac     1299
Phe Asn Ala Val Arg Cys Ser His Tyr Pro Asn His Pro Leu Trp Tyr
415                 420                 425                 430 acg ctg tgc gac cgc tac ggc ctg tat gtg gtg gat gaa gcc aat att     1347
Thr Leu Cys Asp Arg Tyr Gly Leu Tyr Val Val Asp Glu Ala Asn Ile
            435                 440                 445 gaa acc cac ggc atg gtg cca atg aat cgt ctg acc gat gat ccg cgc     1395
Glu Thr His Gly Met Val Pro Met Asn Arg Leu Thr Asp Asp Pro Arg
    450                 455                 460 tgg cta ccg gcg atg agc gaa cgc gta acg cga atg gtg cag cgc gat     1443
Trp Leu Pro Ala Met Ser Glu Arg Val Thr Arg Met Val Gln Arg Asp
465                 470                 475 cgt aat cac ccg agt gtg atc atc tgg tcg ctg ggg aat gaa tca ggc     1491
Arg Asn His Pro Ser Val Ile Ile Trp Ser Leu Gly Asn Glu Ser Gly
        480                 485                 490 cac ggc gct aat cac gac gcg ctg tat cgc tgg atc aaa tct gtc gat     1539
His Gly Ala Asn His Asp Ala Leu Tyr Arg Trp Ile Lys Ser Val Asp
```

```
                495                 500                 505                 510
cct tcc cgc ccg gtg cag tat gaa ggc gga gcc gac acc acg gcc        1587
Pro Ser Arg Pro Val Gln Tyr Glu Gly Gly Ala Asp Thr Thr Ala
                515                 520                 525 acc gat att att tgc ccg atg tac gcg cgc gtg gat gaa gac cag ccc    1635
Thr Asp Ile Ile Cys Pro Met Tyr Ala Arg Val Asp Glu Asp Gln Pro
            530                 535                 540 ttc ccg gct gtg ccg aaa tgg tcc atc aaa aaa tgg ctt tcg cta cct    1683
Phe Pro Ala Val Pro Lys Trp Ser Ile Lys Lys Trp Leu Ser Leu Pro
            545                 550                 555 gga gag acg cgc ccg ctg atc ctt tgc gaa tac gcc cac gcg atg ggt    1731
Gly Glu Thr Arg Pro Leu Ile Leu Cys Glu Tyr Ala His Ala Met Gly
            560                 565                 570 aac agt ctt ggc ggt ttc gct aaa tac tgg cag gcg ttt cgt cag tat    1779
Asn Ser Leu Gly Gly Phe Ala Lys Tyr Trp Gln Ala Phe Arg Gln Tyr
575                 580                 585                 590 ccc cgt tta cag ggc ggc ttc gtc tgg gac tgg gtg gat cag tcg ctg    1827
Pro Arg Leu Gln Gly Gly Phe Val Trp Asp Trp Val Asp Gln Ser Leu
                595                 600                 605 att aaa tat gat gaa aac ggc aac ccg tgg tcg gct tac ggc ggt gat    1875
Ile Lys Tyr Asp Glu Asn Gly Asn Pro Trp Ser Ala Tyr Gly Gly Asp
            610                 615                 620 ttt ggc gat acg ccg aac gat cgc cag ttc tgt atg aac ggt ctg gtc    1923
Phe Gly Asp Thr Pro Asn Asp Arg Gln Phe Cys Met Asn Gly Leu Val
            625                 630                 635 ttt gcc gac cgc acg ccg cat cca gcg ctg acg gaa gca aaa cac cag    1971
Phe Ala Asp Arg Thr Pro His Pro Ala Leu Thr Glu Ala Lys His Gln
            640                 645                 650 cag cag ttt ttc cag ttc cgt tta tcc ggg caa acc atc gaa gtg acc    2019
Gln Gln Phe Phe Gln Phe Arg Leu Ser Gly Gln Thr Ile Glu Val Thr
655                 660                 665                 670 agc gaa tac ctg ttc cgt cat agc gat aac gag ctc ctg cac tgg atg    2067
Ser Glu Tyr Leu Phe Arg His Ser Asp Asn Glu Leu Leu His Trp Met
                675                 680                 685 gtg gcg ctg gat ggt aag ccg ctg gca agc ggt gaa gtg cct ctg gat    2115
Val Ala Leu Asp Gly Lys Pro Leu Ala Ser Gly Glu Val Pro Leu Asp
            690                 695                 700 gtc gct cca caa ggt aaa cag ttg att gaa ctg cct gaa cta ccg cag    2163
Val Ala Pro Gln Gly Lys Gln Leu Ile Glu Leu Pro Glu Leu Pro Gln
            705                 710                 715 ccg gag agc gcc ggg caa ctc tgg ctc aca gta cgc gta gtg caa ccg    2211
Pro Glu Ser Ala Gly Gln Leu Trp Leu Thr Val Arg Val Val Gln Pro
720                 725                 730 aac gcg acc gca tgg tca gaa gcc ggg cac atc agc gcc tgg cag cag    2259
Asn Ala Thr Ala Trp Ser Glu Ala Gly His Ile Ser Ala Trp Gln Gln
735                 740                 745                 750 tgg cgt ctg gcg gaa aac ctc agt gtg acg ctc ccc gcc gcg tcc cac    2307
Trp Arg Leu Ala Glu Asn Leu Ser Val Thr Leu Pro Ala Ala Ser His
                755                 760                 765 gcc atc ccg cat ctg acc acc agc gaa atg gat ttt tgc atc gag ctg    2355
Ala Ile Pro His Leu Thr Thr Ser Glu Met Asp Phe Cys Ile Glu Leu
            770                 775                 780 ggt aat aag cgt tgg caa ttt aac cgc cag tca ggc ttt ctt tca cag    2403
Gly Asn Lys Arg Trp Gln Phe Asn Arg Gln Ser Gly Phe Leu Ser Gln
            785                 790                 795 atg tgg att ggc gat aaa aaa caa ctg ctg acg ccg ctg cgc gat cag    2451
Met Trp Ile Gly Asp Lys Lys Gln Leu Leu Thr Pro Leu Arg Asp Gln
800                 805                 810 ttc acc cgt gca ccg ctg gat aac gac att ggc gta agt gaa gcg acc    2499
Phe Thr Arg Ala Pro Leu Asp Asn Asp Ile Gly Val Ser Glu Ala Thr
```

-continued

| | | |
|---|---|---|
| Phe Thr Arg Ala Pro Leu Asp Asn Asp Ile Gly Val Ser Glu Ala Thr<br>815                 820                 825                 830 | | |
| cgc att gac cct aac gcc tgg gtc gaa cgc tgg aag gcg gcg ggc cat<br>Arg Ile Asp Pro Asn Ala Trp Val Glu Arg Trp Lys Ala Ala Gly His<br>                835                 840                 845 | 2547 | |
| tac cag gcc gaa gca gcg ttg ttg cag tgc acg gca gat aca ctt gct<br>Tyr Gln Ala Glu Ala Ala Leu Leu Gln Cys Thr Ala Asp Thr Leu Ala<br>850                 855                 860 | 2595 | |
| gat gcg gtg ctg att acg acc gct cac gcg tgg cag cat cag ggg aaa<br>Asp Ala Val Leu Ile Thr Thr Ala His Ala Trp Gln His Gln Gly Lys<br>       865                 870                875 | 2643 | |
| acc tta ttt atc agc cgg aaa acc tac cgg att gat ggt agt ggt caa<br>Thr Leu Phe Ile Ser Arg Lys Thr Tyr Arg Ile Asp Gly Ser Gly Gln<br>880                 885                 890 | 2691 | |
| atg gcg att acc gtt gat gtt gaa gtg gcg agc gat aca ccg cat ccg<br>Met Ala Ile Thr Val Asp Val Glu Val Ala Ser Asp Thr Pro His Pro<br>895                 900                 905                 910 | 2739 | |
| gcg cgg att ggc ctg aac tgc cag ctg gcg cag gta gca gag cgg gta<br>Ala Arg Ile Gly Leu Asn Cys Gln Leu Ala Gln Val Ala Glu Arg Val<br>                915                 920                 925 | 2787 | |
| aac tgg ctc gga tta ggg ccg caa gaa aac tat ccc gac cgc ctt act<br>Asn Trp Leu Gly Leu Gly Pro Gln Glu Asn Tyr Pro Asp Arg Leu Thr<br>           930                 935                 940 | 2835 | |
| gcc gcc tgt ttt gac cgc tgg gat ctg cca ttg tca gac atg tat acc<br>Ala Ala Cys Phe Asp Arg Trp Asp Leu Pro Leu Ser Asp Met Tyr Thr<br>945                 950                 955 | 2883 | |
| ccg tac gtc ttc ccg agc gaa aac ggt ctg cgc tgc ggg acg cgc gaa<br>Pro Tyr Val Phe Pro Ser Glu Asn Gly Leu Arg Cys Gly Thr Arg Glu<br>960                 965                 970 | 2931 | |
| ttg aat tat ggc cca cac cag tgg cgc ggc gac ttc cag ttc aac atc<br>Leu Asn Tyr Gly Pro His Gln Trp Arg Gly Asp Phe Gln Phe Asn Ile<br>975                 980                 985                 990 | 2979 | |
| agc cgc tac agt caa cag caa ctg atg gaa acc agc cat cgc cat ctg<br>Ser Arg Tyr Ser Gln Gln Gln Leu Met Glu Thr Ser His Arg His Leu<br>                995                1000              1005 | 3027 | |
| ctg cac gcg gaa gaa ggc aca tgg ctg aat atc gac ggt ttc cat atg<br>Leu His Ala Glu Glu Gly Thr Trp Leu Asn Ile Asp Gly Phe His Met<br>          1010                1015              1020 | 3075 | |
| ggg att ggt ggc gac gac tcc tgg agc ccg tca gta tcg gcg gaa ttc<br>Gly Ile Gly Gly Asp Asp Ser Trp Ser Pro Ser Val Ser Ala Glu Phe<br>1025              1030              1035 | 3123 | |
| cag ctg agc gcc ggt cgc tac cat tac cag ttg gtc tgg tgt caa aaa<br>Gln Leu Ser Ala Gly Arg Tyr His Tyr Gln Leu Val Trp Cys Gln Lys<br>     1040              1045              1050 | 3171 | |
| taataataac cgggcaggcc atgtctgccc gtatttcgcg taaggaaatc cattatgtac | 3231 | |
| tatttaaaaa acacaaactt ttggatgttc ggtttattct ttttctttta ctttttatc | 3291 | |
| atgggagcct acttcccgtt tttcccgatt tggctacatg acatcaacca tatcagcaaa | 3351 | |
| agtgatacgg gtattatttt tgccgctatt tctctgttct cgctattatt ccaaccgctg | 3411 | |
| tttggtctgc tttctgacaa actcggaact tgtttattgc agcttataat ggttacaaat | 3471 | |
| aaagcaatag catcacaaat ttcacaaata aagcattttt tcactgcat tctagttgtg | 3531 | |
| gtttgtccaa actcatcaat gtatcttatc atgtctggat ccccaggaag ctcctctgtg | 3591 | |
| tcctcataaa ccctaacctc ctctacttga gaggacattc aatcatagg ctgcccatcc | 3651 | |
| accctctgtg tcctcctgtt aattaggtca cttaacaaaa aggaaattgg tagggggttt | 3711 | |
| ttcacagacc gctttctaag ggtaatttta aaatatctgg gaagtcccctt ccactgctgt | 3771 | |

```
gttccagaag tgttggtaaa cagcccacaa atgtcaacag cagaaacata caagctgtca  3831
gctttgcaca agggcccaac accctgctca tcaagaagca ctgtggttgc tgtgttagta  3891
atgtgcaaaa caggaggcac attttcccca cctgtgtagg ttccaaaata tctagtgttt  3951
tcatttttac ttggatcagg aacccagcac tccactggat aagcattatc cttatccaaa  4011
acagccttgt ggtcagtgtt catctgctga ctgtcaactg tagcattttt tggggttaca  4071
gtttgagcag gatatttggt cctgtagttt gctaacacac cctgcagctc caaaggttcc  4131
ccaccaacag caaaaaaatg aaaatttgac ccttgaatgg ttttccagc accatttca   4191
tgagtttttt gtgtccctga atgcaagttt aacatagcag ttaccccaat aacctcagtt  4251
ttaacagtaa cagcttccca catcaaaata tttccacagg ttaagtcctc atttaaatta  4311
ggcaaaggaa ttcttgaaga cgaaagggcc tcgtgatacg cctatttta taggttaatg    4371
tcatgataat aatggtttct tagacgtcag gtggcacttt tcggggaaat gtgcgcggaa  4431
cccctatttg tttattttc taaatacatt caaatatgta tccgctcatg agacaataac   4491
cctgataaat gcttcaataa tattgaaaaa ggaagagtat gagtattcaa catttccgtg  4551
tcgcccttat tcccttttt gcggcatttt gccttcctgt ttttgctcac ccagaaacgc   4611
tggtgaaagt aaaagatgct gaagatcagt tgggtgcacg agtgggttac atcgaactgg  4671
atctcaacag cggtaagatc cttgagagtt ttcgccccga agaacgtttt ccaatgatga  4731
gcacttttaa agttctgcta tgtggcgcgg tattatcccg tgttgacgcc gggcaagagc  4791
aactcggtcg ccgcatacac tattctcaga atgacttggt tgagtactca ccagtcacag  4851
aaaagcatct tacggatggc atgacagtaa gagaattatg cagtgctgcc ataaccatga  4911
gtgataacac tgcggccaac ttacttctga caacgatcgg aggaccgaag gagctaaccg  4971
cttttttgca caacatgggg gatcatgtaa ctcgccttga tcgttgggaa ccggagctga  5031
atgaagccat accaaacgac gagcgtgaca ccacgatgcc tgcagcaatg gcaacaacgt  5091
tgcgcaaact attaactggc gaactactta ctctagcttc ccggcaacaa ttaatagact  5151
ggatggaggc ggataaagtt gcaggaccac ttctgcgctc ggcccttccg gctggctggt  5211
ttattgctga taaatctgga gccggtgagc gtgggtctcg cggtatcatt gcagcactgg  5271
ggccagatgg taagccctcc cgtatcgtag ttatctacac gacggggagt caggcaacta  5331
tggatgaacg aaatagacag atcgctgaga taggtgcctc actgattaag cattggtaac  5391
tgtcagacca gtttactcat tatatacttt agattgattt aaaacttcat ttttaattta  5451
aaaggatcta ggtgaagatc ctttttgata atctcatgac caaaatccct taacgtgagt  5511
tttcgttcca ctgagcgtca gaccccgtag aaaagatcaa aggatcttct tgagatcctt  5571
tttttctgcg cgtaatctgc tgcttgcaaa caaaaaaacc accgctacca gcggtggttt  5631
gtttgccgga tcaagagcta ccaactcttt ttccgaaggt aactggcttc agcagagcgc  5691
agataccaaa tactgtcctt ctagtgtagc cgtagttagg ccaccacttc aagaactctg  5751
tagcaccgcc tacatacctc gctctgctaa tcctgttacc agtggctgct gccagtggcg  5811
ataagtcgtg tcttaccggg ttggactcaa gacgatagtt accggataag cgcagcggt   5871
cgggctgaac ggggggttcg tgcacacagc ccagcttgga gcgaacgacc tacaccgaac  5931
tgagatacct acagcgtgag cattgagaaa gcgccacgct tcccgaaggg agaaaggcgg  5991
acaggtatcc ggtaagcggc agggtcggaa caggagagcg cacgagggag cttccagggg  6051
gaaacgcctg gtatctttat agtcctgtcg ggtttcgcca cctctgactt gagcgtcgat  6111
ttttgtgatg ctcgtcaggg gggcggagcc tatggaaaaa cgccagcaac gcggcctttt  6171
```

-continued

```
tacggttcct ggccttttgc tggccttttg ctcacatgtt ctttcctgcg ttatcccctg      6231
attctgtgga taaccgtatt accgcctttg agtgagctga taccgctcgc cgcagccgaa      6291
cgaccgagcg cagcgagtca gtgagcgagg aagcggaaga gcgcctgatg cggtattttc      6351
tccttacgca tctgtgcggt atttcacacc gcatatggtg cactctcagt acaatctgct      6411
ctgatgccgc atagttaagc cagtatacac tccgctatcg ctacgtgact gggtcatggc      6471
tgcgccccga caccogccaa cacccgctga cgcgccctga cgggcttgtc tgctcccggc      6531
atccgcttac agacaagctg tgaccgtctc cgggagctgc atgtgtcaga ggttttcacc      6591
gtcatcaccg aaacgcgcga ggcagctgtg gaatgtgtgt cagttagggt gtggaaagtc      6651
cccaggctcc ccagcaggca gaagtatgca aagcatgcat ctcaattagt cagcaaccag      6711
gtgtggaaag tccccaggct ccccagcagg cagaagtatg caaagcatgc atctcaatta      6771
gtcagcaacc atagtcccgc ccctaactcc gcccatcccg ccctaactc cgcccagttc      6831 cgcccattct ccgccccatg gctgactaat ttttttatt tatgcagagg ccgaggccgc      6891
ctcggcctct gagctattcc agaagtagtg aggaggcttt tttggaggcc taggcttttg      6951
caaaaagct                                                             6960

<210> SEQ ID NO 47
<211> LENGTH: 1054
<212> TYPE: PRT
<213> ORGANISM: Artificial Sequence
<220> FEATURE:
<223> OTHER INFORMATION: Description of Artificial Sequence: fusion
      protein comprising a nuclear localization signal from SV40 large T
      antigen, and the Beta-galactosidase protein from E. coli.

<400> SEQUENCE: 47

Met Ala Pro Lys Lys Arg Lys Gln Val Pro Val Gly Glu Asp Gln
  1               5                  10                  15

Lys Gln His Leu Glu Leu Ser Arg Asp Ile Ala Gln Arg Phe Asn Ala
                 20                  25                  30

Leu Tyr Gly Glu Ile Asp Pro Val Val Leu Gln Arg Arg Asp Trp Glu
             35                  40                  45

Asn Pro Gly Val Thr Gln Leu Asn Arg Leu Ala Ala His Pro Pro Phe
         50                  55                  60

Ala Ser Trp Arg Asn Ser Glu Glu Ala Arg Thr Asp Arg Pro Ser Gln
 65                  70                  75                  80

Gln Leu Arg Ser Leu Asn Gly Glu Trp Arg Phe Ala Trp Phe Pro Ala
                 85                  90                  95

Pro Glu Ala Val Pro Glu Ser Trp Leu Glu Cys Asp Leu Pro Glu Ala
            100                 105                 110

Asp Thr Val Val Val Pro Ser Asn Trp Gln Met His Gly Tyr Asp Ala
        115                 120                 125

Pro Ile Tyr Thr Asn Val Thr Tyr Pro Ile Thr Val Asn Pro Pro Phe
    130                 135                 140

Val Pro Thr Glu Asn Pro Thr Gly Cys Tyr Ser Leu Thr Phe Asn Val
145                 150                 155                 160

Asp Glu Ser Trp Leu Gln Glu Gly Gln Thr Arg Ile Ile Phe Asp Gly
                165                 170                 175

Val Asn Ser Ala Phe His Leu Trp Cys Asn Gly Arg Trp Val Gly Tyr
            180                 185                 190

Gly Gln Asp Ser Arg Leu Pro Ser Glu Phe Asp Leu Ser Ala Phe Leu
        195                 200                 205
```

-continued

```
Arg Ala Gly Glu Asn Arg Leu Ala Val Met Val Leu Arg Trp Ser Asp
    210                 215                 220
Gly Ser Tyr Leu Glu Asp Gln Asp Met Trp Arg Met Ser Gly Ile Phe
225                 230                 235                 240
Arg Asp Val Ser Leu Leu His Lys Pro Thr Thr Gln Ile Ser Asp Phe
                245                 250                 255
His Val Ala Thr Arg Phe Asn Asp Asp Phe Ser Arg Ala Val Leu Glu
            260                 265                 270
Ala Glu Val Gln Met Cys Gly Glu Leu Arg Asp Tyr Leu Arg Val Thr
        275                 280                 285
Val Ser Leu Trp Gln Gly Glu Thr Gln Val Ala Ser Gly Thr Ala Pro
    290                 295                 300
Phe Gly Gly Glu Ile Ile Asp Glu Arg Gly Tyr Ala Asp Arg Val
305                 310                 315                 320
Thr Leu Arg Leu Asn Val Glu Asn Pro Lys Leu Trp Ser Ala Glu Ile
                325                 330                 335
Pro Asn Leu Tyr Arg Ala Val Val Glu Leu His Thr Ala Asp Gly Thr
            340                 345                 350
Leu Ile Glu Ala Glu Ala Cys Asp Val Gly Phe Arg Glu Val Arg Ile
        355                 360                 365
Glu Asn Gly Leu Leu Leu Asn Gly Lys Pro Leu Leu Ile Arg Gly
    370                 375                 380
Val Asn Arg His Glu His His Pro Leu His Gly Gln Val Met Asp Glu
385                 390                 395                 400
Gln Thr Met Val Gln Asp Ile Leu Leu Met Lys Gln Asn Asn Phe Asn
                405                 410                 415
Ala Val Arg Cys Ser His Tyr Pro Asn His Pro Leu Trp Tyr Thr Leu
            420                 425                 430
Cys Asp Arg Tyr Gly Leu Tyr Val Val Asp Glu Ala Asn Ile Glu Thr
        435                 440                 445
His Gly Met Val Pro Met Asn Arg Leu Thr Asp Asp Pro Arg Trp Leu
    450                 455                 460
Pro Ala Met Ser Glu Arg Val Thr Arg Met Val Gln Arg Asp Arg Asn
465                 470                 475                 480
His Pro Ser Val Ile Ile Trp Ser Leu Gly Asn Glu Ser Gly His Gly
                485                 490                 495
Ala Asn His Asp Ala Leu Tyr Arg Trp Ile Lys Ser Val Asp Pro Ser
            500                 505                 510
Arg Pro Val Gln Tyr Glu Gly Gly Gly Ala Asp Thr Thr Ala Thr Asp
        515                 520                 525
Ile Ile Cys Pro Met Tyr Ala Arg Val Asp Glu Asp Gln Pro Phe Pro
    530                 535                 540
Ala Val Pro Lys Trp Ser Ile Lys Lys Trp Leu Ser Leu Pro Gly Glu
545                 550                 555                 560
Thr Arg Pro Leu Ile Leu Cys Glu Tyr Ala His Ala Met Gly Asn Ser
                565                 570                 575
Leu Gly Gly Phe Ala Lys Tyr Trp Gln Ala Phe Arg Gln Tyr Pro Arg
            580                 585                 590
Leu Gln Gly Gly Phe Val Trp Asp Trp Val Asp Gln Ser Leu Ile Lys
        595                 600                 605
Tyr Asp Glu Asn Gly Asn Pro Trp Ser Ala Tyr Gly Gly Asp Phe Gly
    610                 615                 620
```

-continued

```
Asp Thr Pro Asn Asp Arg Gln Phe Cys Met Asn Gly Leu Val Phe Ala
625                 630                 635                 640

Asp Arg Thr Pro His Pro Ala Leu Thr Glu Ala Lys His Gln Gln Gln
            645                 650                 655

Phe Phe Gln Phe Arg Leu Ser Gly Gln Thr Ile Glu Val Thr Ser Glu
                660                 665                 670

Tyr Leu Phe Arg His Ser Asp Asn Glu Leu Leu His Trp Met Val Ala
            675                 680                 685

Leu Asp Gly Lys Pro Leu Ala Ser Gly Glu Val Pro Leu Asp Val Ala
        690                 695                 700

Pro Gln Gly Lys Gln Leu Ile Glu Leu Pro Glu Leu Pro Gln Pro Glu
705                 710                 715                 720

Ser Ala Gly Gln Leu Trp Leu Thr Val Arg Val Val Gln Pro Asn Ala
                725                 730                 735

Thr Ala Trp Ser Glu Ala Gly His Ile Ser Ala Trp Gln Gln Trp Arg
            740                 745                 750

Leu Ala Glu Asn Leu Ser Val Thr Leu Pro Ala Ala Ser His Ala Ile
        755                 760                 765

Pro His Leu Thr Thr Ser Glu Met Asp Phe Cys Ile Glu Leu Gly Asn
    770                 775                 780

Lys Arg Trp Gln Phe Asn Arg Gln Ser Gly Phe Leu Ser Gln Met Trp
785                 790                 795                 800

Ile Gly Asp Lys Lys Gln Leu Leu Thr Pro Leu Arg Asp Gln Phe Thr
                805                 810                 815

Arg Ala Pro Leu Asp Asn Asp Ile Gly Val Ser Glu Ala Thr Arg Ile
            820                 825                 830

Asp Pro Asn Ala Trp Val Glu Arg Trp Lys Ala Ala Gly His Tyr Gln
        835                 840                 845

Ala Glu Ala Ala Leu Leu Gln Cys Thr Ala Asp Thr Leu Ala Asp Ala
    850                 855                 860

Val Leu Ile Thr Thr Ala His Ala Trp Gln His Gln Gly Lys Thr Leu
865                 870                 875                 880

Phe Ile Ser Arg Lys Thr Tyr Arg Ile Asp Gly Ser Gly Gln Met Ala
                885                 890                 895

Ile Thr Val Asp Val Glu Val Ala Ser Asp Thr Pro His Pro Ala Arg
            900                 905                 910

Ile Gly Leu Asn Cys Gln Leu Ala Gln Val Ala Glu Arg Val Asn Trp
        915                 920                 925

Leu Gly Leu Gly Pro Gln Glu Asn Tyr Pro Asp Arg Leu Thr Ala Ala
    930                 935                 940

Cys Phe Asp Arg Trp Asp Leu Pro Leu Ser Asp Met Tyr Thr Pro Tyr
945                 950                 955                 960

Val Phe Pro Ser Glu Asn Gly Leu Arg Cys Gly Thr Arg Glu Leu Asn
                965                 970                 975

Tyr Gly Pro His Gln Trp Arg Gly Asp Phe Gln Phe Asn Ile Ser Arg
            980                 985                 990

Tyr Ser Gln Gln Gln Leu Met Glu Thr Ser His Arg His Leu Leu His
        995                 1000                1005

Ala Glu Glu Gly Thr Trp Leu Asn Ile Asp Gly Phe His Met Gly Ile
    1010                1015                1020

Gly Gly Asp Asp Ser Trp Ser Pro Ser Val Ser Ala Glu Phe Gln Leu
1025                1030                1035                1040

Ser Ala Gly Arg Tyr His Tyr Gln Leu Val Trp Cys Gln Lys
```

<210> SEQ ID NO 48
<211> LENGTH: 7002
<212> TYPE: DNA
<213> ORGANISM: Artificial Sequence
<220> FEATURE:
<223> OTHER INFORMATION: Description of Artificial Sequence: fusion gene of 00 and 11
<220> FEATURE:
<221> NAME/KEY: CDS
<222> LOCATION: (10)..(3213)

<400> SEQUENCE: 48

```
aagcttgac atg gcg cct aag aag aag agg aag cag gta cga tat ggt cgt        51
          Met Ala Pro Lys Lys Lys Arg Lys Gln Val Arg Tyr Gly Arg
            1               5                  10 aag aaa cgt cgc caa cgt cgc cga cag gta ccg gtg ggt gaa gac cag          99
Lys Lys Arg Arg Gln Arg Arg Arg Gln Val Pro Val Gly Glu Asp Gln
 15                  20                  25                  30 aaa cag cac ctc gaa ctg agc cgc gat att gcc cag cgt ttc aac gcg         147
Lys Gln His Leu Glu Leu Ser Arg Asp Ile Ala Gln Arg Phe Asn Ala
                 35                  40                  45 ctg tat ggc gag atc gat ccc gtc gtt tta caa cgt cgt gac tgg gaa         195
Leu Tyr Gly Glu Ile Asp Pro Val Val Leu Gln Arg Arg Asp Trp Glu
             50                  55                  60 aac cct ggc gtt acc caa ctt aat cgc ctt gca gca cat ccc cct ttc         243
Asn Pro Gly Val Thr Gln Leu Asn Arg Leu Ala Ala His Pro Pro Phe
 65                  70                  75 gcc agc tgg cgt aat agc gaa gag gcc cgc acc gat cgc cct tcc caa         291
Ala Ser Trp Arg Asn Ser Glu Glu Ala Arg Thr Asp Arg Pro Ser Gln
             80                  85                  90 cag ttg cgc agc ctg aat ggc gaa tgg cgc ttt gcc tgg ttt ccg gca         339
Gln Leu Arg Ser Leu Asn Gly Glu Trp Arg Phe Ala Trp Phe Pro Ala
 95                 100                 105                 110 cca gaa gcg gtg ccg gaa agc tgg ctg gag tgc gat ctt cct gag gcc         387
Pro Glu Ala Val Pro Glu Ser Trp Leu Glu Cys Asp Leu Pro Glu Ala
                115                 120                 125 gat act gtc gtc gtc ccc tca aac tgg cag atg cac ggt tac gat gcg         435
Asp Thr Val Val Val Pro Ser Asn Trp Gln Met His Gly Tyr Asp Ala
                130                 135                 140 ccc atc tac acc aac gta acc tat ccc att acg gtc aat ccg ccg ttt         483
Pro Ile Tyr Thr Asn Val Thr Tyr Pro Ile Thr Val Asn Pro Pro Phe
            145                 150                 155 gtt ccc acg gag aat ccg acg ggt tgt tac tcg ctc aca ttt aat gtt         531
Val Pro Thr Glu Asn Pro Thr Gly Cys Tyr Ser Leu Thr Phe Asn Val
160                 165                 170 gat gaa agc tgg cta cag gaa ggc cag acg cga att att ttt gat ggc         579
Asp Glu Ser Trp Leu Gln Glu Gly Gln Thr Arg Ile Ile Phe Asp Gly
175                 180                 185                 190 gtt aac tcg gcg ttt cat ctg tgg tgc aac ggg cgc tgg gtc ggt tac         627
Val Asn Ser Ala Phe His Leu Trp Cys Asn Gly Arg Trp Val Gly Tyr
                195                 200                 205 ggc cag gac agt cgt ttg ccg tct gaa ttt gac ctg agc gca ttt tta         675
Gly Gln Asp Ser Arg Leu Pro Ser Glu Phe Asp Leu Ser Ala Phe Leu
            210                 215                 220 cgc gcc gga gaa aac cgc ctc gcg gtg atg gtg ctg cgt tgg agt gac         723
Arg Ala Gly Glu Asn Arg Leu Ala Val Met Val Leu Arg Trp Ser Asp
            225                 230                 235 ggc agt tat ctg gaa gat cag gat atg tgg cgg atg agc ggc att ttc         771
Gly Ser Tyr Leu Glu Asp Gln Asp Met Trp Arg Met Ser Gly Ile Phe
240                 245                 250
```

-continued

```
cgt gac gtc tcg ttg ctg cat aaa ccg act aca caa atc agc gat ttc      819
Arg Asp Val Ser Leu Leu His Lys Pro Thr Thr Gln Ile Ser Asp Phe
255                 260                 265                 270 cat gtt gcc act cgc ttt aat gat gat ttc agc cgc gct gta ctg gag      867
His Val Ala Thr Arg Phe Asn Asp Asp Phe Ser Arg Ala Val Leu Glu
                275                 280                 285 gct gaa gtt cag atg tgc ggc gag ttg cgt gac tac cta cgg gta aca      915
Ala Glu Val Gln Met Cys Gly Glu Leu Arg Asp Tyr Leu Arg Val Thr
            290                 295                 300 gtt tct tta tgg cag ggt gaa acg cag gtc gcc agc ggc acc gcg cct      963
Val Ser Leu Trp Gln Gly Glu Thr Gln Val Ala Ser Gly Thr Ala Pro
        305                 310                 315 ttc ggc ggt gaa att atc gat gag cgt ggt ggt tat gcc gat cgc gtc     1011
Phe Gly Gly Glu Ile Ile Asp Glu Arg Gly Gly Tyr Ala Asp Arg Val
    320                 325                 330 aca cta cgt ctg aac gtc gaa aac ccg aaa ctg tgg agc gcc gaa atc     1059
Thr Leu Arg Leu Asn Val Glu Asn Pro Lys Leu Trp Ser Ala Glu Ile
335                 340                 345                 350 ccg aat ctc tat cgt gcg gtg gtt gaa ctg cac acc gcc gac ggc acg     1107
Pro Asn Leu Tyr Arg Ala Val Val Glu Leu His Thr Ala Asp Gly Thr
                355                 360                 365 ctg att gaa gca gaa gcc tgc gat gtc ggt ttc cgc gag gtg cgg att     1155
Leu Ile Glu Ala Glu Ala Cys Asp Val Gly Phe Arg Glu Val Arg Ile
            370                 375                 380 gaa aat ggt ctg ctg ctg ctg aac ggc aag ccg ttg ctg att cga ggc     1203
Glu Asn Gly Leu Leu Leu Leu Asn Gly Lys Pro Leu Leu Ile Arg Gly
        385                 390                 395 gtt aac cgt cac gag cat cat cct ctg cat ggt cag gtc atg gat gag     1251
Val Asn Arg His Glu His His Pro Leu His Gly Gln Val Met Asp Glu
    400                 405                 410 cag acg atg gtg cag gat atc ctg ctg atg aag cag aac aac ttt aac     1299
Gln Thr Met Val Gln Asp Ile Leu Leu Met Lys Gln Asn Asn Phe Asn
415                 420                 425                 430 gcc gtg cgc tgt tcg cat tat ccg aac cat ccg ctg tgg tac acg ctg     1347
Ala Val Arg Cys Ser His Tyr Pro Asn His Pro Leu Trp Tyr Thr Leu
                435                 440                 445 tgc gac cgc tac ggc ctg tat gtg gtg gat gaa gcc aat att gaa acc     1395
Cys Asp Arg Tyr Gly Leu Tyr Val Val Asp Glu Ala Asn Ile Glu Thr
            450                 455                 460 cac ggc atg gtg cca atg aat cgt ctg acc gat gat ccg cgc tgg cta     1443
His Gly Met Val Pro Met Asn Arg Leu Thr Asp Asp Pro Arg Trp Leu
        465                 470                 475 ccg gcg atg agc gaa cgc gta acg cga atg gtg cag cgc gat cgt aat     1491
Pro Ala Met Ser Glu Arg Val Thr Arg Met Val Gln Arg Asp Arg Asn
    480                 485                 490 cac ccg agt gtg atc atc tgg tcg ctg ggg aat gaa tca ggc cac ggc     1539
His Pro Ser Val Ile Ile Trp Ser Leu Gly Asn Glu Ser Gly His Gly
495                 500                 505                 510 gct aat cac gac gcg ctg tat cgc tgg atc aaa tct gtc gat cct tcc     1587
Ala Asn His Asp Ala Leu Tyr Arg Trp Ile Lys Ser Val Asp Pro Ser
                515                 520                 525 cgc ccg gtg cag tat gaa ggc ggc gga gcc gac acc acg gcc acc gat     1635
Arg Pro Val Gln Tyr Glu Gly Gly Gly Ala Asp Thr Thr Ala Thr Asp
            530                 535                 540 att att tgc ccg atg tac gcg cgc gtg gat gaa gac cag ccc ttc ccg     1683
Ile Ile Cys Pro Met Tyr Ala Arg Val Asp Glu Asp Gln Pro Phe Pro
        545                 550                 555 gct gtg ccg aaa tgg tcc atc aaa aaa tgg ctt tcg cta cct gga gag     1731
Ala Val Pro Lys Trp Ser Ile Lys Lys Trp Leu Ser Leu Pro Gly Glu
```

```
              560                 565                 570
acg cgc ccg ctg atc ctt tgc gaa tac gcc cac gcg atg ggt aac agt    1779
Thr Arg Pro Leu Ile Leu Cys Glu Tyr Ala His Ala Met Gly Asn Ser
575                 580                 585                 590 ctt ggc ggt ttc gct aaa tac tgg cag gcg ttt cgt cag tat ccc cgt    1827
Leu Gly Gly Phe Ala Lys Tyr Trp Gln Ala Phe Arg Gln Tyr Pro Arg
                    595                 600                 605 tta cag ggc ggc ttc gtc tgg gac tgg gtg gat cag tcg ctg att aaa    1875
Leu Gln Gly Gly Phe Val Trp Asp Trp Val Asp Gln Ser Leu Ile Lys
                610                 615                 620 tat gat gaa aac ggc aac ccg tgg tcg gct tac ggc ggt gat ttt ggc    1923
Tyr Asp Glu Asn Gly Asn Pro Trp Ser Ala Tyr Gly Gly Asp Phe Gly
            625                 630                 635 gat acg ccg aac gat cgc cag ttc tgt atg aac ggt ctg gtc ttt gcc    1971
Asp Thr Pro Asn Asp Arg Gln Phe Cys Met Asn Gly Leu Val Phe Ala
        640                 645                 650 gac cgc acg ccg cat cca gcg ctg acg gaa gca aaa cac cag cag cag    2019
Asp Arg Thr Pro His Pro Ala Leu Thr Glu Ala Lys His Gln Gln Gln
655                 660                 665                 670 ttt ttc cag ttc cgt tta tcc ggg caa acc atc gaa gtg acc agc gaa    2067
Phe Phe Gln Phe Arg Leu Ser Gly Gln Thr Ile Glu Val Thr Ser Glu
                    675                 680                 685 tac ctg ttc cgt cat agc gat aac gag ctc ctg cac tgg atg gtg gcg    2115
Tyr Leu Phe Arg His Ser Asp Asn Glu Leu Leu His Trp Met Val Ala
                690                 695                 700 ctg gat ggt aag ccg ctg gca agc ggt gaa gtg cct ctg gat gtc gct    2163
Leu Asp Gly Lys Pro Leu Ala Ser Gly Glu Val Pro Leu Asp Val Ala
            705                 710                 715 cca caa ggt aaa cag ttg att gaa ctg cct gaa cta ccg cag ccg gag    2211
Pro Gln Gly Lys Gln Leu Ile Glu Leu Pro Glu Leu Pro Gln Pro Glu
        720                 725                 730 agc gcc ggg caa ctc tgg ctc aca gta cgc gta gtg caa ccg aac gcg    2259
Ser Ala Gly Gln Leu Trp Leu Thr Val Arg Val Val Gln Pro Asn Ala
735                 740                 745                 750 acc gca tgg tca gaa gcc ggg cac atc agc gcc tgg cag cag tgg cgt    2307
Thr Ala Trp Ser Glu Ala Gly His Ile Ser Ala Trp Gln Gln Trp Arg
                    755                 760                 765 ctg gcg gaa aac ctc agt gtg acg ctc ccc gcc gcg tcc cac gcc atc    2355
Leu Ala Glu Asn Leu Ser Val Thr Leu Pro Ala Ala Ser His Ala Ile
                770                 775                 780 ccg cat ctg acc acc agc gaa atg gat ttt tgc atc gag ctg ggt aat    2403
Pro His Leu Thr Thr Ser Glu Met Asp Phe Cys Ile Glu Leu Gly Asn
            785                 790                 795 aag cgt tgg caa ttt aac cgc cag tca ggc ttt ctt tca cag atg tgg    2451
Lys Arg Trp Gln Phe Asn Arg Gln Ser Gly Phe Leu Ser Gln Met Trp
        800                 805                 810 att ggc gat aaa aaa caa ctg ctg acg ccg ctg cgt gat cag ttc acc    2499
Ile Gly Asp Lys Lys Gln Leu Leu Thr Pro Leu Arg Asp Gln Phe Thr
815                 820                 825                 830 cgt gca ccg ctg gat aac gac att ggc gta agt gaa gcg acc cgc att    2547
Arg Ala Pro Leu Asp Asn Asp Ile Gly Val Ser Glu Ala Thr Arg Ile
                    835                 840                 845 gac cct aac gcc tgg gtc gaa cgc tgg aag gcg gcg ggc cat tac cag    2595
Asp Pro Asn Ala Trp Val Glu Arg Trp Lys Ala Ala Gly His Tyr Gln
                850                 855                 860 gcc gaa gca gcg ttg ttg cag tgc acg gca gat aca ctt gct gat gcg    2643
Ala Glu Ala Ala Leu Leu Gln Cys Thr Ala Asp Thr Leu Ala Asp Ala
            865                 870                 875 gtg ctg att acg acc gct cac gcg tgg cag cat cag ggg aaa acc tta    2691
```

```
                Val Leu Ile Thr Thr Ala His Ala Trp Gln His Gln Gly Lys Thr Leu
                    880                 885                 890 ttt atc agc cgg aaa acc tac cgg att gat ggt agt ggt caa atg gcg          2739
Phe Ile Ser Arg Lys Thr Tyr Arg Ile Asp Gly Ser Gly Gln Met Ala
895                 900                 905                 910 att acc gtt gat gtt gaa gtg gcg agc gat aca ccg cat ccg gcg cgg          2787
Ile Thr Val Asp Val Glu Val Ala Ser Asp Thr Pro His Pro Ala Arg
                915                 920                 925 att ggc ctg aac tgc cag ctg gcg cag gta gca gag cgg gta aac tgg          2835
Ile Gly Leu Asn Cys Gln Leu Ala Gln Val Ala Glu Arg Val Asn Trp
            930                 935                 940 ctc gga tta ggg ccg caa gaa aac tat ccc gac cgc ctt act gcc gcc          2883
Leu Gly Leu Gly Pro Gln Glu Asn Tyr Pro Asp Arg Leu Thr Ala Ala
        945                 950                 955 tgt ttt gac cgc tgg gat ctg cca ttg tca gac atg tat acc ccg tac          2931
Cys Phe Asp Arg Trp Asp Leu Pro Leu Ser Asp Met Tyr Thr Pro Tyr
    960                 965                 970 gtc ttc ccg agc gaa aac ggt ctg cgc tgc ggg acg cgc gaa ttg aat          2979
Val Phe Pro Ser Glu Asn Gly Leu Arg Cys Gly Thr Arg Glu Leu Asn
975                 980                 985                 990 tat ggc cca cac cag tgg cgc ggc gac ttc cag ttc aac atc agc cgc          3027
Tyr Gly Pro His Gln Trp Arg Gly Asp Phe Gln Phe Asn Ile Ser Arg
                995                 1000                1005 tac agt caa cag caa ctg atg gaa acc agc cat cgc cat ctg ctg cac          3075
Tyr Ser Gln Gln Gln Leu Met Glu Thr Ser His Arg His Leu Leu His
            1010                1015                1020 gcg gaa gaa ggc aca tgg ctg aat atc gac ggt ttc cat atg ggg att          3123
Ala Glu Glu Gly Thr Trp Leu Asn Ile Asp Gly Phe His Met Gly Ile
        1025                1030                1035 ggt ggc gac gac tcc tgg agc ccg tca gta tcg gcg gaa ttc cag ctg          3171
Gly Gly Asp Asp Ser Trp Ser Pro Ser Val Ser Ala Glu Phe Gln Leu
    1040                1045                1050 agc gcc ggt cgc tac cat tac cag ttg gtc tgg tgt caa aaa                  3213
Ser Ala Gly Arg Tyr His Tyr Gln Leu Val Trp Cys Gln Lys
1055                1060                1065 taataataac cgggcaggcc atgtctgccc gtatttcgcg taaggaaatc cattatgtac        3273
tatttaaaaa acacaaactt ttggatgttc ggtttattct tttttctttta cttttttatc      3333
atgggagcct acttcccgtt tttcccgatt tggctacatg acatcaacca tatcagcaaa       3393
agtgatacgg gtattatttt tgccgctatt tctctgttct cgctattatt ccaaccgctg       3453
tttggtctgc tttctgacaa actcggaact tgtttattgc agcttataat ggttacaaat       3513
aaagcaatag catcacaaat ttcacaaata aagcattttt ttcactgcat tctagttgtg      3573
gtttgtccaa actcatcaat gtatcttatc atgtctggat ccccaggaag ctcctctgtg       3633
tcctcataaa ccctaacctc ctctacttga gaggacattc aatcataggc tgcccatcc       3693
accctctgtg tcctcctgtt aattaggtca cttaacaaaa aggaaattgg gtaggggttt       3753
ttcacagacc gctttctaag ggtaatttta aaatatctgg gaagtcccctt ccactgctgt     3813
gttccagaag tgttggtaaa cagcccacaa atgtcaacag cagaaacata caagctgtca      3873
gctttgcaca agggcccaac accctgctca tcaagaagca ctgtggttgc tgtgttagta      3933
atgtgcaaaa caggaggcac atttt ccca cctgtgtagg ttccaaaata tctagtgttt      3993
tcatttttac ttggatcagg aacccagcac tccactggat aagcattatc cttatccaaa      4053
acagccttgt ggtcagtgtt catctgctga ctgtcaactg tagcattttt tggggttaca      4113
gtttgagcag gatatttggt cctgtagttt gctaacacac cctgcagctc caaaggttcc      4173
```

```
ccaccaacag caaaaaaatg aaaatttgac ccttgaatgg gttttccagc accattttca   4233
tgagtttttt gtgtccctga atgcaagttt aacatagcag ttaccccaat aacctcagtt   4293
ttaacagtaa cagcttccca catcaaaata tttccacagg ttaagtcctc atttaaatta   4353
ggcaaaggaa ttcttgaaga cgaaagggcc tcgtgatacg cctattttta taggttaatg   4413
tcatgataat aatggtttct tagacgtcag gtggcacttt tcggggaaat gtgcgcggaa   4473
cccctatttg tttattttc taaatacatt caaatatgta tccgctcatg agacaataac   4533
cctgataaat gcttcaataa tattgaaaaa ggaagagtat gagtattcaa catttccgtg   4593
tcgcccttat tccctttttt gcggcatttt gccttcctgt ttttgctcac ccagaaacgc   4653
tggtgaaagt aaaagatgct gaagatcagt tgggtgcacg agtgggttac atcgaactgg   4713
atctcaacag cggtaagatc cttgagagtt ttcgccccga agaacgtttt ccaatgatga   4773
gcacttttaa agttctgcta tgtggcgcgg tattatcccg tgttgacgcc gggcaagagc   4833
aactcggtcg ccgcatacac tattctcaga atgacttggt tgagtactca ccagtcacag   4893
aaaagcatct tacggatggc atgacagtaa gagaattatg cagtgctgcc ataaccatga   4953
gtgataacac tgcggccaac ttacttctga caacgatcgg aggaccgaag gagctaaccg   5013
cttttttgca acatggggg atcatgtaa ctcgccttga tcgttgggaa ccggagctga   5073
atgaagccat accaaacgac gagcgtgaca ccacgatgcc tgcagcaatg gcaacaacgt   5133
tgcgcaaact attaactggc gaactactta ctctagcttc ccggcaacaa ttaatagact   5193
ggatggaggc ggataaagtt gcaggaccac ttctgcgctc ggcccttccg gctggctggt   5253
ttattgctga taaatctgga gccggtgagc gtgggtctcg cggtatcatt gcagcactgg   5313
ggccagatgg taagccctcc cgtatcgtag ttatctacac gacggggagt caggcaacta   5373
tggatgaacg aaatagacag atcgctgaga taggtgcctc actgattaag cattggtaac   5433
tgtcagacca agtttactca tatatacttt agattgattt aaaacttcat ttttaattta   5493
aaaggatcta ggtgaagatc ctttttgata atctcatgac caaaatccct aacgtgagt   5553
tttcgttcca ctgagcgtca gaccccgtag aaaagatcaa aggatcttct tgagatcctt   5613
tttttctgcg cgtaatctgc tgcttgcaaa caaaaaaacc accgctacca gcggtggttt   5673
gtttgccgga tcaagagcta ccaactcttt ttccgaaggt aactggcttc agcagagcgc   5733
agataccaaa tactgtcctt ctagtgtagc cgtagttagg ccaccacttc aagaactctg   5793
tagcaccgcc tacatacctc gctctgctaa tcctgttacc agtggctgct gccagtggcg   5853
ataagtcgtg tcttaccggg ttggactcaa gacgatagtt accggataag gcgcagcggt   5913
cgggctgaac ggggggttcg tgcacacagc ccagcttgga gcgaacgacc tacaccgaac   5973
tgagatacct acagcgtgag cattgagaaa gcgccacgct tcccgaaggg agaaaggcgg   6033
acaggtatcc ggtaagcggc agggtcggaa caggagagcg cacgagggag cttccagggg   6093
gaaacgcctg gtatctttat agtcctgtcg ggtttcgcca cctctgactt gagcgtcgat   6153
ttttgtgatg ctcgtcaggg gggcggagcc tatggaaaaa cgccagcaac gcggcctttt   6213
tacggttcct ggccttttgc tggccttttg ctcacatgtt ctttcctgcg ttatcccctg   6273
attctgtgga taaccgtatt accgcctttg agtgagctga taccgctcgc cgcagccgaa   6333
cgaccgagcg cagcgagtca gtgagcgagg aagcggaaga gcgcctgatg cggtattttc   6393
tccttacgca tctgtgcggt atttcacacc gcatatggtg cactctcagt acaatctgct   6453
ctgatgccgc atagttaagc cagtatacac tccgctatcg ctacgtgact gggtcatggc   6513
tgcgccccga cacccgccaa cacccgctga cgcgccctga cgggcttgtc tgctcccggc   6573
```

-continued

```
atccgcttac agacaagctg tgaccgtctc cgggagctgc atgtgtcaga ggttttcacc    6633
gtcatcaccg aaacgcgcga ggcagctgtg gaatgtgtgt cagttagggt gtggaaagtc    6693
cccaggctcc ccagcaggca gaagtatgca aagcatgcat ctcaattagt cagcaaccag    6753
gtgtggaaag tccccaggct ccccagcagg cagaagtatg caaagcatgc atctcaatta    6813
gtcagcaacc atagtcccgc ccctaactcc gcccatcccg cccctaactc cgcccagttc    6873
cgcccattct ccgccccatg gctgactaat ttttttatt tatgcagagg ccgaggccgc     6933
ctcggcctct gagctattcc agaagtagtg aggaggcttt tttggaggcc taggcttttg    6993
caaaaagct                                                            7002
```

<210> SEQ ID NO 49
<211> LENGTH: 1068
<212> TYPE: PRT
<213> ORGANISM: Artificial Sequence
<220> FEATURE:
<223> OTHER INFORMATION: Description of Artificial Sequence: fusion
      protein comprising a nuclear localization signal from SV40 large T
      antigen, a TAT signal sequence from HIV, and the
      Beta-galactosidase protein from E. coli.

<400> SEQUENCE: 49

```
Met Ala Pro Lys Lys Arg Lys Gln Val Arg Tyr Gly Arg Lys Lys
  1               5                  10                  15

Arg Arg Gln Arg Arg Arg Gln Val Pro Val Gly Glu Asp Lys Gln
                 20                  25                  30

His Leu Glu Leu Ser Arg Asp Ile Ala Gln Arg Phe Asn Ala Leu Tyr
             35                  40                  45

Gly Glu Ile Asp Pro Val Val Leu Gln Arg Arg Asp Trp Glu Asn Pro
     50                  55                  60

Gly Val Thr Gln Leu Asn Arg Leu Ala Ala His Pro Pro Phe Ala Ser
 65                  70                  75                  80

Trp Arg Asn Ser Glu Glu Ala Arg Thr Asp Arg Pro Ser Gln Gln Leu
                 85                  90                  95

Arg Ser Leu Asn Gly Glu Trp Arg Phe Ala Trp Phe Pro Ala Pro Glu
            100                 105                 110

Ala Val Pro Glu Ser Trp Leu Glu Cys Asp Leu Pro Glu Ala Asp Thr
        115                 120                 125

Val Val Val Pro Ser Asn Trp Gln Met His Gly Tyr Asp Ala Pro Ile
    130                 135                 140

Tyr Thr Asn Val Thr Tyr Pro Ile Thr Val Asn Pro Pro Phe Val Pro
145                 150                 155                 160

Thr Glu Asn Pro Thr Gly Cys Tyr Ser Leu Thr Phe Asn Val Asp Glu
                165                 170                 175

Ser Trp Leu Gln Glu Gly Gln Thr Arg Ile Ile Phe Asp Gly Val Asn
            180                 185                 190

Ser Ala Phe His Leu Trp Cys Asn Gly Arg Trp Val Gly Tyr Gly Gln
        195                 200                 205

Asp Ser Arg Leu Pro Ser Glu Phe Asp Leu Ser Ala Phe Leu Arg Ala
    210                 215                 220

Gly Glu Asn Arg Leu Ala Val Met Val Leu Arg Trp Ser Asp Gly Ser
225                 230                 235                 240

Tyr Leu Glu Asp Gln Asp Met Trp Arg Met Ser Gly Ile Phe Arg Asp
                245                 250                 255

Val Ser Leu Leu His Lys Pro Thr Thr Gln Ile Ser Asp Phe His Val
```

-continued

```
                260                 265                 270
Ala Thr Arg Phe Asn Asp Asp Phe Ser Arg Ala Val Leu Glu Ala Glu
            275                 280                 285
Val Gln Met Cys Gly Glu Leu Arg Asp Tyr Leu Arg Val Thr Val Ser
        290                 295                 300
Leu Trp Gln Gly Glu Thr Gln Val Ala Ser Gly Thr Ala Pro Phe Gly
305                 310                 315                 320
Gly Glu Ile Ile Asp Glu Arg Gly Gly Tyr Ala Asp Arg Val Thr Leu
                325                 330                 335
Arg Leu Asn Val Glu Asn Pro Lys Leu Trp Ser Ala Glu Ile Pro Asn
            340                 345                 350
Leu Tyr Arg Ala Val Val Glu Leu His Thr Ala Asp Gly Thr Leu Ile
        355                 360                 365
Glu Ala Glu Ala Cys Asp Val Gly Phe Arg Glu Val Arg Ile Glu Asn
        370                 375                 380
Gly Leu Leu Leu Leu Asn Gly Lys Pro Leu Leu Ile Arg Gly Val Asn
385                 390                 395                 400
Arg His Glu His His Pro Leu His Gly Gln Val Met Asp Glu Gln Thr
                405                 410                 415
Met Val Gln Asp Ile Leu Leu Met Lys Gln Asn Asn Phe Asn Ala Val
            420                 425                 430
Arg Cys Ser His Tyr Pro Asn His Pro Leu Trp Tyr Thr Leu Cys Asp
        435                 440                 445
Arg Tyr Gly Leu Tyr Val Val Asp Glu Ala Asn Ile Glu Thr His Gly
    450                 455                 460
Met Val Pro Met Asn Arg Leu Thr Asp Asp Pro Arg Trp Leu Pro Ala
465                 470                 475                 480
Met Ser Glu Arg Val Thr Arg Met Val Gln Arg Asp Arg Asn His Pro
                485                 490                 495
Ser Val Ile Ile Trp Ser Leu Gly Asn Glu Ser Gly His Gly Ala Asn
            500                 505                 510
His Asp Ala Leu Tyr Arg Trp Ile Lys Ser Val Asp Pro Ser Arg Pro
        515                 520                 525
Val Gln Tyr Glu Gly Gly Gly Ala Asp Thr Thr Ala Thr Asp Ile Ile
    530                 535                 540
Cys Pro Met Tyr Ala Arg Val Asp Glu Asp Gln Pro Phe Pro Ala Val
545                 550                 555                 560
Pro Lys Trp Ser Ile Lys Lys Trp Leu Ser Leu Pro Gly Glu Thr Arg
                565                 570                 575
Pro Leu Ile Leu Cys Glu Tyr Ala His Ala Met Gly Asn Ser Leu Gly
            580                 585                 590
Gly Phe Ala Lys Tyr Trp Gln Ala Phe Arg Gln Tyr Pro Arg Leu Gln
        595                 600                 605
Gly Gly Phe Val Trp Asp Trp Val Asp Gln Ser Leu Ile Lys Tyr Asp
    610                 615                 620
Glu Asn Gly Asn Pro Trp Ser Ala Tyr Gly Gly Asp Phe Gly Asp Thr
625                 630                 635                 640
Pro Asn Asp Arg Gln Phe Cys Met Asn Gly Leu Val Phe Ala Asp Arg
                645                 650                 655
Thr Pro His Pro Ala Leu Thr Glu Ala Lys His Gln Gln Phe Phe
            660                 665                 670
Gln Phe Arg Leu Ser Gly Gln Thr Ile Glu Val Thr Ser Glu Tyr Leu
        675                 680                 685
```

-continued

```
Phe Arg His Ser Asp Asn Glu Leu Leu His Trp Met Val Ala Leu Asp
    690                 695                 700
Gly Lys Pro Leu Ala Ser Gly Glu Val Pro Leu Asp Val Ala Pro Gln
705                 710                 715                 720
Gly Lys Gln Leu Ile Glu Leu Pro Glu Leu Pro Gln Pro Glu Ser Ala
                725                 730                 735
Gly Gln Leu Trp Leu Thr Val Arg Val Gln Pro Asn Ala Thr Ala
            740                 745                 750
Trp Ser Glu Ala Gly His Ile Ser Ala Trp Gln Gln Trp Arg Leu Ala
        755                 760                 765
Glu Asn Leu Ser Val Thr Leu Pro Ala Ala Ser His Ala Ile Pro His
770                 775                 780
Leu Thr Thr Ser Glu Met Asp Phe Cys Ile Glu Leu Gly Asn Lys Arg
785                 790                 795                 800
Trp Gln Phe Asn Arg Gln Ser Gly Phe Leu Ser Gln Met Trp Ile Gly
                805                 810                 815
Asp Lys Lys Gln Leu Leu Thr Pro Leu Arg Asp Gln Phe Thr Arg Ala
            820                 825                 830
Pro Leu Asp Asn Asp Ile Gly Val Ser Glu Ala Thr Arg Ile Asp Pro
        835                 840                 845
Asn Ala Trp Val Glu Arg Trp Lys Ala Ala Gly His Tyr Gln Ala Glu
850                 855                 860
Ala Ala Leu Leu Gln Cys Thr Ala Asp Thr Leu Ala Asp Ala Val Leu
865                 870                 875                 880
Ile Thr Thr Ala His Ala Trp Gln His Gln Gly Lys Thr Leu Phe Ile
                885                 890                 895
Ser Arg Lys Thr Tyr Arg Ile Asp Gly Ser Gly Gln Met Ala Ile Thr
            900                 905                 910
Val Asp Val Glu Val Ala Ser Asp Thr Pro His Pro Ala Arg Ile Gly
        915                 920                 925
Leu Asn Cys Gln Leu Ala Gln Val Ala Glu Arg Val Asn Trp Leu Gly
930                 935                 940
Leu Gly Pro Gln Glu Asn Tyr Pro Asp Arg Leu Thr Ala Ala Cys Phe
945                 950                 955                 960
Asp Arg Trp Asp Leu Pro Leu Ser Asp Met Tyr Thr Pro Tyr Val Phe
                965                 970                 975
Pro Ser Glu Asn Gly Leu Arg Cys Gly Thr Arg Glu Leu Asn Tyr Gly
            980                 985                 990
Pro His Gln Trp Arg Gly Asp Phe Gln Phe Asn Ile Ser Arg Tyr Ser
        995                 1000                1005
Gln Gln Gln Leu Met Glu Thr Ser His Arg His Leu Leu His Ala Glu
1010                1015                1020
Glu Gly Thr Trp Leu Asn Ile Asp Gly Phe His Met Gly Ile Gly Gly
1025                1030                1035                1040
Asp Asp Ser Trp Ser Pro Ser Val Ser Ala Glu Phe Gln Leu Ser Ala
                1045                1050                1055
Gly Arg Tyr His Tyr Gln Leu Val Trp Cys Gln Lys
            1060                1065

<210> SEQ ID NO 50
<211> LENGTH: 7268
<212> TYPE: DNA
<213> ORGANISM: Artificial Sequence
<220> FEATURE:
```

-continued

```
<223> OTHER INFORMATION: Description of Artificial Sequence: fusion gene
      of 00 and 11
<220> FEATURE:
<221> NAME/KEY: CDS
<222> LOCATION: (320)..(3628)

<400> SEQUENCE: 50
aagaaaccaa ttgtccatat tgcatcagac attgccgtca ctgcgtcttt tactggctct     60
tctcgctaac caaaccggta accccgctta ttaaaagcat tctgtaacaa agcgggacca    120
aagccatgac aaaaacgcgt aacaaaagtg tctataatca cggcagaaaa gtccacattg    180
attatttgca cggcgtcaca ctttgctatg ccatagcatt tttatccata agattagcgg    240
atcctacctg acgcttttta tcgcaactct ctactgtttc tccatacccg ttttttgggg    300
ctaacaggag gaattaacc atg ggg ggt tct cat cat cat cat cat cat ggt    352
                     Met Gly Gly Ser His His His His His His Gly
                      1               5                   10 atg gct agc atg act ggt gga cag caa atg ggt cgg gat ctg tac gac    400
Met Ala Ser Met Thr Gly Gly Gln Gln Met Gly Arg Asp Leu Tyr Asp
             15                  20                  25 gat gac gat aag gat cag ctt gac atg gcg cct aag aag aag agg aag    448
Asp Asp Asp Lys Asp Gln Leu Asp Met Ala Pro Lys Lys Lys Arg Lys
         30                  35                  40 cag gta cga tat ggt cgt aag aaa cgt cgc caa cgt cgc cga cag gta    496
Gln Val Arg Tyr Gly Arg Lys Lys Arg Arg Gln Arg Arg Arg Gln Val
     45                  50                  55 ccg gtg ggt gaa gac cag aaa cag cac ctc gaa ctg agc cgc gat att    544
Pro Val Gly Glu Asp Gln Lys Gln His Leu Glu Leu Ser Arg Asp Ile
 60                  65                  70                  75 gcc cag cgt ttc aac gcg ctg tat ggc gag atc gat ccc gtc gtt tta    592
Ala Gln Arg Phe Asn Ala Leu Tyr Gly Glu Ile Asp Pro Val Val Leu
                 80                  85                  90 caa cgt cgt gac tgg gaa aac cct ggc gtt acc caa ctt aat cgc ctt    640
Gln Arg Arg Asp Trp Glu Asn Pro Gly Val Thr Gln Leu Asn Arg Leu
             95                 100                 105 gca gca cat ccc cct ttc gcc agc tgg cgt aat agc gaa gag gcc cgc    688
Ala Ala His Pro Pro Phe Ala Ser Trp Arg Asn Ser Glu Glu Ala Arg
         110                 115                 120 acc gat cgc cct tcc caa cag ttg cgc agc ctg aat ggc gaa tgg cgc    736
Thr Asp Arg Pro Ser Gln Gln Leu Arg Ser Leu Asn Gly Glu Trp Arg
     125                 130                 135 ttt gcc tgg ttt ccg gca cca gaa gcg gtg ccg gaa agc tgg ctg gag    784
Phe Ala Trp Phe Pro Ala Pro Glu Ala Val Pro Glu Ser Trp Leu Glu
140                 145                 150                 155 tgc gat ctt cct gag gcc gat act gtc gtc gtc ccc tca aac tgg cag    832
Cys Asp Leu Pro Glu Ala Asp Thr Val Val Val Pro Ser Asn Trp Gln
                 160                 165                 170 atg cac ggt tac gat gcg ccc atc tac acc aac gta acc tat ccc att    880
Met His Gly Tyr Asp Ala Pro Ile Tyr Thr Asn Val Thr Tyr Pro Ile
             175                 180                 185 acg gtc aat ccg ccg ttt gtt ccc acg gag aat ccg acg ggt tgt tac    928
Thr Val Asn Pro Pro Phe Val Pro Thr Glu Asn Pro Thr Gly Cys Tyr
         190                 195                 200 tcg ctc aca ttt aat gtt gat gaa agc tgg cta cag gaa ggc cag acg    976
Ser Leu Thr Phe Asn Val Asp Glu Ser Trp Leu Gln Glu Gly Gln Thr
     205                 210                 215 cga att att ttt gat ggc gtt aac tcg gcg ttt cat ctg tgg tgc aac   1024
Arg Ile Ile Phe Asp Gly Val Asn Ser Ala Phe His Leu Trp Cys Asn
220                 225                 230                 235 ggg cgc tgg gtc ggt tac ggc cag gac agt cgt ttg ccg tct gaa ttt   1072
```

```
                Gly Arg Trp Val Gly Tyr Gly Gln Asp Ser Arg Leu Pro Ser Glu Phe
                                240                 245                 250 gac ctg agc gca ttt tta cgc gcc gga gaa aac cgc ctc gcg gtg atg        1120
Asp Leu Ser Ala Phe Leu Arg Ala Gly Glu Asn Arg Leu Ala Val Met
            255                 260                 265 gtg ctg cgt tgg agt gac ggc agt tat ctg gaa gat cag gat atg tgg        1168
Val Leu Arg Trp Ser Asp Gly Ser Tyr Leu Glu Asp Gln Asp Met Trp
        270                 275                 280 cgg atg agc ggc att ttc cgt gac gtc tcg ttg ctg cat aaa ccg act        1216
Arg Met Ser Gly Ile Phe Arg Asp Val Ser Leu Leu His Lys Pro Thr
    285                 290                 295 aca caa atc agc gat ttc cat gtt gcc act cgc ttt aat gat gat ttc        1264
Thr Gln Ile Ser Asp Phe His Val Ala Thr Arg Phe Asn Asp Asp Phe
300                 305                 310                 315 agc cgc gct gta ctg gag gct gaa gtt cag atg tgc ggc gag ttg cgt        1312
Ser Arg Ala Val Leu Glu Ala Glu Val Gln Met Cys Gly Glu Leu Arg
                320                 325                 330 gac tac cta cgg gta aca gtt tct tta tgg cag ggt gaa acg cag gtc        1360
Asp Tyr Leu Arg Val Thr Val Ser Leu Trp Gln Gly Glu Thr Gln Val
            335                 340                 345 gcc agc ggc acc gcg cct ttc ggc ggt gaa att atc gat gag cgt ggt        1408
Ala Ser Gly Thr Ala Pro Phe Gly Gly Glu Ile Ile Asp Glu Arg Gly
        350                 355                 360 ggt tat gcc gat cgc gtc aca cta cgt ctg aac gtc gaa aac ccg aaa        1456
Gly Tyr Ala Asp Arg Val Thr Leu Arg Leu Asn Val Glu Asn Pro Lys
    365                 370                 375 ctg tgg agc gcc gaa atc ccg aat ctc tat cgt gcg gtg gtt gaa ctg        1504
Leu Trp Ser Ala Glu Ile Pro Asn Leu Tyr Arg Ala Val Val Glu Leu
380                 385                 390                 395 cac acc gcc gac ggc acg ctg att gaa gca gaa gcc tgc gat gtc ggt        1552
His Thr Ala Asp Gly Thr Leu Ile Glu Ala Glu Ala Cys Asp Val Gly
                400                 405                 410 ttc cgc gag gtg cgg att gaa aat ggt ctg ctg ctg ctg aac ggc aag        1600
Phe Arg Glu Val Arg Ile Glu Asn Gly Leu Leu Leu Leu Asn Gly Lys
            415                 420                 425 ccg ttg ctg att cga ggc gtt aac cgt cac gag cat cat cct ctg cat        1648
Pro Leu Leu Ile Arg Gly Val Asn Arg His Glu His His Pro Leu His
        430                 435                 440 ggt cag gtc atg gat gag cag acg atg gtg cag gat atc ctg ctg atg        1696
Gly Gln Val Met Asp Glu Gln Thr Met Val Gln Asp Ile Leu Leu Met
    445                 450                 455 aag cag aac aac ttt aac gcc gtg cgc tgt tcg cat tat ccg aac cat        1744
Lys Gln Asn Asn Phe Asn Ala Val Arg Cys Ser His Tyr Pro Asn His
460                 465                 470                 475 ccg ctg tgg tac acg ctg tgc gac cgc tac ggc ctg tat gtg gtg gat        1792
Pro Leu Trp Tyr Thr Leu Cys Asp Arg Tyr Gly Leu Tyr Val Val Asp
                480                 485                 490 gaa gcc aat att gaa acc cac ggc atg gtg cca atg aat cgt ctg acc        1840
Glu Ala Asn Ile Glu Thr His Gly Met Val Pro Met Asn Arg Leu Thr
            495                 500                 505 gat gat ccg cgc tgg cta ccg gcg atg agc gaa cgc gta acg cga atg        1888
Asp Asp Pro Arg Trp Leu Pro Ala Met Ser Glu Arg Val Thr Arg Met
        510                 515                 520 gtg cag cgc gat cgt aat cac ccg agt gtg atc atc tgg tcg ctg ggg        1936
Val Gln Arg Asp Arg Asn His Pro Ser Val Ile Ile Trp Ser Leu Gly
    525                 530                 535 aat gaa tca ggc cac ggc gct aat cac gac gcg ctg tat cgc tgg atc        1984
Asn Glu Ser Gly His Gly Ala Asn His Asp Ala Leu Tyr Arg Trp Ile
540                 545                 550                 555
```

```
aaa tct gtc gat cct tcc cgc ccg gtg cag tat gaa ggc ggc gga gcc      2032
Lys Ser Val Asp Pro Ser Arg Pro Val Gln Tyr Glu Gly Gly Gly Ala
            560                 565                 570 gac acc acg gcc acc gat att att tgc ccg atg tac gcg cgc gtg gat      2080
Asp Thr Thr Ala Thr Asp Ile Ile Cys Pro Met Tyr Ala Arg Val Asp
575                 580                 585 gaa gac cag ccc ttc ccg gct gtg ccg aaa tgg tcc atc aaa aaa tgg      2128
Glu Asp Gln Pro Phe Pro Ala Val Pro Lys Trp Ser Ile Lys Lys Trp
        590                 595                 600 ctt tcg cta cct gga gag acg cgc ccg ctg atc ctt tgc gaa tac gcc      2176
Leu Ser Leu Pro Gly Glu Thr Arg Pro Leu Ile Leu Cys Glu Tyr Ala
    605                 610                 615 cac gcg atg ggt aac agt ctt ggc ggt ttc gct aaa tac tgg cag gcg      2224
His Ala Met Gly Asn Ser Leu Gly Gly Phe Ala Lys Tyr Trp Gln Ala
620                 625                 630                 635 ttt cgt cag tat ccc cgt tta cag ggc ggc ttc gtc tgg gac tgg gtg      2272
Phe Arg Gln Tyr Pro Arg Leu Gln Gly Gly Phe Val Trp Asp Trp Val
            640                 645                 650 gat cag tcg ctg att aaa tat gat gaa aac ggc aac ccg tgg tcg gct      2320
Asp Gln Ser Leu Ile Lys Tyr Asp Glu Asn Gly Asn Pro Trp Ser Ala
655                 660                 665 tac ggc ggt gat ttt ggc gat acg ccg aac gat cgc cag ttc tgt atg      2368
Tyr Gly Gly Asp Phe Gly Asp Thr Pro Asn Asp Arg Gln Phe Cys Met
        670                 675                 680 aac ggt ctg gtc ttt gcc gac cgc acg ccg cat cca gcg ctg acg gaa      2416
Asn Gly Leu Val Phe Ala Asp Arg Thr Pro His Pro Ala Leu Thr Glu
    685                 690                 695 gca aaa cac cag cag cag ttt ttc cag ttc cgt tta tcc ggg caa acc      2464
Ala Lys His Gln Gln Gln Phe Phe Gln Phe Arg Leu Ser Gly Gln Thr
700                 705                 710                 715 atc gaa gtg acc agc gaa tac ctg ttc cgt cat agc gat aac gag ctc      2512
Ile Glu Val Thr Ser Glu Tyr Leu Phe Arg His Ser Asp Asn Glu Leu
            720                 725                 730 ctg cac tgg atg gtg gcg ctg gat ggt aag ccg ctg gca agc ggt gaa      2560
Leu His Trp Met Val Ala Leu Asp Gly Lys Pro Leu Ala Ser Gly Glu
735                 740                 745 gtg cct ctg gat gtc gct cca caa ggt aaa cag ttg att gaa ctg cct      2608
Val Pro Leu Asp Val Ala Pro Gln Gly Lys Gln Leu Ile Glu Leu Pro
        750                 755                 760 gaa cta ccg cag ccg gag agc gcc ggg caa ctc tgg ctc aca gta cgc      2656
Glu Leu Pro Gln Pro Glu Ser Ala Gly Gln Leu Trp Leu Thr Val Arg
    765                 770                 775 gta gtg caa ccg aac gcg acc gca tgg tca gaa gcc ggg cac atc agc      2704
Val Val Gln Pro Asn Ala Thr Ala Trp Ser Glu Ala Gly His Ile Ser
780                 785                 790                 795 gcc tgg cag cag tgg cgt ctg gcg gaa aac ctc agt gtg acg ctc ccc      2752
Ala Trp Gln Gln Trp Arg Leu Ala Glu Asn Leu Ser Val Thr Leu Pro
            800                 805                 810 gcc gcg tcc cac gcc atc ccg cat ctg acc acc agc gaa atg gat ttt      2800
Ala Ala Ser His Ala Ile Pro His Leu Thr Thr Ser Glu Met Asp Phe
815                 820                 825 tgc atc gag ctg ggt aat aag cgt tgg caa ttt aac cgc cag tca ggc      2848
Cys Ile Glu Leu Gly Asn Lys Arg Trp Gln Phe Asn Arg Gln Ser Gly
        830                 835                 840 ttt ctt tca cag atg tgg att ggc gat aaa aaa caa ctg ctg acg ccg      2896
Phe Leu Ser Gln Met Trp Ile Gly Asp Lys Lys Gln Leu Leu Thr Pro
    845                 850                 855 ctg cgc gat cag ttc acc cgt gca ccg ctg gat aac gac att ggc gta      2944
Leu Arg Asp Gln Phe Thr Arg Ala Pro Leu Asp Asn Asp Ile Gly Val
860                 865                 870                 875
```

| | |
|---|---|
| agt gaa gcg acc cgc att gac cct aac gcc tgg gtc gaa cgc tgg aag<br>Ser Glu Ala Thr Arg Ile Asp Pro Asn Ala Trp Val Glu Arg Trp Lys<br>880 885 890 | 2992 |
| gcg gcg ggc cat tac cag gcc gaa gca gcg ttg ttg cag tgc acg gca<br>Ala Ala Gly His Tyr Gln Ala Glu Ala Ala Leu Leu Gln Cys Thr Ala<br>895 900 905 | 3040 |
| gat aca ctt gct gat gcg gtg ctg att acg acc gct cac gcg tgg cag<br>Asp Thr Leu Ala Asp Ala Val Leu Ile Thr Thr Ala His Ala Trp Gln<br>910 915 920 | 3088 |
| cat cag ggg aaa acc tta ttt atc agc cgg aaa acc tac cgg att gat<br>His Gln Gly Lys Thr Leu Phe Ile Ser Arg Lys Thr Tyr Arg Ile Asp<br>925 930 935 | 3136 |
| ggt agt ggt caa atg gcg att acc gtt gat gtt gaa gtg gcg agc gat<br>Gly Ser Gly Gln Met Ala Ile Thr Val Asp Val Glu Val Ala Ser Asp<br>940 945 950 955 | 3184 |
| aca ccg cat ccg gcg cgg att ggc ctg aac tgc cag ctg gcg cag gta<br>Thr Pro His Pro Ala Arg Ile Gly Leu Asn Cys Gln Leu Ala Gln Val<br>960 965 970 | 3232 |
| gca gag cgg gta aac tgg ctc gga tta ggg ccg caa gaa aac tat ccc<br>Ala Glu Arg Val Asn Trp Leu Gly Leu Gly Pro Gln Glu Asn Tyr Pro<br>975 980 985 | 3280 |
| gac cgc ctt act gcc gcc tgt ttt gac cgc tgg gat ctg cca ttg tca<br>Asp Arg Leu Thr Ala Ala Cys Phe Asp Arg Trp Asp Leu Pro Leu Ser<br>990 995 1000 | 3328 |
| gac atg tat acc ccg tac gtc ttc ccg agc gaa aac ggt ctg cgc tgc<br>Asp Met Tyr Thr Pro Tyr Val Phe Pro Ser Glu Asn Gly Leu Arg Cys<br>1005 1010 1015 | 3376 |
| ggg acg cgc gaa ttg aat tat ggc cca cac cag tgg cgc ggc gac ttc<br>Gly Thr Arg Glu Leu Asn Tyr Gly Pro His Gln Trp Arg Gly Asp Phe<br>1020 1025 1030 1035 | 3424 |
| cag ttc aac atc agc cgc tac agt caa cag caa ctg atg gaa acc agc<br>Gln Phe Asn Ile Ser Arg Tyr Ser Gln Gln Gln Leu Met Glu Thr Ser<br>1040 1045 1050 | 3472 |
| cat cgc cat ctg ctg cac gcg gaa gaa ggc aca tgg ctg aat atc gac<br>His Arg His Leu Leu His Ala Glu Glu Gly Thr Trp Leu Asn Ile Asp<br>1055 1060 1065 | 3520 |
| ggt ttc cat atg ggg att ggt ggc gac gac tcc tgg agc ccg tca gta<br>Gly Phe His Met Gly Ile Gly Gly Asp Asp Ser Trp Ser Pro Ser Val<br>1070 1075 1080 | 3568 |
| tcg gcg gaa ttc cag ctg agc gcc ggt cgc tac cat tac cag ttg gtc<br>Ser Ala Glu Phe Gln Leu Ser Ala Gly Arg Tyr His Tyr Gln Leu Val<br>1085 1090 1095 | 3616 |
| tgg tgt caa aaa taagcttggc tgttttggcg gatgagagaa gattttcagc<br>Trp Cys Gln Lys<br>1100 | 3668 |
| ctgatacaga ttaaatcaga acgcagaagc ggtctgataa aacagaattt gcctggcggc | 3728 |
| agtagcgcgg tggtcccacc tgaccccatg ccgaactcag aagtgaaacg ccgtagcgcc | 3788 |
| gatggtagtg tggggtctcc ccatgcgaga gtagggaact gccaggcatc aaataaaacg | 3848 |
| aaaggctcag tcgaaagact gggcctttcg ttttatctgt tgtttgtcgg tgaacgctct | 3908 |
| cctgagtagg acaaatccgc cgggagcgga tttgaacgtt gcgaagcaac ggcccggagg | 3968 |
| gtggcgggca ggacgcccgc cataaactgc caggcatcaa attaagcaga aggccatcct | 4028 |
| gacggatggc cttttgcgt tctacaaac tcttttttgtt tatttttcta aatacattca | 4088 |
| aatatgtatc cgctcatgag acaataaccc tgataaatgc ttcaataata ttgaaaaagg | 4148 |
| aagagtatga gtattcaaca tttccgtgtc gcccttattc ccttttttgc ggcattttgc | 4208 |

```
cttcctgttt ttgctcaccc agaaacgctg gtgaaagtaa aagatgctga agatcagttg   4268
ggtgcacgag tgggttacat cgaactggat ctcaacagcg gtaagatcct tgagagtttt   4328
cgccccgaag aacgttttcc aatgatgagc acttttaaag ttctgctatg tggcgcggta   4388
ttatcccgtg ttgacgccgg gcaagagcaa ctcggtcgcc gcatacacta ttctcagaat   4448
gacttggttg agtactcacc agtcacagaa aagcatctta cggatggcat gacagtaaga   4508
gaattatgca gtgctgccat aaccatgagt gataacactg cggccaactt acttctgaca   4568
acgatcggag gaccgaagga gctaaccgct tttttgcaca acatggggga tcatgtaact   4628
cgccttgatc gttgggaacc ggagctgaat gaagccatac aaacgacga gcgtgacacc   4688 acgatgcctg tagcaatggc aacaacgttg cgcaaactat taactggcga actacttact   4748
ctagcttccc ggcaacaatt aatagactgg atggaggcgg ataaagttgc aggaccactt   4808
ctgcgctcgg cccttccggc tggctggttt attgctgata atctggagc cggtgagcgt   4868 gggtctcgcg gtatcattgc agcactgggg ccagatggta agccctcccg tatcgtagtt   4928
atctacacga cggggagtca ggcaactatg gatgaacgaa atagacagat cgctgagata   4988
ggtgcctcac tgattaagca ttggtaactg tcagaccaag tttactcata tactttag     5048 attgattaa aacttcattt ttaatttaaa aggatctagg tgaagatcct ttttgataat   5108
ctcatgacca aaatccctta acgtgagttt tcgttccact gagcgtcaga ccccgtagaa   5168
aagatcaaag gatcttcttg agatcctttt tttctgcgcg taatctgctg cttgcaaaca   5228
aaaaaaccac cgctaccagc ggtggtttgt ttgccggatc aagagctacc aactcttttt   5288
ccgaaggtaa ctggcttcag cagagcgcag ataccaaata ctgtccttct agtgtagccg   5348
tagttaggcc accacttcaa gaactctgta gcaccgccta catacctcgc tctgctaatc   5408
ctgttaccag tggctgctgc cagtggcgat aagtcgtgtc ttaccgggtt ggactcaaga   5468
cgatagttac cggataaggc gcagcggtcg ggctgaacgg ggggttcgtg cacacagccc   5528
agcttggagc gaacgaccta caccgaactg agatacctac agcgtgagct atgagaaagc   5588
gccacgcttc ccgaagggag aaaggcggac aggtatccgg taagcggcag gtcggaaca   5648 ggagagcgca cgagggagct ccaggggga aacgcctggt atctttatag tcctgtcggg   5708
tttcgccacc tctgacttga gcgtcgattt ttgtgatgct cgtcaggggg gcggagccta   5768
tggaaaaacg ccagcaacgc ggccttttta cggttcctgg ccttttgctg gccttttgct   5828
cacatgttct ttcctgcgtt atcccctgat tctgtggata accgtattac cgcctttgag   5888
tgagctgata ccgctcgccg cagccgaacg accgagcgca gcgagtcagt gagcgaggaa   5948
gcggaagagc gcctgatgcg gtattttctc cttacgcatc tgtgcggtat ttcacaccgc   6008
atatggtgca ctctcagtac aatctgctct gatgccgcat agttaagcca gtatacactc   6068
cgctatcgct acgtgactgg gtcatggctg cgccccgaca cccgccaaca cccgctgacg   6128
cgccctgacg ggcttgtctg ctcccggcat ccgcttacag acaagctgtg accgtctccg   6188
ggagctgcat gtgtcagagg ttttcaccgt catcaccgaa acgcgcgagg cagcagatca   6248
attcgcgcgc gaaggcgaag cggcatgcat aatgtgcctg tcaaatggac gaagcaggga   6308
ttctgcaaac cctatgctac tccgtcaagc cgtcaattgt ctgattcgtt accaattatg   6368
acaacttgac ggctacatca ttcactttt cttcacaacc ggcacggaac tcgctcgggc   6428
tggccccggt gcatttttta aatacccgcg agaaatagag ttgatcgtca aaaccaacat   6488
tgcgaccgac ggtggcgata ggcatccggg tggtgctcaa aagcagcttc gcctggctga   6548
tacgttggtc ctcgcgccag cttaagacgc taatccctaa ctgctggcgg aaaagatgtg   6608
```

-continued

```
acagacgcga cggcgacaag caaacatgct gtgcgacgct ggcgatatca aaattgctgt   6668
ctgccaggtg atcgctgatg tactgacaag cctcgcgtac ccgattatcc atcggtggat   6728
ggagcgactc gttaatcgct tccatgcgcc gcagtaacaa ttgctcaagc agatttatcg   6788
ccagcagctc cgaatagcgc ccttcccctt gcccggcgtt aatgatttgc ccaaacaggt   6848
cgctgaaatg cggctggtgc gcttcatccg ggcgaaagaa ccccgtattg gcaaatattg   6908
acggccagtt aagccattca tgccagtagg cgcgcggacg aaagtaaacc cactggtgat   6968
accattcgcg agcctccgga tgacgaccgt agtgatgaat ctctcctggc gggaacagca   7028
aaatatcacc cggtcggcaa acaaattctc gtccctgatt tttcaccacc ccctgaccgc   7088
gaatggtgag attgagaata taccttttca ttcccagcgg tcggtcgata aaaaaatcga   7148
gataaccgtt ggcctcaatc ggcgttaaac ccgccaccag atgggcatta aacgagtatc   7208
ccggcagcag gggatcattt tgcgcttcag ccatactttt catactcccg ccattcagag   7268
```

<210> SEQ ID NO 51
<211> LENGTH: 1103
<212> TYPE: PRT
<213> ORGANISM: Artificial Sequence
<220> FEATURE:
<223> OTHER INFORMATION: Description of Artificial Sequence: fusion
protein comprising a poly-histidine region, a nuclear localization
signal from SV40 large T antigen, a TAT signal sequence from HIV,
and the Beta-galactosidase protein from E. coli.

<400> SEQUENCE: 51

```
Met Gly Gly Ser His His His His His Gly Met Ala Ser Met Thr
 1               5                  10                  15

Gly Gly Gln Gln Met Gly Arg Asp Leu Tyr Asp Asp Asp Lys Asp
                20                  25                  30

Gln Leu Asp Met Ala Pro Lys Lys Arg Lys Gln Val Arg Tyr Gly
            35                  40                  45

Arg Lys Lys Arg Arg Gln Arg Arg Gln Val Pro Val Gly Glu Asp
        50                  55                  60

Gln Lys Gln His Leu Glu Leu Ser Arg Asp Ile Ala Gln Arg Phe Asn
 65                  70                  75                  80

Ala Leu Tyr Gly Glu Ile Asp Pro Val Val Leu Gln Arg Arg Asp Trp
                85                  90                  95

Glu Asn Pro Gly Val Thr Gln Leu Asn Arg Leu Ala Ala His Pro Pro
            100                 105                 110

Phe Ala Ser Trp Arg Asn Ser Glu Glu Ala Arg Thr Asp Arg Pro Ser
        115                 120                 125

Gln Gln Leu Arg Ser Leu Asn Gly Glu Trp Arg Phe Ala Trp Phe Pro
    130                 135                 140

Ala Pro Glu Ala Val Pro Glu Ser Trp Leu Glu Cys Asp Leu Pro Glu
145                 150                 155                 160

Ala Asp Thr Val Val Val Pro Ser Asn Trp Gln Met His Gly Tyr Asp
                165                 170                 175

Ala Pro Ile Tyr Thr Asn Val Thr Tyr Pro Ile Thr Val Asn Pro Pro
            180                 185                 190

Phe Val Pro Thr Glu Asn Pro Thr Gly Cys Tyr Ser Leu Thr Phe Asn
        195                 200                 205

Val Asp Glu Ser Trp Leu Gln Glu Gly Gln Thr Arg Ile Ile Phe Asp
    210                 215                 220

Gly Val Asn Ser Ala Phe His Leu Trp Cys Asn Gly Arg Trp Val Gly
```

```
            225                 230                 235                 240
Tyr Gly Gln Asp Ser Arg Leu Pro Ser Glu Phe Asp Leu Ser Ala Phe
                245                 250                 255
Leu Arg Ala Gly Glu Asn Arg Leu Ala Val Met Val Leu Arg Trp Ser
            260                 265                 270
Asp Gly Ser Tyr Leu Glu Asp Gln Asp Met Trp Arg Met Ser Gly Ile
            275                 280                 285
Phe Arg Asp Val Ser Leu Leu His Lys Pro Thr Thr Gln Ile Ser Asp
            290                 295                 300
Phe His Val Ala Thr Arg Phe Asn Asp Asp Phe Ser Arg Ala Val Leu
305                 310                 315                 320
Glu Ala Glu Val Gln Met Cys Gly Leu Arg Asp Tyr Leu Arg Val
                325                 330                 335
Thr Val Ser Leu Trp Gln Gly Glu Thr Gln Val Ala Ser Gly Thr Ala
            340                 345                 350
Pro Phe Gly Gly Glu Ile Ile Asp Glu Arg Gly Gly Tyr Ala Asp Arg
            355                 360                 365
Val Thr Leu Arg Leu Asn Val Glu Asn Pro Lys Leu Trp Ser Ala Glu
    370                 375                 380
Ile Pro Asn Leu Tyr Arg Ala Val Val Glu Leu His Thr Ala Asp Gly
385                 390                 395                 400
Thr Leu Ile Glu Ala Glu Ala Cys Asp Val Gly Phe Arg Glu Val Arg
                405                 410                 415
Ile Glu Asn Gly Leu Leu Leu Asn Gly Lys Pro Leu Leu Ile Arg
            420                 425                 430
Gly Val Asn Arg His Glu His His Pro Leu His Gly Gln Val Met Asp
            435                 440                 445
Glu Gln Thr Met Val Gln Asp Ile Leu Leu Met Lys Gln Asn Asn Phe
    450                 455                 460
Asn Ala Val Arg Cys Ser His Tyr Pro Asn His Pro Leu Trp Tyr Thr
465                 470                 475                 480
Leu Cys Asp Arg Tyr Gly Leu Tyr Val Val Asp Glu Ala Asn Ile Glu
                485                 490                 495
Thr His Gly Met Val Pro Met Asn Arg Leu Thr Asp Asp Pro Arg Trp
            500                 505                 510
Leu Pro Ala Met Ser Glu Arg Val Thr Arg Met Val Gln Arg Asp Arg
            515                 520                 525
Asn His Pro Ser Val Ile Ile Trp Ser Leu Gly Asn Glu Ser Gly His
            530                 535                 540
Gly Ala Asn His Asp Ala Leu Tyr Arg Trp Ile Lys Ser Val Asp Pro
545                 550                 555                 560
Ser Arg Pro Val Gln Tyr Glu Gly Gly Gly Ala Asp Thr Thr Ala Thr
                565                 570                 575
Asp Ile Ile Cys Pro Met Tyr Ala Arg Val Asp Glu Asp Gln Pro Phe
            580                 585                 590
Pro Ala Val Pro Lys Trp Ser Ile Lys Lys Trp Leu Ser Leu Pro Gly
            595                 600                 605
Glu Thr Arg Pro Leu Ile Leu Cys Glu Tyr Ala His Ala Met Gly Asn
    610                 615                 620
Ser Leu Gly Gly Phe Ala Lys Tyr Trp Gln Ala Phe Arg Gln Tyr Pro
625                 630                 635                 640
Arg Leu Gln Gly Gly Phe Val Trp Asp Trp Val Asp Gln Ser Leu Ile
                645                 650                 655
```

```
Lys Tyr Asp Glu Asn Gly Asn Pro Trp Ser Ala Tyr Gly Gly Asp Phe
            660                 665                 670

Gly Asp Thr Pro Asn Asp Arg Gln Phe Cys Met Asn Gly Leu Val Phe
        675                 680                 685

Ala Asp Arg Thr Pro His Pro Ala Leu Thr Glu Ala Lys His Gln Gln
        690                 695                 700

Gln Phe Gln Phe Arg Leu Ser Gly Gln Thr Ile Glu Val Thr Ser
705                 710                 715                 720

Glu Tyr Leu Phe Arg His Ser Asp Asn Glu Leu Leu His Trp Met Val
                725                 730                 735

Ala Leu Asp Gly Lys Pro Leu Ala Ser Gly Glu Val Pro Leu Asp Val
            740                 745                 750

Ala Pro Gln Gly Lys Gln Leu Ile Glu Leu Pro Glu Leu Pro Gln Pro
        755                 760                 765

Glu Ser Ala Gly Gln Leu Trp Leu Thr Val Arg Val Val Gln Pro Asn
    770                 775                 780

Ala Thr Ala Trp Ser Glu Ala Gly His Ile Ser Ala Trp Gln Gln Trp
785                 790                 795                 800

Arg Leu Ala Glu Asn Leu Ser Val Thr Leu Pro Ala Ala Ser His Ala
                805                 810                 815

Ile Pro His Leu Thr Thr Ser Glu Met Asp Phe Cys Ile Glu Leu Gly
            820                 825                 830

Asn Lys Arg Trp Gln Phe Asn Arg Gln Ser Gly Phe Leu Ser Gln Met
        835                 840                 845

Trp Ile Gly Asp Lys Lys Gln Leu Leu Thr Pro Leu Arg Asp Gln Phe
850                 855                 860

Thr Arg Ala Pro Leu Asp Asn Asp Ile Gly Val Ser Glu Ala Thr Arg
865                 870                 875                 880

Ile Asp Pro Asn Ala Trp Val Glu Arg Trp Lys Ala Ala Gly His Tyr
                885                 890                 895

Gln Ala Glu Ala Ala Leu Leu Gln Cys Thr Ala Asp Thr Leu Ala Asp
            900                 905                 910

Ala Val Leu Ile Thr Thr Ala His Ala Trp Gln His Gln Gly Lys Thr
        915                 920                 925

Leu Phe Ile Ser Arg Lys Thr Tyr Arg Ile Asp Gly Ser Gly Gln Met
    930                 935                 940

Ala Ile Thr Val Asp Val Glu Val Ala Ser Asp Thr Pro His Pro Ala
945                 950                 955                 960

Arg Ile Gly Leu Asn Cys Gln Leu Ala Gln Val Ala Glu Arg Val Asn
                965                 970                 975

Trp Leu Gly Leu Gly Pro Gln Glu Asn Tyr Pro Asp Arg Leu Thr Ala
            980                 985                 990

Ala Cys Phe Asp Arg Trp Asp Leu Pro Leu Ser Asp Met Tyr Thr Pro
        995                 1000                1005

Tyr Val Phe Pro Ser Glu Asn Gly Leu Arg Cys Gly Thr Arg Glu Leu
    1010                1015                1020

Asn Tyr Gly Pro His Gln Trp Arg Gly Asp Phe Gln Phe Asn Ile Ser
1025                1030                1035                1040

Arg Tyr Ser Gln Gln Gln Leu Met Glu Thr Ser His Arg His Leu Leu
                1045                1050                1055

His Ala Glu Glu Gly Thr Trp Leu Asn Ile Asp Gly Phe His Met Gly
            1060                1065                1070
```

```
Ile Gly Gly Asp Asp Ser Trp Ser Pro Ser Val Ser Ala Glu Phe Gln
        1075                1080                1085

Leu Ser Ala Gly Arg Tyr His Tyr Gln Leu Val Trp Cys Gln Lys
    1090                1095                1100

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 52
aggatcctat ggtcgtaaga aacgt                                       25

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 53
agaattcctg gaatactgta actgt                                       25

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 54
agaattcatg gagaacactg aaaac                                       25

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 55
agtcgactta gtgataaaaa tagag                                       25
```

POLYPEPTIDE FOR UNSTABILIZING PROTEIN IN CELLS UNDER AEROBIC CONDITIONS AND DNA ENCODING THE SAME

RELATED APPLICATIONS

This application is U.S. National Phase of International Application PCT/JP2002/005482, filed Jun. 4, 2002 designating the U.S., and published in English as WO 2002/099104 on Dec. 12, 2002, which claims priority to Japanese Patent Application No. 2001-169948, filed Jun. 5, 2001 and Japanese Patent Application No. 2001-169949, filed Jun. 5, 2001.

TECHNICAL FIELD

The present invention relates to a polypeptide for unstabilizing a protein in a cell under aerobic conditions, DNA encoding the polypeptide and a method using the DNA. The present invention also relates to a vector, which comprises the DNA and is capable of expressing a fused protein having stability dependent on oxygen conditions in a cell.

Further, the present invention relates to a fused protein containing the above polypeptide and having protein transduction activity through cell membrane and stability dependent on oxygen conditions in a cell and a method of using the fused protein. The present invention also relates to a vector capable of expressing the fused protein.

The present invention is useful in the fields of the microbiological industry, medicinal drugs, medical care, and, the like.

BACKGROUND ART

The partial pressure of oxygen in a solid tumor is not uniform, and tumor cells are exposed to various oxygen environments. This results from the fact that the scattering distance of oxygen molecules from a blood vessel to the tissue of a tumor is limited. In the field of radiobiology, the inside of a solid tumor is divided into three regions, that is, 1) an aerobic region, 2) a dead region and 3) an hypoxic region according to the amount of oxygen supplied to each tumor cell.

1) Since an extremely large number of oxygen molecules are supplied to each tumor cell at a distance from a capillary vessel of up to 70 µm, this region is called "an aerobic region". Oxygen molecules are indispensable for the acquisition of the effect of radiotherapy for solid tumors. Therefore, it is known that the aerobic region rich in oxygen molecules literally is a region having extremely high radiation sensitivity. The treatment effect of chemotherapy for the aerobic region is considered to be high because an anti-cancer drug is easily scattered from a blood vessel system to the aerobic region when chemotherapy is performed.

2) Oxygen molecules released from the blood vessel are consumed by tumor cells in the aerobic region while the molecules are scattered. Therefore, oxygen molecules required for survival of tumor cells existent in a region far from the capillary vessel are not supplied to the cells. As a result, tumor cells far from the blood vessel system at a distance of 70 µm or more die, thereby forming a dead region.

3) A hypoxic region composed of hypoxic cells is existent between the aerobic region and the dead region. The minimum amount of oxygen molecules required for the survival of tumor cells is supplied to the hypoxic region. However, oxygen molecules enough to obtain the effect of radiotherapy are not supplied. Therefore, the hypoxic region in the tumor has extremely low radiation sensitivity, which is considered to be one of the causes of the re-proliferation of tumor cells after the end of radiotherapy. Since the amount of an anti-cancer drug scattered from the blood vessel system to the hypoxic region is limited when a chemical treatment is performed, a satisfactory treatment effect cannot be expected in fact.

It has been difficult to confirm the existence of such a hypoxic cell. This is because there has been substantially no means of monitoring the existence of oxygen in a cell. Known as means of monitoring the hypoxic cells are a method of measuring an oxygen voltage of a cell using micro-electrodes, immunocytostaining using Pimonidazole (Hypoxyprobe-1) known as a hypoxic cell indicator, immunocytostaining using a gene product whose expression is induced in a cell under hypoxic conditions as a label, and the like. However, the above methods are technically difficult, and at present, also apparatuses for carrying out these are complex and not generally used. That is, the development of general-purpose means of detecting hypoxic cells has been desired.

As described above, in cancer treatment, the existence of hypoxic cancer cells hinders the treatment by radiotherapy or chemotherapy drug. Means of removing these cells effectively has been desired. Although only the use of a combination of a hypoxic cell radiation sensitizer and radiotherapy has been known to cope with the hypoxic cells, only one drug is now in a clinical trial stage and there does not currently exist a hypoxic cell radiation sensitizer which has been put to practical use. This results from the fact that 2-nitroimidazole which is the mother nucleus of the hypoxic cell radiation sensitizer is neurotoxic and it is difficult to control its toxicity and medical effect. That is, the development of means of getting rid of a hypoxic cancer cell effectively has been desired.

By the way, the expression of physiologically important genes such as a vascular endothelial growth factor (VEGF) and erythropoietin (EPO) is induced in a cell under a hypoxic environment. The expression of these genes is induced by hypoxia-inducible factor-1 complex (hereinafter, referred to as HIF-1) in a transfer level.

HIF-1 is a heterodimer consisting of HIF-1α protein and HIF-1β protein. These sub-units each have a domain for binding to DNA called "basic-helix-loop-helix domain (bHLH domain)" and a domain for forming a heterodimer called "PER-aryl hydrocarbon nuclear translocator (ARNT)-SIM (PAS) domain" at $N$ termini. It has been found that the HIF-1α protein has two transactivation domains, that is, N- and C-transactivation domains (N-TAD, C-TAD).

The activation mechanism dependent on the oxygen concentration of HIF-1 has recently been clarified. The transfer and translation of HIF-1β mRNA are always activated and its gene product (protein) is always expressed non-dependent on the partial pressure of oxygen in the outside world. Although the transfer and translation of HIF-1α mRNA are also always activated, the biosynthesized HIF-1α protein is positively degraded under aerobic conditions and is existent stably only under hypoxic conditions.

It has thus been found that the stability of the HIF-1α protein is controlled dependent on the concentration of oxygen in the outside world and that the transfer activity of HIF-1 is controlled dependent mainly on the amount of the protein.

To date, it has been reported that the 401a.a.-603a.a. domain is important for the stabilization of HIF-1α under hypoxic conditions in experiments using a partially deleted mutant of HIF-1α (Huang L E, Gu J, Schau M and Bunn H F. 1998. Regulation of hypoxia-inducible factor 1 alpha is mediated by an $O_2$-dependent degradation domain via. the ubiquitin-proteasome pathway. Proc. Natl. Acad. Sci. USA.

95:7987-7992: document 1). This domain is called "an Oxygen Dependent Degradation domain" (ODD domain).

It has been known that the oxygen dependent stability of HIF-1α suggests that amino acid residues in this domain be modified dependent on oxygen under aerobic conditions, be ubiquitinated in the end, and be degraded by proteasome (Huang, L. E., Gu, J. Schau, M. and Bunn, H. F. Regulation of hypoxia-inducible factor 1α is mediated by an $O_2$-dependent degradation domain via the ubiquitin-proteasome pathway. Proc. Natl. Acad. Sci. USA. 95: 7987-7992, 1998).

Therefore, it has also been known that HIF-1α can obtain the same stability as that under hypoxic conditions by culturing HIF-1α in a medium containing a proteasome inhibitor such as N-carbobenzoxyl-L-leucinyl-L-leucinyl-L-norvalinal (to be abbreviated as "Cbz-LLL" hereinafter) (Rock, K. L., Gramm, C., Rothstein, L., Clark, K., Stein, R., Dick, L., Hwang, D. and Goldberg, A. L. Inhibitors of the proteasome block the degradation of most cell proteins and the generation of peptides presented on MHC class I molecules. Cell 78: 761-771, 1994: document 3). And this is disclosed (Sutter, C. H., Laughner, E. and Semenza, G. L. Hypoxia-inducible factor 1α protein expression is controlled by oxygen-regulated ubiquitination that is disrupted by deletions and missense mutations. Proc. Natl. Acad. Sci. USA. 97: 4748-4753, 2000: document 4). Through this fact, it has been assumed that the degradation of a fused protein containing the polypeptide is carried out through a degradation mechanism by ubiquitin-proteasome like HIF-1α and that the fused protein is stabilized under hypoxic conditions and in a medium containing Cbz-LLL.

It has been reported that the Gal-4 protein fused with 530a.a.-652a.a. of the HIF-1α protein is controlled to be positively degraded in a cultured cell only when the concentration of oxygen is high (Vickram Srinivas, Li-Ping Zhang, Xiao-Hong Zhu and Jaime Caro. 1999. Characterization of an Oxygen/Redox-Dependent Degradation Domain of Hypoxia-Inducible Factorα (HIFα) Proteins. Biochem. Biophy. Res. Com. 260: 557-561: document 5). It has also been reported that when HIF-1α561a.a.-568a.a. in a gene fused with Gal-4 and 529a.a-826a.a. of HIF-1α is substituted by the alanine residue, the above control is lost. It is presumed, from this fact, that the domain around 561a.a.-568a.a. of HIF-1α where the HIF-1α of a mouse and human HIF-1α are well kept takes part in the oxygen concentration dependent stabilization of a protein. It is also discussed whether the 557a.a.-571a.a. domain of HIF-1α plays an important role in the control of the stability of the HIF-1α protein (above document 5).

However, the inventors of the present invention have found it impossible to make the stabilization of a fused protein dependent on the concentration of oxygen only with the 557a.a.-571a.a. domain. It cannot be said that the domain taking part in the stabilization of a fused protein of the HIF-1α protein is identified.

It was reported in 1988 that a protein called "TAT" derived from a human immunodeficiency virus (HIV) has the activity of transducing a protein through cell membrane (Cell; 55, 1179 (1988), Proc. Natl. Acad. Sci. USA; 91, 664 (1994)). After that, it was elucidated that a domain consisting of only 11 amino acids of TAT protein (TAT protein transduction domain) has the above activity. At the same time, it was also reported that β-galactosidase protein fused with this TAT protein transduction domain is introduced into a cell.

However, the relationship between the above HIF-1α and TAT and the relationship between HIF-1α and a protein having protein transduction activity through membrane have been unknown so far. Therefore, it has been unknown that when the HIF-1α protein having a specific region for controlling the stabilization of the HIF-1α protein, a protein having protein transduction activity through membrane and other protein are fused together, making use of the specific region, the obtained fused protein can be introduced into a cell and that in the cell harboring the fused protein, oxygen-dependent stability can be imparted to the fused protein.

DISCLOSURE OF THE INVENTION

The present invention has been made under the above situation, and it is an object of the present invention to identify a region of HIF-1α protein which can control the stability of any protein depending on the concentration of oxygen by fusing the protein and to control the expression of a specific gene and the expression of a fused protein corresponding to the gene according to the amount of oxygen by making use of the region.

It is another object of the present invention to provide a fused protein which comprises a protein having a region taking part in the stabilization of specified HIF-1α protein and has protein transduction activity through cell membrane and stability dependent on oxygen conditions in a cell and a method of controlling a fused protein, the method allowing the fused protein to be introduced into a cell advantageously and the stability of the fused protein to be adjusted according to the amount of oxygen in the fused protein-introduced cell.

It is still another object of the present invention to provide a vector capable of expressing the fused proteins.

The inventors of the present invention have conducted intensive studies to attain the above objects and have found that a region having the amino acid sequence of SEQ ID NO: 1 of the amino acid sequences of HIF-1α protein is a key part of a signal when a protein fused with the above region is degraded under aerobic conditions.

The inventors have also found that a fused protein containing HIF-1α protein having the above specific region and a protein having protein transduction activity through membrane is advantageously introduced into a cell. The present invention has been accomplished based on those findings.

That is, the present invention is as follows.

(1) A DNA encoding a polypeptide (A) or (B):

(A) a polypeptide having the amino acid sequence of SEQ ID NO: 1

(B) a polypeptide having an amino acid sequence comprising at least 16 amino acid residues in the amino acid sequence of SEQ ID NO: 1, and imparting stability dependent on an oxygen concentration to other protein in a cell harboring a fused protein, when the polypeptide is fused with a nuclear localization signal and the other protein to form the fused protein.

(2) The DNA according to (1), wherein the fused protein is stabilized to a larger extent in a cell under hypoxic conditions than under aerobic conditions.

(3) The DNA according to (1) or (2) which has the nucleotide sequence of SEQ ID NO: 2 or part thereof.

(4) A vector which comprises a DNA encoding a nuclear localization signal and a DNA encoding a polypeptide according to any one of (1) to (3), and which is capable of expressing a fused protein comprising the nuclear localization signal, the polypeptide, and other protein when a DNA encoding the other protein is inserted into these DNAs.

(5) The vector according to (4) which comprises the DNA encoding the other protein.

(6) The vector according to (5) which can unstabilize the fused protein in a cell harboring the vector under aerobic conditions.

(7) The vector according to (6), wherein the other protein is a labeling protein and/or a protein having cytotoxicity.

(8) A cell into which the vector according to any one of (4) to (7) is introduced.

(9) The cell according to (8) which is a cell of a microorganism.

(10) The microorganism according to (9) which is *Escherichia coli*.

(11) A method of detecting a cell under hypoxic conditions, comprising: monitoring an existence state of the other protein which is a labeling protein in a cell harboring the vector according to (7).

(12) A method of controlling the existence of a protein in a cell, comprising: introducing the vector according to (6) into the cell; and expressing a fused protein to be encoded by the vector.

(13) A method of controlling the existence of a protein in a cell harboring a DNA encoding the protein, comprising: connecting the DNA encoding a nuclear localization signal and the DNA according to (1) to the DNA; and expressing a fused protein containing the nuclear localization signal, a polypeptide to be encoded by the DNA according to (1), and the protein.

(14) The method according to (13), wherein the fused protein is controlled to be existent in a cell under hypoxic conditions and not to be existent under aerobic conditions.

(15) A method of inhibiting growth of a cell under hypoxic conditions, comprising: allowing the cell to harbor the vector according to (7) in which the other protein is a protein having cytotoxicity so that the fused protein encoded by the vector exists in the cell under hypoxic conditions.

(16) A fused protein comprising a nuclear localization signal, a protein having protein transduction activity through membrane, a polypeptide (A) or (B), and other protein, the fused protein having protein transduction activity through cell membrane and stability dependent on oxygen conditions in a cell:

(A) a polypeptide having the amino acid sequence of SEQ ID NO: 1

(B) a polypeptide having an amino acid sequence comprising at least 16 amino acid residues in the amino acid sequence of SEQ ID NO: 1 and imparting stability dependent on an oxygen concentration to other protein in a cell harboring a fused protein, when the polypeptide is fused with a nuclear localization signal and the other protein to form the fused protein.

(17) The fused protein according to (16), wherein the protein having protein transduction activity through membrane is a protein (C) or (D) having a TAT signal sequence (TAT) derived from HIV:

(C) a protein having the amino acid sequence of SEQ ID NO: 4

(D) a protein having an amino acid sequence comprising at least 9 amino acid residues in the amino acid sequence of SEQ ID NO: 4 and imparting protein transduction activity through membrane to the fused protein.

(18) A fused protein comprising a polypeptide (A) or (B1), a protein (C) or (D) having a TAT signal sequence (TAT) derived from HIV, and other protein, the fused protein having protein transduction activity through cell membrane and stability dependent on oxygen conditions in a cell:

(A) a polypeptide having the amino acid sequence of SEQ ID NO: 1

(B1) a polypeptide having an amino acid sequence comprising at least 16 amino acid residues in the amino acid sequence of SEQ ID NO: 1, and imparting stability dependent on an oxygen concentration to other protein in a cell harboring a fused protein, when the polypeptide is fused with a TAT protein and the other protein to form the fused protein (C) a protein having the amino acid sequence of SEQ ID NO: 4

(D) a protein having an amino acid sequence comprising at least 9 amino acid residues in the amino acid sequence of SEQ ID NO: 4 and imparting protein transduction activity through membrane to a fused protein.

(19) The fused protein according to any one of (16) to (18), which exists more stably in a cell under hypoxic conditions than under aerobic conditions.

(20) The fused protein according to any one of (16) to (19), wherein the other protein is a labeling protein and/or a protein having cytotoxicity.

(21) A method of controlling the existence of a fused protein, comprising: allowing the fused protein according to (16) or (18) to be transduced into a cell from the outside of the cell; and controlling stability of the fused protein according to oxygen conditions in the transduced cell.

(22) The method of controlling the existence of a fused protein according to (21), wherein the fused protein is made existent more stably in a cell under hypoxic conditions than under aerobic conditions.

(23) A vector which comprises a DNA encoding a nuclear localization signal, a DNA encoding a protein having protein transduction activity through membrane, and a DNA encoding a polypeptide (A) or (B), and which is capable of expressing a fused protein comprising the nuclear localization signal, the protein having protein transduction activity through membrane, the polypeptide, and other protein when a DNA encoding the other protein is inserted into these DNAs:

(A) a polypeptide having the amino acid sequence of SEQ ID NO: 1

(B) a polypeptide having an amino acid sequence comprising at least 16 amino acid residues in the amino acid sequence of SEQ ID NO: 1 and imparting stability dependent on an oxygen concentration to other protein in a cell harboring a fused protein, when the polypeptide is fused with a nuclear localization signal and the other protein to form the fused protein.

(24) The vector according to (23), wherein the protein having protein transduction activity through membrane is a protein (C) or (D) having a TAT signal sequence (TAT) derived from HIV:

(C) a protein having the amino acid sequence of SEQ ID NO: 4

(D) a protein having an amino acid sequence comprising at least 9 amino acid residues in the amino acid sequence of SEQ ID NO: 4 and imparting protein transduction activity through membrane to the fused protein.

(25) A vector which comprises a DNA encoding a polypeptide (A) or (B1) and a DNA encoding a protein (C) or (D) having a TAT signal sequence (TAT) derived from: HIV and which is capable of expressing a fused protein comprising a TAT protein, the polypeptide, and other protein when a DNA encoding the other protein is inserted into these DNAs:

(A) a polypeptide having the amino acid sequence of SEQ ID NO: 1

(B1) a polypeptide having an amino acid sequence comprising at least 16 amino acid residues in the amino acid sequence of SEQ ID NO: 1, and imparting stability dependent on an oxygen concentration to other protein in a cell harboring a fused protein, when the polypeptide is fused with a TAT protein and the other protein to form the fused protein (C) a protein having the amino acid sequence of SEQ ID NO: 4

(D) a protein having an amino acid sequence comprising at least 9 amino acid residues in the amino acid sequence of SEQ ID NO: 4 and imparting protein transduction activity through membrane to the fused protein.

(26) The vector according to any one of (23) to (25), wherein the fused protein exists more stably in a cell under hypoxic conditions than under aerobic conditions.

(27) The vector according to any one of (23) to (25), wherein the DNA encoding a polypeptide has the nucleotide sequence of SEQ ID NO: 2 or part thereof.

(28) The vector according to any one of (23) to (25), wherein the DNA encoding a TAT protein has the nucleotide sequence of SEQ ID NO: 5 or part thereof.

(29) The vector according to any one of (23) to (28) which comprises the DNA encoding the other protein.

(30) The vector according to (29), wherein the other protein is a labeling protein and/or a protein having cytotoxicity.

The present invention will be detailed hereinbelow.

DNA which is a first aspect of the present invention is DNA encoding a polypeptide having the amino acid sequence of SEQ ID NO: 1. When the polypeptide is fused with a nuclear localization signal (to be abbreviated as NLS hereinafter) and another protein, the polypeptide provides stability dependent on an oxygen concentration to the other protein in a cell harboring the fused protein.

The above fused protein is held more stably when the cell harboring the fused protein is under hypoxic conditions than under aerobic conditions. The fused protein is degraded more quickly in the cell under aerobic conditions than under hypoxic conditions.

In the present invention, the term "hypoxic conditions" refers to a state where the partial pressure of oxygen is about 20 mmHg or less in vivo. For example, the culture of a cell in an incubator whose oxygen concentration is set to 1% or less is under hypoxic conditions. The term "aerobic conditions" refers to a state where the partial pressure of oxygen is higher than about 20 mmHg in vivo.

DNA of the first aspect of the present invention may be part of above-mentioned DNA as far as the polypeptide to be encoded by the DNA can provide stability dependent on an oxygen concentration in a cell as described above to a fused protein containing the polypeptide. Specifically, the polypeptide is a polypeptide having an amino acid sequence comprising at least 16 continuous amino acid residues in the amino acid sequence of SEQ ID NO: 1, preferably at least 17, more preferably at least 18. More specifically, the polypeptide is a polypeptide having an amino acid sequence comprising 16 or more amino acid residues in the amino acid sequence of SEQ ID NO: 1 and 120 or less amino acid, preferably 17 or more and 50 or less amino acid, more preferably 18 or more and 30 or less amino acid, particularly preferably 18 or more and 20 or less. Much more specifically, the polypeptide has the amino acid sequence consisting of amino acid Nos. 1 to 16 or of amino acid Nos. 3 to 18 in the amino acid sequence of SEQ ID NO: 1.

The polypeptide to be encoded by the DNA of the first aspect of the present invention may have an amino acid sequence including the substitution, deletion, or insertion of one or few amino acid residues in the amino acid sequence consisting of 15 or more and 20 or less continuous amino acid residues in the amino acid sequence of SEQ ID NO: 1 or an amino acid sequence having a homology of 85% or more with the polypeptide of the amino acid sequence of SEQ ID NO: 1 as far as the polypeptide can impart stability dependent on an oxygen concentration in a cell as described above to a fused protein containing the polypeptide. The tyrosine residue corresponding to the tyrosine residue of the amino acid No. 9 of the sequence of SEQ ID NO: 1 must be kept.

NLS has an amino acid sequence which is required for a protein to be localized in the nucleus of a eukaryotic cell having a nuclear membrane structure in the cell. That is, a protein having the above sequence is transported to the nucleus through a nuclear membrane. NLS has an amino acid sequence which is seen in a protein having activity in a nucleus, such as a DNA binding protein.

In the first aspect of the present invention, NLS is not particularly limited as long as a fused protein has the activity of transmigrating to the nucleus in a cell harboring the fused protein when the NLS is fused with a polypeptide to be encoded by the DNA of the first aspect of the present invention and other protein. The NLS is, for example, NLS (126a.a. to 132a.a. domain of large-T antigen) derived from the simian virus 40 (SV40) large-T antigen (Proc. Natl. Acad. Sci. (1989) 86:9327-9331: document 7). HIF-1α includes specific NLS, and this NLS may also be used.

The other protein is not particularly limited as long as the protein is used in the aim to control stability dependent on an oxygen concentration in a cell. The protein is, for example, a labeling protein or a protein having cytotoxicity.

Examples of the labeling protein include enzymes for catalyzing a color development reaction such as β-galactosidase, horseradish peroxidase and alkali phosphatase. The color development reactions of these are well known as enzyme immunoassay or a technique for investigating the existence of a protein in a cell in the fields of antibodies and microbiology. A protein having fluorescence such as green fluorescence protein (GFP) may be used as the above protein.

Examples of the protein having cytotoxicity include a toxic protein of thymidine kinase of a herpes simplex virus and an apoptosis inducible factor.

DNA of the first aspect of the present invention is not particularly limited as long as the amino acid sequence to be encoded satisfies the above conditions. Specifically, it is DNA having the nucleotide sequence of SEQ ID NO:2 or part thereof.

DNA of the first aspect of the present invention can be chemically synthesized according to a general chemical synthesis method based on the amino acid sequence to be encoded thereby. The amino acid sequence of HIF-1α or the nucleotide sequence of cDNA obtained by encoding the amino acid sequence thereof is already known (Gene Bank Accession No. U22431), and the DNA can also be obtained by amplification from the chromosome DNA or cDNA library of humans or animals such as mice by a polymerase chain reaction (PCR) using oligonucleotide prepared based on these sequences and nucleotide sequence of SEQ ID NO: 2 as a primer. Examples of the primer include various primers shown in Examples. When a sequence encoding NLS, a sequence required for the expression of a gene (such as a Kozak sequence), or a sequence which a restriction enzyme recognises is included in the sequence of the primer, the preparation of DNA encoding a fused protein becomes easy.

When the amplified product obtained by PCR is integrated into a host vector suitable for the recombination of a gene such as *Escherichia coli*, the subsequent operation becomes easy. An example of the vector is pBluescript II (TOYOBO).

The vector of the first aspect of the present invention is a vector which comprises DNA encoding NLS and DNA encoding a polypeptide of the first aspect of the present invention and which is capable of expressing a fused protein of a nuclear localization signal, the above polypeptide, and other protein by inserting DNA encoding other protein into these DNAs.

In the above vector, the DNA encoding a polypeptide is, specifically, DNA having the nucleotide sequence of SEQ ID NO: 2 or part thereof.

The DNA encoding NLS is, for example, DNA having the nucleotide sequence of SEQ ID NO: 6 or part thereof.

Another example of the vector of the first aspect of the present invention is a vector which comprises DNA encoding other protein, DNA encoding NLS, and DNA encoding a polypeptide according to the first aspect of the present invention, as described above to express a fused protein. The fused protein comprises NLS, the polypeptide according to the first aspect of the present invention, and other protein in this order from the N terminus. That is, in the vector of the first aspect of the present invention, DNAs encoding a polypeptide and a protein are connected to each other in such a manner that their frames are adjusted with each other, and further an expression control sequence such as a promoter required for the expression of a gene is contained.

The promoter includes, for example, an SV40 early promoter and lac promoter.

The cell of the first aspect of the present invention is a cell into which the vector of the first aspect of the present invention has been introduced. The cell may be the cell of a microorganism. Examples of the microorganism include: bacteria such as *Escherichia coli*; yeast such as *Saccharomyces cerevisiae*, filamentous fungi such as *Aspergillus nidulans*; and the cultured cells of animals or plants. To introduce the vector of the first aspect of the present invention into those cells, ordinary transformation may be used.

*Escherichia coli* DH5αIQ/PCH557-574 harboring the plasmid pCH/557-574 as an example of the vector containing the DNA of the first aspect of the present invention as will be shown in Example has been deposited at National Institute of Advanced Industrial Science and Technology, International Patent Organism Depositary (Central 6, 1-1-1 Higashi, Tsukuba, Ibaraki, 305-8566 Japan) (formerly, National Institute of Bioscience and Human-Technology, Agency of Industrial Science and Technology (1-1-3 Higashi, Tsukuba, Ibaraki, 305-8566 Japan)) under the accession number FERM P-18193 on Feb. 1, 2001.

The above *Escherichia coli* DH5αIQ/PCH557-574 harboring the pCH/557-574 plasmid has been transferred to international depositary at the above International Patent Organism Depositary of National Institute of Advanced Industrial Science and Technology which is an independent administrative institution (Central 6, 1-1-1 Higashi, Tsukuba, Ibaraki, 305-8566 Japan) as accession number FERM BP-7828 on Dec. 17, 2001.

A description is subsequently given of the method of utilizing a fused protein containing a polypeptide encoded by the DNA of the first aspect of the present invention.

The existence state of the fused protein of the first aspect of the present invention which is prepared by fusing together a nuclear localization signal, a polypeptide to be encoded by the DNA of the first aspect and other protein differs according to oxygen conditions in a cell.

Stated more specifically, the fused protein is existent stably in the cell under hypoxic conditions and is positively degraded in the cell under aerobic conditions.

Therefore, when the vector of the first aspect is introduced into a cell to express a fused protein to be encoded by the vector, the existence of a protein forming the fused protein of the first aspect can be controlled according to oxygen conditions in the cell.

Stated more specifically, a protein can be stably held by placing the cell under hypoxic conditions and the amount of a protein can be reduced by placing the cell under aerobic conditions.

When the vector of the first aspect which uses a labeling protein as other protein is held in the cell to express the fused protein of the first aspect containing the labeling protein and to monitor the labeling protein with the label as an index, in other words, to monitor the existence state of the fused protein of the first aspect, a cell under hypoxic conditions can be detected. Particularly when a protein which can be visualized as a label is used, a hypoxic cell can be visualized.

When the vector of the first aspect which uses a protein having cytotoxicity as other protein is held in a cell and the fused protein of the first aspect containing a protein having cytotoxicity is expressed in the cell, the growth of the cell under hypoxic conditions can be inhibited. More specifically, DNA encoding the fused protein of the first aspect is inserted into a retrovirus or adenovirus and the whole is administered into the body, a toxic protein can be expressed only in a hypoxic region in a tumor which is an issue in the scene of cancer treatment. Therefore, a cell under hypoxic conditions can be selectively removed, which may lead to the development of a new remedy for cancer.

A description is subsequently given of the fused protein of the second aspect of the present invention which is a fused protein containing the polypeptide according to the first aspect and having protein transduction activity through cell membrane and stability dependent on oxygen conditions in a cell.

The fused protein of the second aspect comprises NLS, a protein having protein transduction activity through membrane, other protein, and a polypeptide which imparts stability dependent on an oxygen concentration to the other protein in a cell harboring a fused protein obtained by fusing NLS and the other protein together. The fused protein can be transduced into the cell from the outside of the cell and has stability which differs according to oxygen conditions in the cell.

As the polypeptide in the fused protein of the second aspect, a polypeptide to be encoded by the above DNA of the first aspect, that is, the same polypeptide as the polypeptide in the fused protein of the first aspect may be used. More specifically, the polypeptide is a polypeptide having the amino acid sequence of SEQ ID NO: 1. As far as the polypeptide can impart stability dependent on an oxygen concentration in a cell, the polypeptide may have part of the amino acid sequence of SEQ ID NO: 1. The index for this part is described in the section of the above polypeptide to be encoded by the DNA of the first aspect.

The polypeptide in the fused protein of the second aspect is particularly preferably a polypeptide in the fused protein of the first aspect, that is, a polypeptide corresponding to the specific 557a.a.-574a.a. domain of HIF-1α having the sequence of SEQ ID NO: 1. The polypeptide in the fused protein of the second aspect has only to have the above specific domain. For example, a polypeptide corresponding to the 401a.a.-603a.a. domain of HIF-1α, preferably a polypeptide corresponding to the 548a.a.-603a.a. domain of HIF-1α may be used.

As NLS used in the fused protein of the second aspect, NLS the same NLS as NLS in the fused protein of the first aspect may be used.

The protein having protein transduction activity through membrane used in the fused protein of the second aspect is not particularly limited as long as the protein is a protein which imparts activity for transducing a protein through cell membrane to a fused protein obtained by being fused with the above polypeptide and other protein but the protein is preferably TAT, the third alpha-helix of *Antennapedia homeodomain*, VP22 protein from herpes simplex virus, or the like.

TAT is a protein having activity for transducing a protein through cell membrane derived from human immunodeficiency virus (HIV). More specifically, TAT is a protein having the amino acid sequence of SEQ ID NO: 4.

TAT as used in the present invention may have part of the amino acid sequence of SEQ ID NO: 4 as far as TAT has activity for transducing a protein through cell membrane. Specifically, TAT may be a protein having an amino acid sequence consisting of at least 9 amino acid residues in the amino acid sequence of SEQ ID NO: 4. More specifically, TAT may be a protein having the amino acid sequence consisting of amino acid Nos. 3 to 11 of the sequence of SEQ ID NO: 4.

As the other protein used in the fused protein of the second aspect, the same protein as the above-described other protein in the fused protein of the first aspect may be used. The other protein is, for example, a labeling protein or a protein having cytotoxicity like the above other protein.

Another example of the fused protein of the second aspect is a fused protein which comprises the above TAT, other protein, and a polypeptide which imparts stability dependent on an oxygen concentration to the other protein in a cell harboring the fused protein obtained by fusing TAT with the other protein. The fused protein can be transduced into the cell from the outside of the cell and has stability which differs according to oxygen conditions in the cell.

When the above TAT is used as the protein having protein transduction activity through membrane, a fused protein having protein transduction activity through cell membrane and stability dependent on oxygen conditions in a cell is obtained even though the protein does not have NLS. That is, when TAT is used as the protein having protein transduction activity through membrane, regardless of the existence of NLS, the fused protein of the second aspect is obtained.

The polypeptide and other protein in another example of the fused protein of the second aspect of the present invention have already been described in the section of the fused protein of the second aspect of the present invention.

The vector of the second aspect of the present invention is a vector capable of expressing the fused protein of the second aspect. Specifically, the vector is a vector which comprises DNA encoding NLS, DNA encoding a protein having protein transduction activity through membrane, and DNA encoding a polypeptide imparting stability dependent on oxygen concentration to the other protein in a cell harboring a fused protein obtained by fusing NLS with the other protein and which is capable of expressing a fused protein containing a nuclear localization signal, a protein having protein transduction activity through membrane, the above polypeptide, and other protein by inserting DNA encoding the other protein into these DNAs.

Another example of the vector of the second aspect of the present invention is a vector which comprises DNA encoding TAT and DNA encoding a polypeptide imparting stability dependent on an oxygen concentration to other protein in a cell harboring a fused protein obtained by fusing TAT with the other protein and which is capable of expressing a fused protein containing TAT, the above polypeptide, and other protein by inserting DNA encoding the other protein into these DNAs.

In the vector of the second aspect, the above DNA encoding a polypeptide is not particularly limited as long as the amino acid sequence of the polypeptide satisfies the conditions described in the section of the fused protein of the second aspect. Specifically, DNA encoding a polypeptide having 557a.a-574a.a. of HIF-1α is, for example, DNA having the nucleotide sequence of SEQ ID NO: 2 or part thereof. DNA encoding a polypeptide having 548a.a.-603a.a. of HIF-1α is, for example, DNA having the nucleotide sequence of SEQ ID NO: 3 or part thereof.

In the vector of the second aspect, DNA encoding NLS is, for example, DNA having the nucleotide sequence of SEQ ID NO: 6 or part thereof as described in the section of the vector of the first aspect.

In the vector of the second aspect, the DNA encoding a protein having protein transduction activity through membrane is, for example, DNA encoding TAT.

DNA encoding TAT is not particularly limited as far as DNA has activity for transducing a protein through cell membrane. Specifically, it is DNA encoding the amino acid sequence of SEQ ID NO: 4 or DNA for the encoding the amino acid sequence consisting of amino acids Nos. 3 to 11 in the amino acid sequence of SEQ ID NO: 4. More specifically, it is DNA having the nucleotide sequence of SEQ ID NO: 5 or part thereof.

Still another example of the vector of the second aspect of the present invention is a vector which comprises the above DNA encoding other protein and DNAs for encoding NLS, a protein having protein transduction activity through membrane and a polypeptide or comprises the above DNA encoding other protein and DNAs for encoding TAT and a polypeptide to express the fused protein of the second aspect. The fused protein of the second aspect comprises NLS, a protein having protein transduction activity through membrane, a polypeptide and other protein in this order from the N terminus. That is, in the vector of the second aspect, these DNAs for encoding a polypeptide and each type of proteins are connected to one another in such a manner that their frames are aligned with one another, and further an expression control sequence such as a promoter required for the expression of a gene is contained.

The promoter is, for example, an SV40 early promoter, lac promoter, or the like.

The cell into which the vector of the second aspect of the present invention is introduced is, for example, the cell of a microorganism. Examples of the microorganism include: bacteria such as *Escherichia coli*; yeast such as *Saccharomyces cerevisiae*; filamentous fungi such as *Aspergillus nidulans*; and the cultured cells of animals or plants.

*Escherichia coli* LMPG194/pBAD3-0 and LMPG194/pBAD557-574 described above respectively harboring the plasmids pBAD/3-0 and pBAD/557-574 has been transferred to international depositary at the above International Patent Organism Depositary of National Institute of Advanced Industrial Science and Technology which is an independent administrative institution Central 6, Higashi, Tsukuba, Ibaraki, 305-8566 Japan) as accession Nos. FERM BP-7809 and FERM BP-7810 on Nov. 26, 2001, respectively.

*Escherichia coli* LMPG194/pBAD3-0 and LMPG194/pBAD557-574 described above respectively harboring the plasmids pBAD/3-0 and pBAD/557-574 has been transferred to international depositary at the above International Patent Organism Depositary of National Institute of Advanced Industrial Science and Technology which is an independent administrative institution (Central 6, Higashi, Tsukuba, Ibaraki, 305-8566 Japan) as accession Nos. FERM BP-7809 and FERM BP-7810 on Nov. 26, 2001, respectively.

A description is subsequently given of the method of controlling the existence of a fused protein using the fused protein of the second aspect.

The controlling method comprises allowing the above fused protein of the second aspect to be transduced into the cell from the outside of the cell; and controlling the existence state of the fused protein of the second aspect according to oxygen conditions in the cell. When the fused protein of the second aspect is used, the protein can be introduced into the cell advantageously. The expression "introduced" means that the fused protein is transduced into the cell from the outside of the cell and also includes a case where the fused protein is discharged from the inside of a certain cell to the outside of the cell and is introduced into another cell.

The expression "controlling the existence state of the fused protein according to oxygen conditions" means that the fused protein of the second aspect is controlled to be existent more stably in the cell under hypoxic conditions than under aerobic conditions as described in the section of the fused protein of the first aspect.

When the existence state of the fused protein is monitored by using the method of controlling the existence state of the fused protein of the second aspect and a labeling protein as the other protein with the label as an index, a cell under hypoxic conditions can be detected as having already been described in the section of the method of controlling the existence state of the fused protein of the first aspect.

When the fused protein of the second aspect is made existent in a cell under hypoxic conditions by using the method of controlling the existence state of the fused protein and using a protein having cytotoxicity as the other protein, the growth of the cell under hypoxic conditions can be inhibited as having already been described in the section of the method of controlling the existence state of the fused protein of the first aspect.

BEST MODE FOR CARRYING OUT THE INVENTION

The following examples are given to illustrate the present invention in further detail.

[A: Material and Method]

<1> Construction of NLS/HIF-1α ODD Domain/lacZ Fused Gene Expression Plasmid

All the identified vectors were produced based on the pCH110 Eukaryotic Assay Vector plasmid (Amersham Pharmacia Biotech). The plasmid has a Simian virus 40 early promoter.

Figure 1:
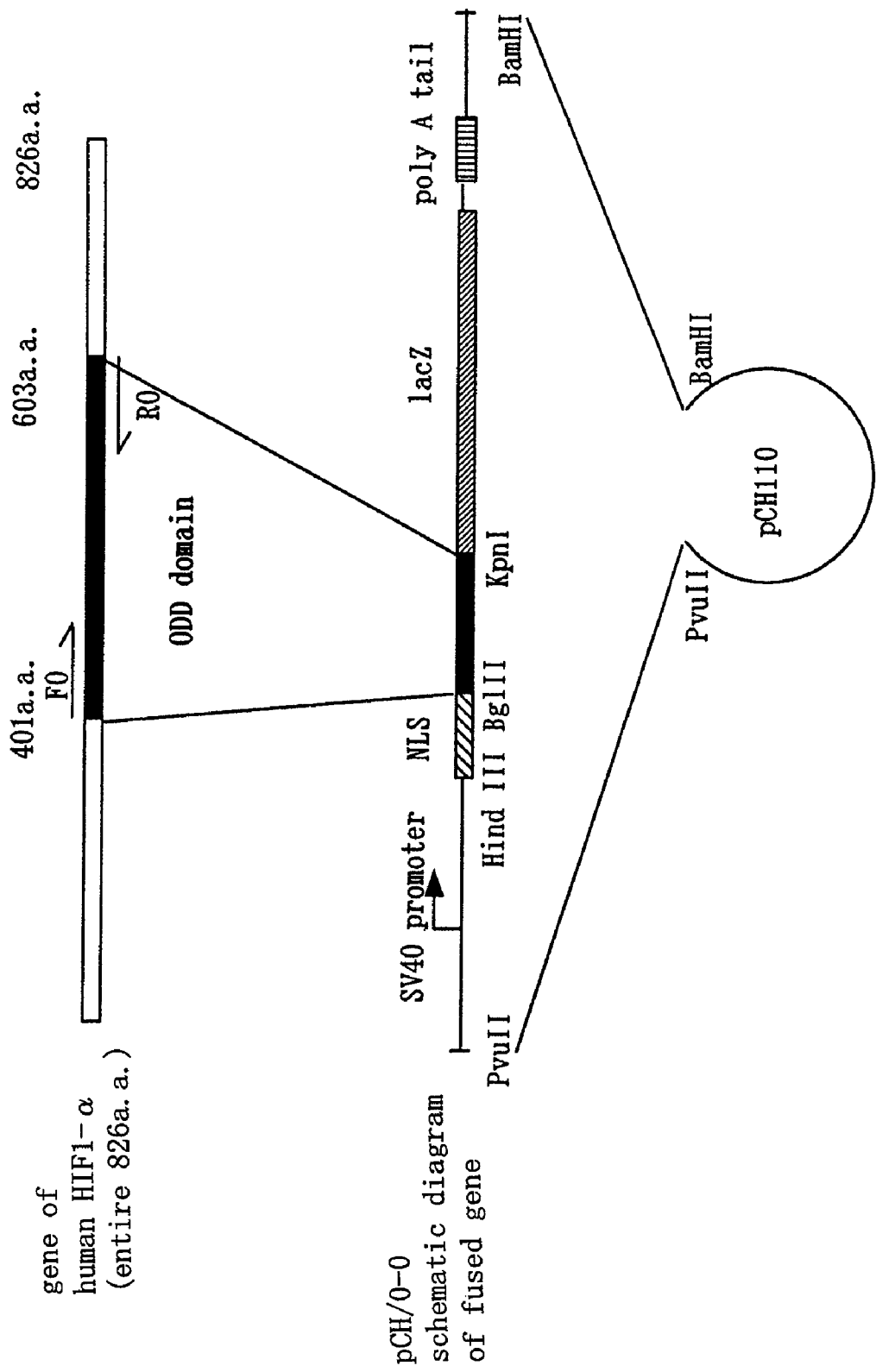
FIG. 1 is a schematic diagram of pCH/0-0 plasmid.
Figure 2:
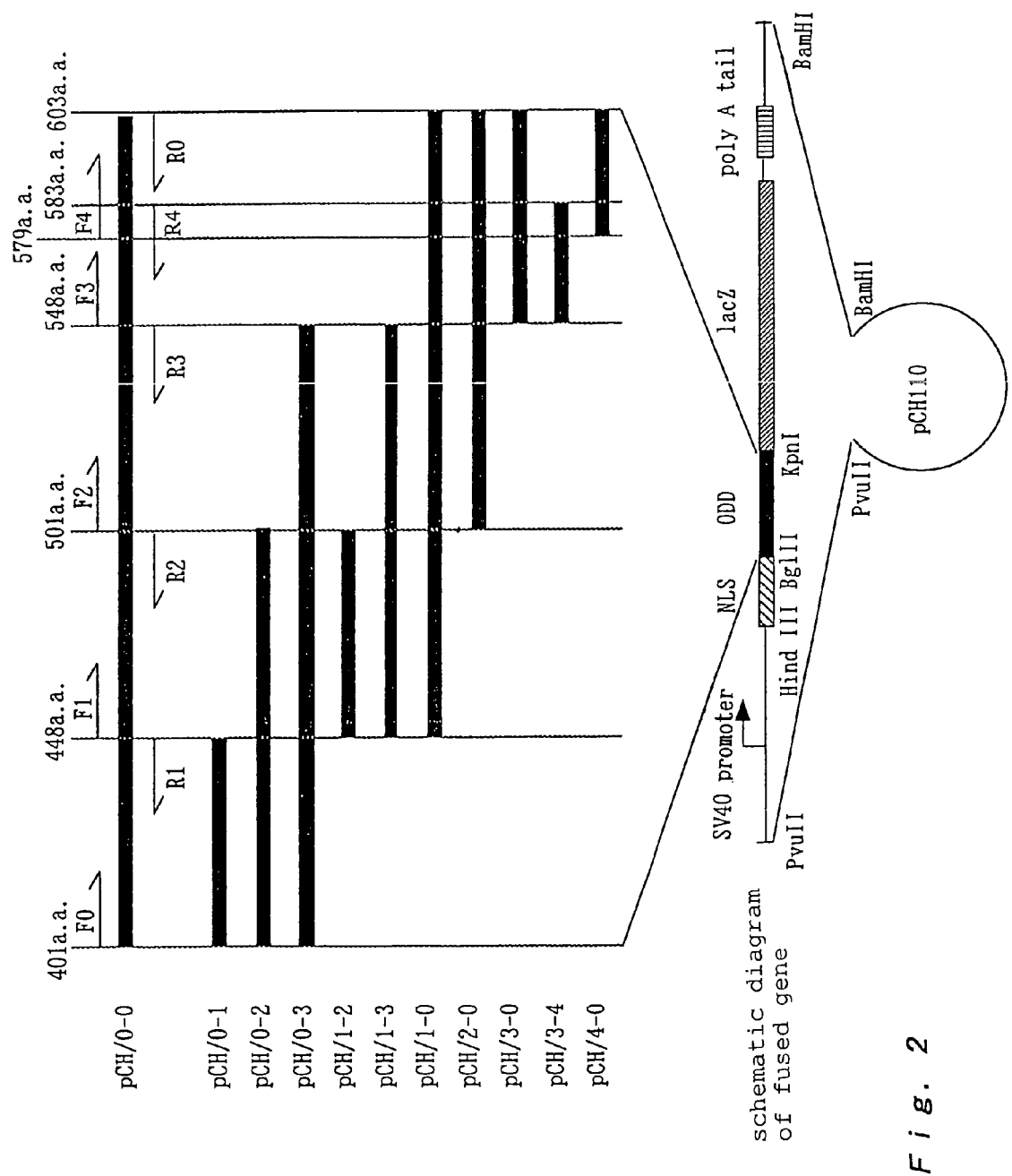
FIG. 2 is a schematic diagram of pCH/0-0 to pCH/4-0 plasmids.

(1) Plasmids: Construction of pCH/0-0, 0-1, 0-2, 0-3, 1-2, 1-3, 1-0, 2-0, 3-0, 3-4, and 4-0 (FIGS. 1 and 2)

DNA of Kozak sequence (nucleotide Nos. 8-14 of sequence of SEQ ID NO: 7) (Nucl. Acid Res. (1987) vol. 15, 20, 8125-8131: document 8) and DNA contained DNA encoding NLS (nuclear localization signal) (document 7) (nucleotide Nos. 17-37 of sequence of SEQ ID NO: 7) were first synthesized, annealed in each and treated with the HindIII and BglII restriction enzymes. Thereafter, the ODD domain (Oxygen Dependent Degradation domain) of human HIF-1α was amplified from human cDNA by PCR and treated with the BglII and KpnI restriction enzymes. The above DNA fragments were inserted between the HindIII site and KpnI site of pCH110/NLS by three-molecule ligation so that their translation frames were aligned with each other. The synthesized DNAs used for PCR are listed below.

1) Kozak ATG/NLS sense DNA (SEQ ID NO: 7) taagcttgacatggcgcctaagaagaagaggaagagatctg 2) Kozak ATG/NLS antisense DNA (SEQ ID NO: 8) cagatctcttcctcttcttcttaggcgccatgtcaagctta 3) ODD-BglII.FO primer (SEQ ID NO: 9) gagatctgccccagccgctggagacacaa 4) ODD-BglII.F1 primer (SEQ ID NO: 10) ggagatctttggcaatgtctccattacccacc 5) ODD-BglII.F2 primer (SEQ ID NO: 11) ggagatctcctagtccttccgatggaagcact 6) ODD-BglII.F3 primer (SEQ ID NO: 12) ggagatctaacccattttctactcaggacaca 7) ODD-BglII.F4 primer (SEQ ID NO: 13) ggagatctcagttgtcaccattagaaagcagt 8) ODD-KpnI.RO antisense primer (SEQ ID NO: 14) aggtacctgctggaatactgtaactgtgc 9) ODD-KpnI.R1 antisense primer (SEQ ID NO: 15) aaggtacctgatttatattctgtaattttttcgtt 10) ODD-KpnI.R2 antisense primer (SEQ ID NO: 16) aaggtacctgtgtctgatcctgaatctggggcat 11) ODD-KpnI.R3 antisense primer (SEQ ID NO: 17) aaggtacctgctttgcttctgtgtcttcagcaaa 12) ODD-KpnI.R4 antisense primer (SEQ ID NO: 18) aaggtacctgtaatggtgacaactgatcgaagga Combinations of primers used for amplification of the ODD domain inserted into the respective plasmids by PCR are listed below.

TABLE 1

| Plasmid | Sense primer | Anti-sense primer |
|---|---|---|
| pCH/0-0 | ODD-Bgl II.F0 | ODD-Kpn I.R0 |
| pCH/0-1 | ODD-Bgl II.F0 | ODD-Kpn I.R1 |
| pCH/0-2 | ODD-Bgl II.F0 | ODD-Kpn I.R2 |
| pCH/0-3 | ODD-Bgl II.F0 | ODD-Kpn I.R3 |
| pCH/1-2 | ODD-Bgl II.F1 | ODD-Kpn I.R2 |
| pCH/1-3 | ODD-Bgl II.F1 | ODD-Kpn I.R3 |
| pCH/1-0 | ODD-Bgl II.F1 | ODD-Kpn I.R0 |
| pCH/2-0 | ODD-Bgl II.F2 | ODD-Kpn I.R0 |
| pCH/3-0 | ODD-Bgl II.F3 | ODD-Kpn I.R0 |
| pCH/3-4 | ODD-Bgl II.F3 | ODD-Kpn I.R4 |
| pCH/4-0 | ODD-Bgl II.F4 | ODD-Kpn I.R0 |

Each plasmid was subjected to gene recombination so that the ODD domain shown in Table 2 was fused with NLS and lacZ gene at a protein level. "a.a." shows the position of the amino acid residue in the ODD domain. In Table 2, for example, pCH/0-0 means that a DNA strand encoding positions from 401 to 603 in the ODD domain was fused with a DNA strand for encoding NLS and lacZ gene.

TABLE 2

| Plasmid | Fused protein |
| --- | --- |
| pCH/0-0 | NLS/HIF-1α 401a.a.-603a.a./β-Gal |
| pCH/0-1 | NLS/HIF-1α 401a.a.-447a.a./β-Gal |
| pCH/0-2 | NLS/HIF-1α 401a.a.-500a.a./β-Gal |
| pCH/0-3 | NLS/HIF-1α 401a.a.-547a.a./β-Gal |
| pCH/1-2 | NLS/HIF-1α 448a.a.-501a.a./β-Gal |
| pCH/1-3 | NLS/HIF-1α 448a.a.-547a.a./β-Gal |
| pCH/1-0 | NLS/HIF-1α 448a.a.-603a.a./β-Gal |
| pCH/2-0 | NLS/HIF-1α 501a.a.-603a.a./β-Gal |
| pCH/3-0 | NLS/HIF-1α 548a.a.-603a.a./β-Gal |
| pCH/3-4 | NLS/HIF-1α 548a.a.-583a.a./β-Gal |
| pCH/4-0 | NLS/HIF-1α 579a.a.-603a.a./β-Gal |

In FIG. 1, FO and RO represent the positions of primers used for PCR. The bold line in FIG. 1 shows an ODD domain fused with the lacZ gene in each plasmid and the length of the domain. pCH/0-0 shows that a DNA strand encoding positions from 401 to 603 of the ODD domain and DNA strands encoding NLS and the lacZ gene were fused together. In FIG. 2, F0, F1, F2, F3, F4, R0, R1, R2, R3, and R4 indicate the positions of primers used for PCR, respectively.

Figure 3:
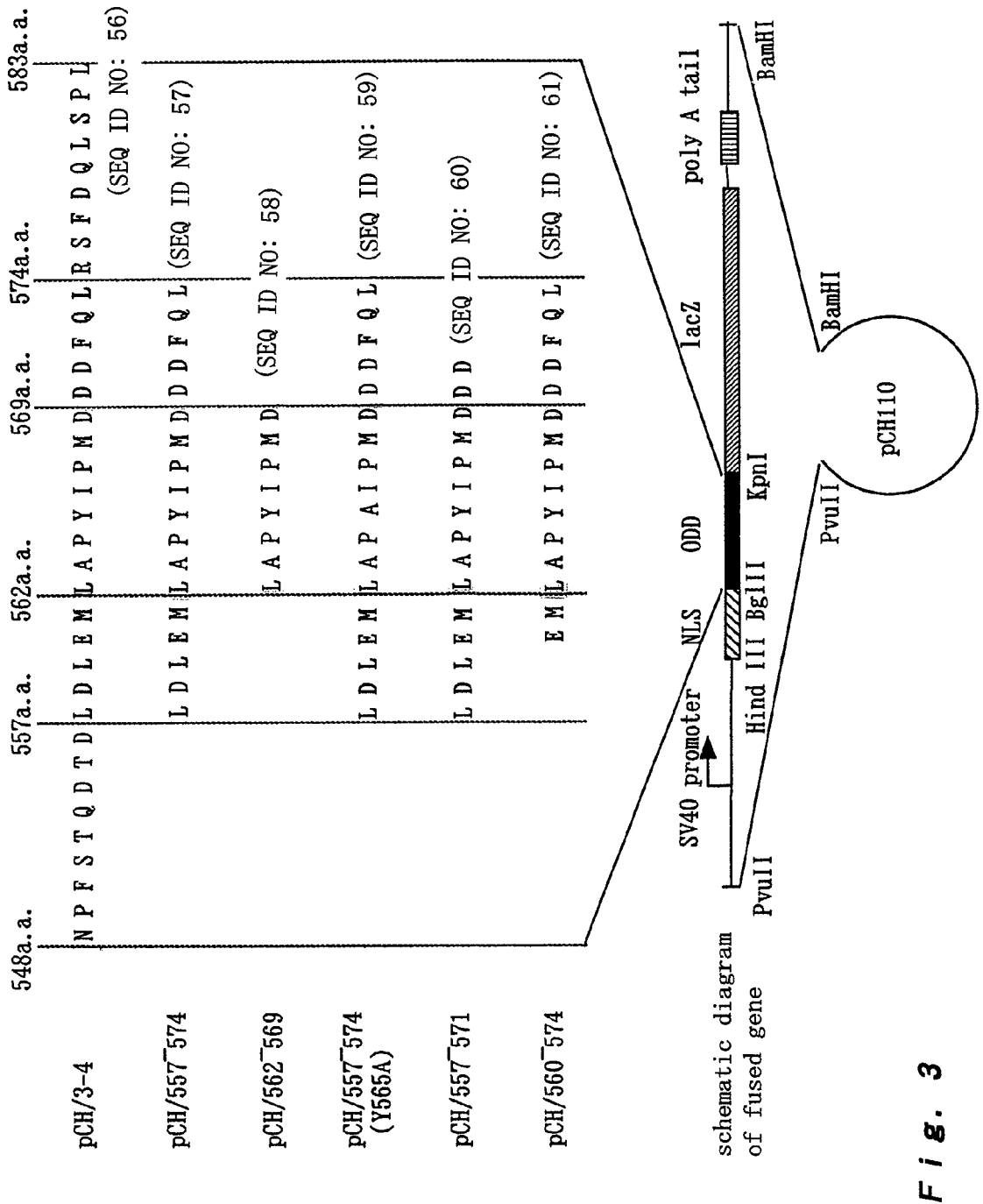
FIG. 3 is a schematic diagram of pCH series of plasmids.

(2) Construction of pCH/557-574, 562-569, 557-571, 560-574, 557-574 (Y565A), and 557-574 (ΔNLS) Plasmids (FIG. 3)

DNAs for encoding part of the ODD domain (Oxygen Dependent Degradation domain) of human HIF-1α (sequence Nos. 19-28) were first synthesized, annealed in each combination, and inserted between the BglII site and KpnI site of pCH110/3-0 so that their translation frames were aligned with one another. The synthesized DNAs used are listed below.

13) ODD 557-574 sense DNA (SEQ ID NO: 19) gatctttagacttggagatgttagctccctatatcccaatggatgatgacttccag ttacaggtac 14) ODD 557-574 antisense DNA (SEQ ID NO: 20) ctgtaactggaagtcatcatccattgggatatagggagctaacatctccaagtcta aa 15) ODD 562-569 sense DNA (SEQ ID NO: 21) gatctttagctccctatatcccaatggatcaggtac 16) ODD 562-569 antisense DNA (SEQ ID NO: 22) ctgatccattgggatatagggagctaaa 17) ODD 557-571 sense DNA (SEQ ID NO: 23) gatctttagacttggagatgttagctccctatatcccaatggatgatgaccaggta c 18) ODD 557-571 antisense DNA (SEQ ID NO: 24) ctggtcatcatccattgggatatagggagctaacatctccaagtctaaa 19) ODD 560-574 sense DNA (SEQ ID NO: 25) gatctgagatgttagctccctatatcccaatggatgatgacttccagttacaggta c 20) ODD 560-574 antisense DNA (SEQ ID NO: 26) ctgtaactggaagtcatcatccattgggatatagggagctaacatctca 21) ODD 557-574 Y565A sense DNA (SEQ ID NO: 27) gatctttagacttggagatgttagctcccgctatcccaatggatgatgacttccag ttacaggtac 22) ODD 557-574 Y565A antisense DNA (SEQ ID NO: 28) ctgtaactggaagtcatcatccattgggatagcgggagctaacatctccaagtcta aa Each plasmid was subjected to gene recombination so that the ODD domain shown in Table 3 was fused with NLS, and lacZ gene at a protein level.

TABLE 3

| Plasmid | Fused protein |
| --- | --- |
| pCH/557-574 | NLS/HIF-1α 557a.a.-574a.a./β-Gal |
| pCH/562-569 | NLS/HIF-1α 562a.a.-569a.a./β-Gal |
| pCH/557-571 | NLS/HIF-1α 557a.a.-571a.a./β-Gal |
| pCH/560-574 | NLS/HIF-1α 560a.a.-574a.a./β-Gal |
| pCH/557-574(Y565A) | NLS/HIF-1α 557a.a.-574a.a. (Y565A)/β-Gal |

In FIG. 3, "L", "D", and the like represent respective amino acid sequences in the ODD domain fused with the lacZ gene in each plasmid. For example, pCH/562-569 means that a DNA strand encoding "LAPYIPMD (SEQ ID NO: 29)" and a DNA strand encoding NLS and the lacZ gene were fused together.

Figure 4:
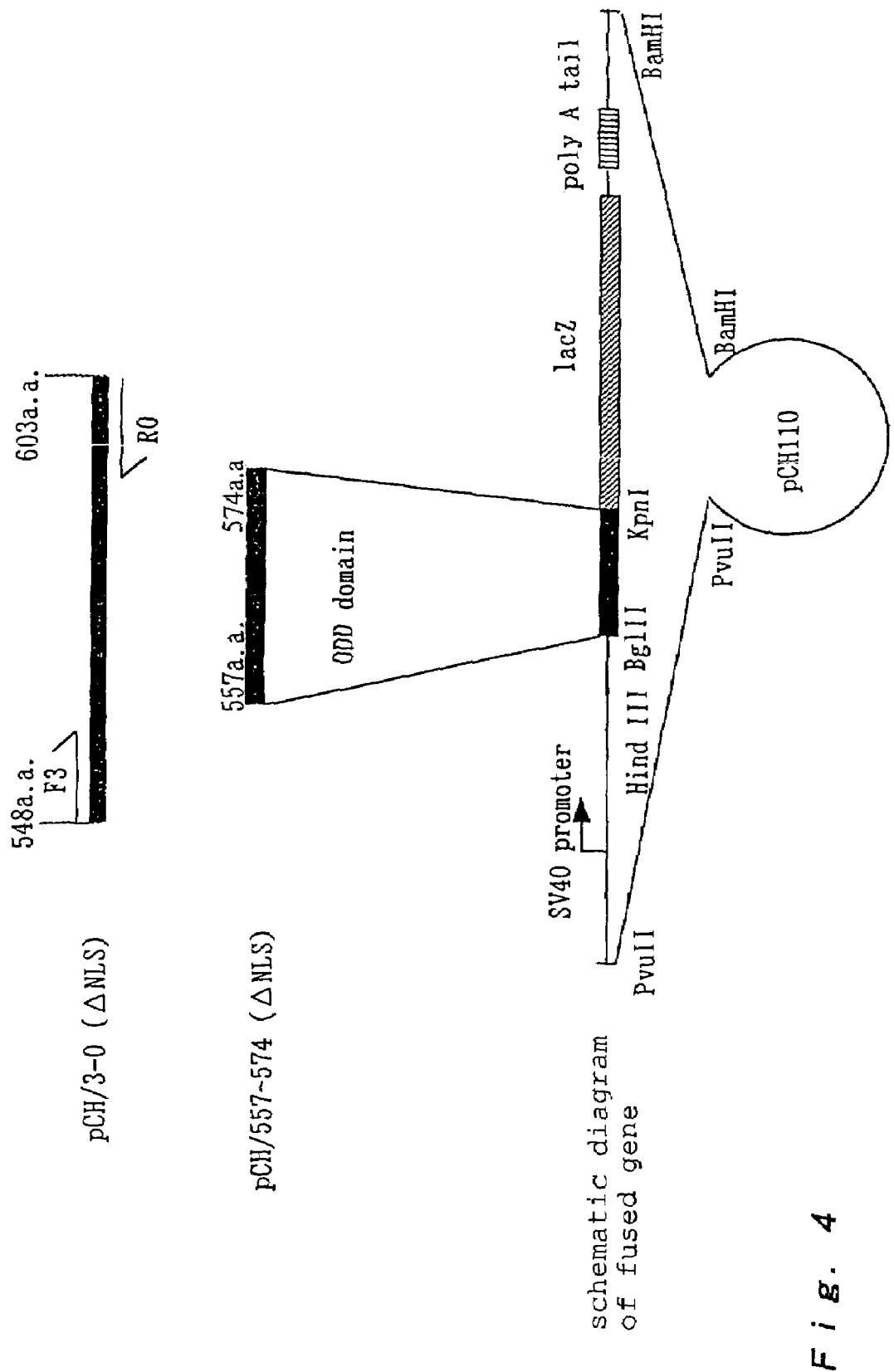
FIG. 4 is a schematic diagram of pCH/3-0 (ΔNLS) and pCH/557-574 (ΔNLS) plasmids.

(3) <1-3> Construction of pCH/557-574 (ΔNLS) and 3-0 (ΔNLS) Plasmids (FIG. 4)

pCH/557-574 (ΔNLS) and pCH/3-0 (ΔNLS) were produced based on pCH/557-574 and pCH/3-0, respectively. The HindIII-BglII region including the Kozak sequence and NLS (nuclear localization signal) was cut out from pCH/557-574 and pCH/3-0, the following DNAs for encoding only the Kozak ATG sequence were synthesized instead, and DNA fragments obtained by annealing the DNAs were inserted.

23) Kozak ATG sense DNA (SEQ ID NO: 30) agcttgacatggcga

24) Kozak ATG antisense DNA (SEQ ID NO: 31) gatctcgccatgtca

Each plasmid was subjected to gene recombination so that the ODD domain shown in Table 4 was fused with lacZ gene at a protein level.

TABLE 4

| Plasmid | Fused protein |
| --- | --- |
| pCH/557-574 (ΔNLS) | HIF-1α 557a.a.-574a.a./β-Gal |
| pCH/3-0 (ΔNLS) | HIF-1α 548a.a.-603a.a./β-Gal |

In FIG. 4, the bold line indicates the length of the ODD domain fused with the lacZ gene in each plasmid. For example, pCH/3-0 (ΔNLS) means that a DNA strand encoding the 548a.a.-603a.a. ODD domain and a DNA strand encoding the lacZ gene were fused together.

<2> Cell Culture

The HEK293 (derived from human embryo kidney) cells were cultured in a 5% $CO_2$ incubator at 37° C. using a Dubecco's MEM medium (GIBCO BRL) containing 5% of FCS, 100 U/ml of penicillin, and 100 µg/ml of streptomycin (of Meiji Pharmaceuticals) as an ordinary medium.

<3> DNA Transfection and X-Gal Staining $1 \times 10^5$ HEK293 cells (Graham F L, Smiley J, Russel W C, and Nairn R., J Gen Virol. 36(1): 59-74, 1977: document 10) were planted onto a 6-well plate, and 5 µg of a plasmid was introduced into the cells by a calcium phosphate transformation method (Chen, C. and H. Okayama., Mol. Cell. Biol. 7: 2745-2752, 1987: document 11) on the following day. After 24 hours of culture in a 3% $CO_2$ incubator at 37° C., the cells were removed from the dish by trypsin treatment, divided into two aliquots and plated onto a 6-well plate. To make a hypoxia-mimic condition for inhibiting a ubiquitin-proteasome system, in other words, for HIF-1α protein stability, 50 µM of Cbz-LLL (document 3) was added to one of the two aliquots and cultured for 24 hours. Thereafter, X-gal (5-bromo-4-chloro-3-indolyl-β-D-galactoside) staining (Sanes, J. R., J. L. Rubenstein and J. F. Nicolas. 1986. Use of a recombinant retrovirus to study post-implantation cell lineage in mouse embryos. EMBO J.5: 3133-3142: document 12) was carried out.

Example 1

1> Confirmation of Control of Cbz-LLL-Dependent Stability of Fused Protein of ODD Domain To study whether the stability of a protein fused with the ODD domain (401a.a.-603a.a. region) of the HIF-1α protein can be controlled depending on oxygen concentration, the pCH/0-0 plasmid (NLS/HIF-1α 401a.a.-603a.a./lacZ) was produced by fusing the ODD domain (401a.a.-603a.a.) with NLS and the lacZ gene ([A: Material and method] <1> (1)). Note that the NLS sequence was encoded for the wild type HIF-1α, so that pCH/0-0 was produced by fusing NLS with the ODD domain.

$1 \times 10^5$ HEK293 cells were planted onto a 6-well plate, and 5 μg of the pCH/0-0 plasmid was introduced into the cells by a calcium phosphate transformation method on the following day. After 24 hours of culture in a 3% $CO_2$ incubator at 37° C., the cells were divided into two aliquots by EDTA treatment. One was cultured in an ordinary medium, and the other was cultured in a medium containing 50 μM of Cbz-LLL, for 24 hours. Finally, X-gal staining was carried out to confirm the expression of a fused protein. The results are shown in Table 5.

As the result of X-gal staining, the number of cells stained blue and the density of the stained color were significantly reduced in the case of culture in the absence of Cbz-LLL as compared with culture in the presence of Cbz-LLL. In Table 5 (the same shall apply hereinafter), when there is a difference in the stability of the fused protein between the presence and absence of Cbz-LLL, that is, when it can be observed that the stability of the fused protein can be controlled depending on Cbz-LLL, a symbol + (plus) is given.

Meanwhile, when the pCH110 plasmid containing no ODD domain was introduced, there was seen no difference in the number of cells stained blue and the density of the stained color between the presence and absence of Cbz-LLL. In Table 5 (the same shall apply hereinafter), when no difference in the stability of a fused protein between the presence and absence of Cbz-LLL is observed, a symbol − (minus) is given.

TABLE 5

| Plasmid | Control of Cbz-LLL dependent stability of fused protein |
|---|---|
| pCH110 | − |
| pCH/0-0 | + |

Since it is reported that Cbz-LLL does not affect transfer activity and the stability of mRNA, these results show that the stability of β-galactosidase (β-gal) protein can be controlled depending on Cbz-LLL by fusing the 401a.a.-603a.a. region of HIF-1α.

<2> Identification of Region Required for Control of Cbz-LLL Dependent Stability of Fused Protein of ODD Domain (1) To identify a region in the ODD domain indispensable for the control of Cbz-LLL dependent stability of a fused protein, the N terminus and/or C terminus of the ODD domain are/is systematically deleted, and a plasmid was produced by fusing NLS and the lacZ gene (refer to [A: Material and method] <1> (1)) and introduced into the HEK293 cells as in the above <1>, and the HEK293 cells were stained with X-gal. The results are shown in Table 6.

As a result, when pCH/0-1, 0-2, 0-3, 1-2, 1-3, and 4-0 were introduced, there was seen no difference in the number of cells stained blue and the density of the stained color between the presence and absence of Cbz-LLL. Meanwhile, when pCH/1-0, 2-0, 3-0, and 3-4 were introduced into cells to culture them in the absence of Cbz-LLL, the number of cells stained blue and the density of the stained color were significantly reduced as compared with when they were cultured in the presence of Cbz-LLL.

TABLE 6

| Plasmid | Control of Cbz-LLL dependent stability of fused protein |
|---|---|
| pCH/0-1 | − |
| pCH/0-2 | − |
| pCH/0-3 | − |
| pCH/1-2 | − |
| pCH/1-3 | − |
| pCH/1-0 | + |
| pCH/2-0 | + |
| pCH/3-0 | + |
| pCH/3-4 | + |
| pCH/4-0 | − |

Figure 5:
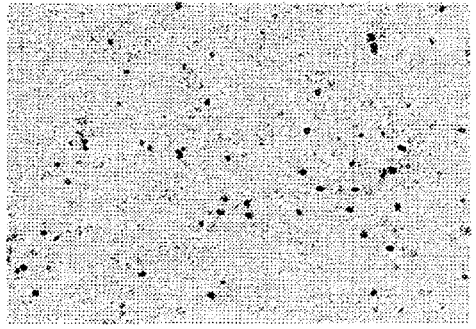
FIG. 5 shows photos showing the results of X-gal staining.
Figure 5:
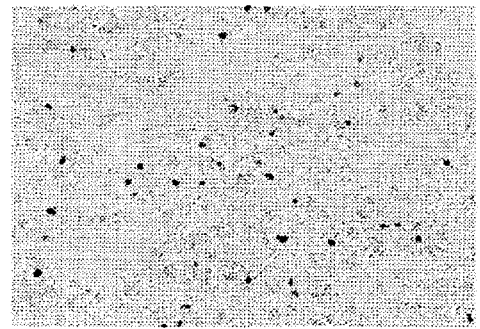
Figure 5:
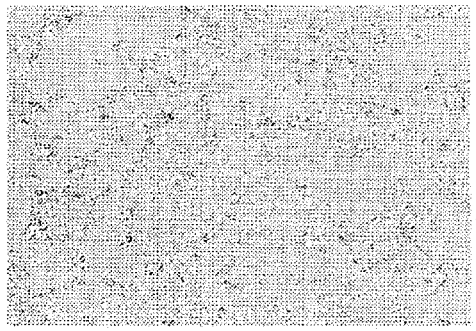
Figure 5:
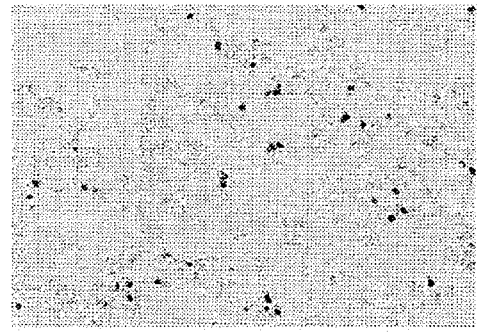

It was found from these results that the 548a.a.-583a.a. region of HIF-1α is important for the control of Cbz-LLL dependent stability of a fused protein. Note that the results of pCH/3-0 stained with X-gal are compared with those of pCH110 and shown in FIG. 5. In FIG. 5, A and B show HEK293 cells into which the pCH110 plasmid was introduced. On the other hand, C and D show HEK293 cells into which pCH/3-0 was introduced. Also, B and D show cells which were cultured in a medium containing Cbz-LLL, and A and C show cells which were cultured in a medium containing no Cbz-LLL.

(2) When known databases were searched for the homology of the 548a.a.-583a.a. region of the ODD domain of human HIF-1α, it was found that the region comprises a sequence (557a.a.-574a.a.) consisting of 18 amino acid residues kept in not only human HIF-1α but also the HIF-1α of a mouse. The pCH/557-574 plasmid was produced by fusing the 557a.a.-574a.a. region of HIF-1α with the lacZ gene (refer to [A: Material and method] <1> (2) and FIG. 3) and introduced into the HEK293 cells as in the above <2>, and the obtained cells were stained with X-gal.

TABLE 7

| Plasmid | Control of Cbz-LLL dependent stability of fused protein |
|---|---|
| pCH/3-4 | + |
| pCH/557-574 | + |

As a result, when pCH/557-574 was introduced into the cells and the cells were cultured in the absence of Cbz-LLL, the number of cells stained blue and the density of the stained color were significantly reduced as compared with when they were cultured in the presence of Cbz-LLL. This shows that the stability of β-gal protein is dependent on Cbz-LLL by fusing only the 557a.a.-574a.a. region.

(3) Subsequently, the pCH/562-569, 557-571, and 560-574 plasmids (562a.a.-569a.a., 557a.a.-571a.a., and 560a.a.-

574a.a. of HIF-1α were respectively fused with NLS and LacZ) having a shorter HIF-1α region to be fused with β-gal protein were produced (refer to [A: Material and method] <1> (2) and FIG. 3) and introduced into the HEK293 cells as in the above <2>, and the obtained cells were stained with X-gal. The results are shown in Table 8.

TABLE 8

| Plasmid | Control of Cbz-LLL dependent stability of fused protein |
|---|---|
| pCH/3-4 | + |
| pCH/557-574 | + |
| pCH/562-569 | − |
| pCH/557-571 | − |
| pCH/560-574 | − |

As a result, when these plasmids were introduced, there was seen no difference in the number of cells stained blue and the density of the stained color between the presence and absence of Cbz-LLL.

It was found from the above results that the 557a.a.-574a.a. region of HIF-1α must be fused to make the stability of β-gal protein significantly dependent on Cbz-LLL.

<3> Importance of 557a.a.-574a.a. Region of ODD Domain for Control of Cbz-LLL Dependent Stability of Tyrosine Residue It is known that the degradation of a protein by a ubiquitin/proteasome system is controlled by a change in the phosphorylation state of a target protein. Then it is conceived that the degradation of the produced fused protein by a ubiquitin system may be controlled by a change in the phosphorylation state. The pCH/557-574 (Y565A) plasmid was produced by substituting the tyrosine residue at the 565-position which is the only amino acid able to be phosphorylated in the HIF-1α 557a.a-574a.a. of the pCH/557-574 plasmid with the alanine residue (refer to [A: Material and method] <1> (2) and FIG. 3) and introduced into the HEK293 cells as described above, and the obtained cells were stained with X-gal. The results are shown in Table 9.

TABLE 9

| Plasmid | Control of Cbz-LLL dependent stability of fused protein |
|---|---|
| pCH/557-574 | + |
| pCH/557-574 (Y565A) | − |

As a result, when pCH/557-574 (Y565A) was introduced, there was seen no difference in the number of cells stained blue and the density of the stained color between the presence and absence of Cbz-LLL. It was thereby made clear that the tyrosine residue at the 565-position is an especially important amino acid for the stability of a protein fused with the 557a.a.-574a.a. of HIF-1α.

Example 2

To check whether NLS (nuclear localization signal) is required for the control of the Cbz-LLL dependent stabilities of a series of fused proteins, the pCH/557-574 (ΔNLS) and pCH/3-0 (ΔNLS) plasmids were produced by deleting NLS from pCH/557-574 and pCH/3-0, respectively (refer to [A: Material and method] <1> (3) and FIG. 4) and introduced into the HEK293 cells as in Example 1, and the obtained cells were stained with X-gal. The results are shown in Table 10.

TABLE 10

| Plasmid | Control of Cbz-LLL dependent stability Of fused protein |
|---|---|
| pCH3-0 (ΔNLS) | − |
| pCH/557-574(ΔNLS) | − |

As a result, there was seen no difference in the number of cells stained blue and the density of the stained color between the presence and absence of Cbz-LLL. It was thereby confirmed that NLS takes part in the control of Cbz-LLL dependent stability of a fused protein.

[B: Material and Method]

A general operation used in Example 3 et seq. will be described hereinbelow.

The annealing of the synthesized oligonucleotides was carried out as follows. 10 μl of a synthesized single-stranded oligonucleotide (concentration of 100 μl) was mixed with 10 μl of another synthesized oligonucleotide which is complementary to the above oligonucleotide, and 20 μl of a NaCl solution (1 M) and 160 μl of purified water were added to the mixture to prepare 200 μl of a reaction solution in total. This solution was heated at 95° C. for 1 minute, kept at 75° C. for 1 minute, and gradually cooled to 37° C. at a rate of 1° C./2 minutes. Then, 10 μl of a sodium acetate solution (3 M) and 250 μl of ethanol were added to 100 μl of the DNA solution, and the resultant mixture was centrifuged at 12 krpm for 10 minutes (4° C.). Thereafter, the supernatant was discarded, the precipitate was washed with 70% ethanol, and the 70% ethanol was removed in the end to obtain purified DNA.

As for a treatment with a restriction enzyme, 1 μg of plasmid DNA purified by ethanol precipitation was dissolved in 10 μl of a universal buffer (TAKARA Biomedical) and 90 μl of purified water, and a target restriction enzyme was added to the solution and maintained at 37° C. for 30 minutes after pipetting.

The separation (excision) of a DNA fragment was carried out as follows. To isolate the target DNA fragment which was treated with the restriction enzyme from other DNA fragments, agarose gel (containing EtBr) electrophoresis was first carried out. This agarose gel was exposed to light from a UV lamp having a wavelength of 365 nm to visualize the DNA fragment and the agarose gel containing the target DNA fragment was cut out with a razor. Finally, the target DNA fragment was extracted from this agarose gel using the QIAquick gel extraction kit (Qiagen) and purified.

Ligation was carried out in vitro using the DNA ligation kit Ver. 2 (TAKARA Biomedical) following the procedure of this kit for the phosphodiester binding of a plurality of DNA fragments. The amounts of the vector DNA fragment and the DNA fragment to be inserted used in ligation were both 10 ng.

Example 3

Construction of Plasmid for Expressing ODD Domain, 6 His Residues, NLS, TAT and lacZ Fused Gene <1> Construction of Plasmid Containing NLS, HIF-1 ODD Domain and lacZ Fused Gene The construction of the pCH/3-0 plasmid and the pCH/557-574 plasmid was carried out in accordance with the method described in [A: Material and method] <1> (1) and (2) (See also Tables 2 and 3 and FIGS. 1 to 3).

<2> Construction of Plasmid for Expressing His/NLS/TAT/HIF-1α ODD Domain/lacZ Fused Gene The above identified vectors were produced based on the pBAD plasmid/His/lacZ Vector (Invitrogen).

(1) Construction of pCH/TAT/3-0 and pCH/TAT/557-574 Plasmids

DNA fragments obtained by annealing the following synthetic oligo-DNAs (sequence Nos. 32 and 33) for encoding a TAT sequence were integrated into a vector obtained by treating pCH/3-0 or pCH/557-574 with the BglII restriction enzyme to obtain pCH/TAT/3-0 and pCH/TAT/557-574.

25) TAT.BglII sense DNA (SEQ ID NO: 32) gat cat atg gtc gta aga aac gtc gcc aac gtc gcc gaa 26) TAT.BglII antisense DNA (SEQ ID NO: 33) qat ctt cgg cga cgt tgg cga cgt ttc tta cga cca tat (2) Construction of pBAD/3-0 and pBAD/557-574 Plasmids The pBAD plasmid/His/lacZ Vector has two BamHI sites. After only the digestion site of the 413th nucleotide was cut off, the DNA end was made blunt. Subsequently, about 5,170 bp of a DNA fragment produced by digesting the vector with the SacI restriction enzyme was cut out by agarose gel electrophoresis and designated as pBAD/His/lacZ BamHI-SacI vector. Meanwhile, after pCH/TAT/3-0 and pCH/TAT/557-574 were digested with the HindIII restriction enzyme, their DNA ends were made blunt. About 2,250 bps of a DNA fragment produced by treating with the SacI restriction enzyme was cut out by agarose gel electrophoresis. These DNA fragments were ligated with the pBAD/His/lacZ BamHI-SacI vector to obtain pBAD/3-0 and pBAD/557-574.

(3) Construction of pBAD/P.C. Plasmid

The pCH/3-0 was first treated with the HindIII and KpnI restriction enzymes to produce about 6,900 bps of a DNA fragment which was then cut out by agarose gel electrophoresis. The following synthetic DNA fragments (sequence Nos. 34 and 35) for encoding Kozak ATG and NLS were annealed and inserted into the above DNA fragment to obtain pCH/P.C.

27) Kozak ATG/NLS HindIII sense DNA (SEQ ID NO: 34) agc ttg aca tgg cgc cta aga aga aga gga agc agg tac 28) Kozak ATG/NLS KpnI antisense DNA (SEQ ID NO: 35) ctg ctt cct ctt ctt ctt agg cgc cat gtc a Thereafter, the following synthetic oligo-DNA fragments (sequence Nos. 36 and 37) for encoding a TAT sequence were annealed and integrated into a vector obtained by treating pCH/P.C. with the KpnI restriction enzyme to produce pCH/TAT/P.C.

29) TAT.KpnI sense DNA (SEQ ID NO: 36) gat atg gtc gta aga aac gtc gcc aac gtc gcc gac agg tac 30) TAT KpnI antisense DNA (SEQ ID NO: 37) ctg tcg gcg acg ttg gcg acg ttt ctt acg acc ata tcg tac Subsequently, after pCH/TAT/P.C. was digested with the HindIII restriction enzyme, its DNA end was made blunt. About 2,000 bps of a DNA fragment produced by treating with the SacI restriction enzyme was cut out by agarose gel electrophoresis. This was ligated with the pBAD/His/lacZ BamHI-SacI vector to obtain pBAD/P.C.

(4) Explanation of Each Plasmid

In pBAD/P.C., pBAD/3-0 and pBAD/557-574, the ODD domain shown in Table 11 below, six His residues, TAT, NLS, and lacZ genes are fused at a protein level (see FIG. 6).

Note that in Table 11, "a.a." shows the position of the amino acid residue in the ODD domain. In Table 11, for example, pAD/3-D shows that a DNA strand encoding positions from 548 to 603 of the ODD domain and DNA strands for encoding His, NLS, TAT, and lacZ gene were fused together.

Figure 6:
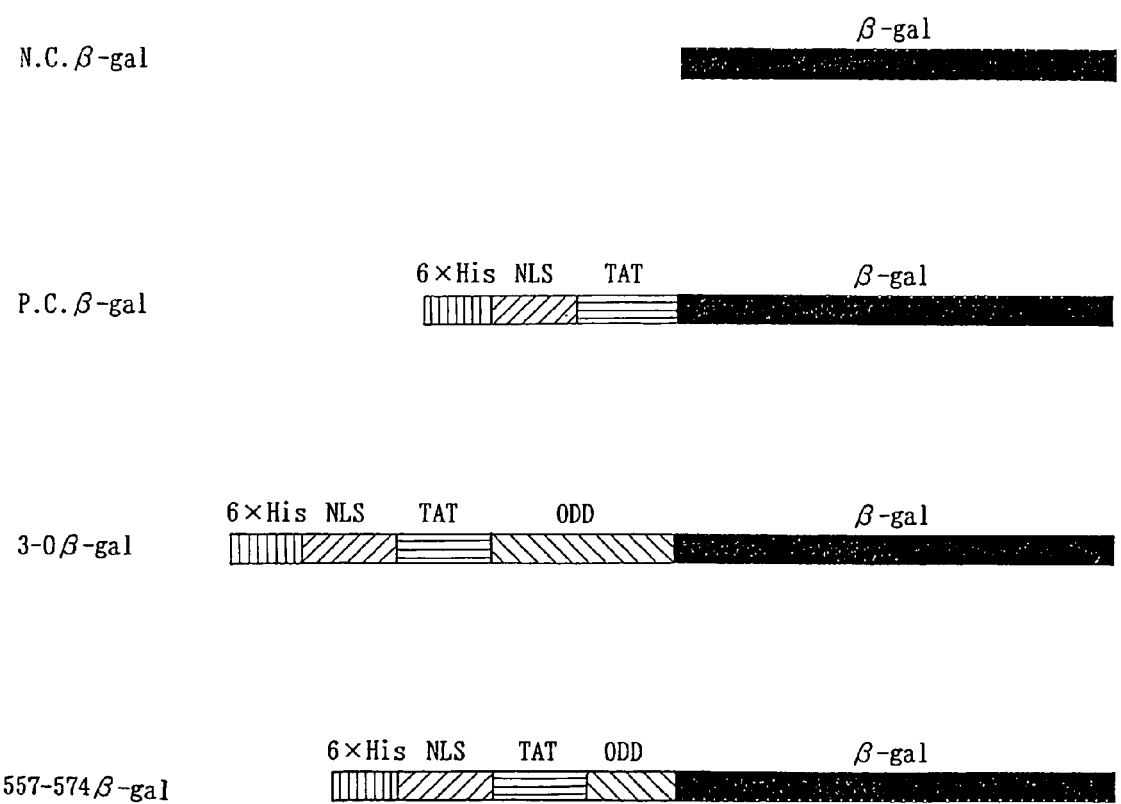
FIG. 6 is a schematic diagram of the structure of each fused protein.

Also, FIG. 6 is a schematic diagram of the structure of each fused protein. In the present invention, a plasmid for expressing each fused protein was produced to have an active region as shown in FIG. 6.

In FIG. 6, "6×His" denotes a region having six continuous histidine residues, "NLS" a nuclear localization signal derived from SV 40 large T antigen, "TAT" a TAT signal sequence derived from HIV (Cell; 55, 1179 (1988), Proc. Natl. Acad. Sci. USA; 91, 664 (1994)), "ODD" an Oxygen Dependent Degradation domain derived from a human HIF-1α gene, and "β-gal" an E. coli lacZ gene product. N.C.β-gal was a wild β-gal protein. The oxygen dependent degradation domains derived from a human HIF-1α gene and fused with 3-0 β-gal and 557-574 β-gal are HIF-1α548a.a.-603a.a. and HIF-1α557a.a.-574a.a., respectively.

TABLE 11

| Plasmid | Fused protein |
|---|---|
| pBAD/P.C. | 6xHis/NLS/TAT/β-Gal |
| pBAD/3-0 | 6xHis/NLS/TAT/HIF-1α548a.a.-603a.a./β-Gal |
| pBAD/557-574 | 6xHis/NLS/TAT/HIF-1α557a.a.-574a.a./β-Gal |

All the nucleotide sequences of the respective plasmids are shown in Table 12.

TABLE 12

| Plasmid | SEQ ID NO: |
|---|---|
| pCH/TAT/3-0 | 38 |
| pCH/TAT/557-574 | 40 |
| pBAD/3-0 | 42 |
| pBAD/557-574 | 44 |
| pCH/P.C. | 46 |
| pCH/TAT/P.C. | 48 |
| pBAD/P.C. | 50 |

Also, amino acid sequences to be encoded by genes in the respective plasmids are shown in Table 13.

TABLE 13

| Plasmid | SEQ ID NOS: |
|---|---|
| pCH/TAT/3-0 | 39 |
| pCH/TAT/557-574 | 41 |
| pBAD/3-0 | 43 |
| pBAD/557-574 | 45 |
| pCH/P.C. | 47 |
| pCH/TAT/P.C. | 49 |
| pBAD/P.C. | 51 |

Example 4

Confirmation of Cbz-LLL Dependent Stability of Fused Protein

<1> Purification of Fused Protein

The E. coli LMG194 strain was transformed by using three expression vectors, a) pBAD/P.C., b) pBAD/3-0 and c) pBAD/557-574. On the following day, a single colony was picked up from each of these culture plates, planted to 10 ml of a TB medium (containing 50 µg/ml of ampicillin), and cultured with shaking at 37° C. On the next day, 1 ml of each overnight culture was added to 200 ml of a TB medium (containing 50 μg/ml of ampicillin) and cultured with shaking at 37° C. When the absorbance $OD_{600}$ of each culture liquid reached 0.5, 0.4 g of L-(+)-arabinose was added to each culture liquid to induce the expression of a fused protein, and culture was continued until the following day.

The rough purification of the fused protein was next carried out in accordance with an attached protocol using Ni-NTA agarose (QIAGEN). To further improve the purification of the roughly purified fused protein, also enhance the concentration of the fused protein, and further substitute a buffer solution to PBS, MICROCON YM-100 (AMICON) was used in accordance with the attached protocol.

<2>

In the following operation, the A549 cell (derived from human lung cancer) was cultured in a 5% $CO_2$ incubator at 37° C. using a Dulbecco's MEM medium (GIBCO BRL) containing 5% of FCS, 100 U/ml of penicillin, and 100 μg/ml of streptomycin (Meiji Pharmaceuticals) as an ordinary medium.

$1×10^4$ A549 cells were scattered over a 24-hole multiwell dish, and each well was cleaned with serum-free D-MEM twice on the following day. A fused protein shown in Table 14 below was added to this and cultured in a 5% $CO_2$ incubator at 37° C. for 30 minutes.

TABLE 14

| Well No. | Fused protein | Amount of protein | Amount of medium |
|---|---|---|---|
| 1, 2 | N.C. protein (※1) | 0.2 U | 0.2 ml |
| 3, 4 | P.C. protein | 0.2 U | 0.2 ml |
| 5, 6 | 3-0 protein | 0.2 U | 0.2 ml |
| 7, 8 | 557-574 protein | 0.2 U | 0.2 ml |

Note that in Table 14, ※1 means that a wild β-gal protein was used as N.C. protein. Also, "U" represents the amount of a protein required for 1 μM of ONPG (o-nitrophenyl-b-D-lactopyranoside) to be degraded to o-nitrophenol and galactose at 37° C. and a pH of 7.5 in 1 minute.

Then, after the respective wells were cleaned with serum-free D-MEM twice again, well Nos. 1, 3, 5, and 7 were cultured in an ordinary medium and well Nos. 2; 4, 6, and 8 were cultured in a medium containing 50 μM of Cbz-LLL (document 3) for 20 hours as in a cell under hypoxic conditions to inhibit a ubiquitin-proteasome system. Thereafter, X-gal staining (document 12) was carried out.

As a result, a blue stained cell was not observed among the A549 cells to which the N.C. protein was added regardless of the existence of Cbz-LLL. On the other hand, all the A549 cells to which the P.C. protein was added were stained blue regardless of the existence of Cbz-LLL (see FIGS. 7A and B). This shows that the fused protein was introduced into the cell by the activity of the TAT region derived from HIV and fused with the added protein.

When Cbz-LLL was added to the A549 cells to which the 3-0 protein was added, a cell stained significantly strong was seen among them (see FIGS. 7C and D). This indicates that the stability of the fused protein is increased in the presence of Cbz-LLL by the activity of the ODD domain (548a.a.-603a.a. of HIF-1α) fused with the 3-0 protein. Even when the same experiments were conducted by adding the 557-574 protein, the same results as those obtained with the 3-0 protein could be obtained.

Figure 7:
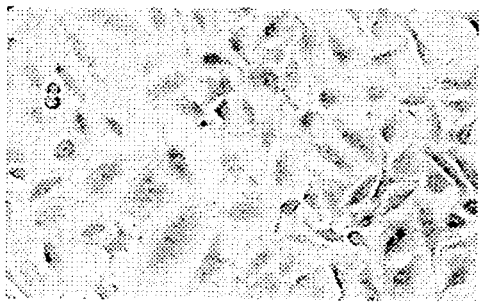
FIG. 7 shows photos showing the results of X-gal staining.
Figure 7:
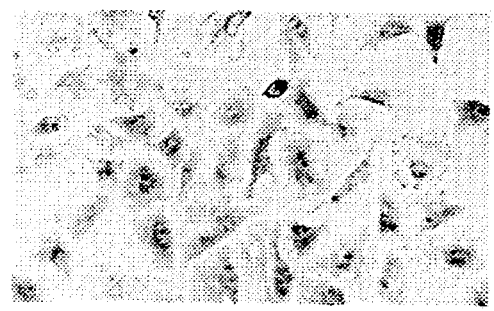
Figure 7:
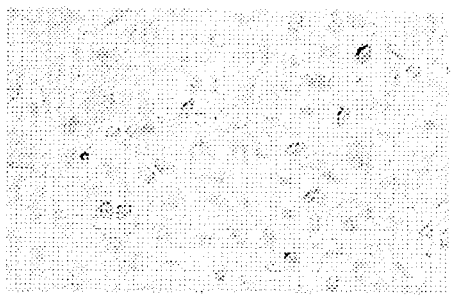
Figure 7:
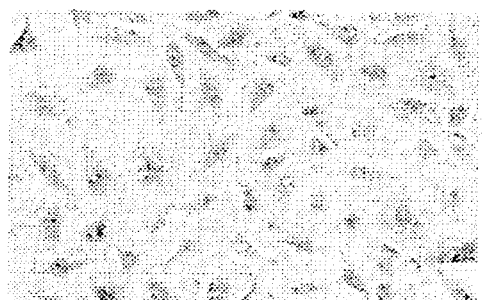

Note that in FIG. 7, A and B show cells into which P.C. β-gal was introduced, and C and D show cells to which 3-0 β-gal was added. Also, A and C show cells which were cultured in a medium containing no Cbz-LLL, and B and D show cells which were cultured in a medium containing Cbz-LLL.

Example 5

Confirmation of Oxygen Concentration Dependent Stability of Fused Protein

X-gal staining was carried out in the same manner as in Example 4 except that the method of forming hypoxic conditions was changed as follows.

The fused protein was added and then removed after 30 minutes. Thereafter, 20% $O_2$ gas was supplied to the medium to obtain aerobic conditions, 1% $O_2$ gas was supplied to the medium to obtain hypoxic conditions, and culture was carried out for about 24 hours. Finally, X-gal staining was performed.

As a result, all the A549 cells to which the P.C. protein was added were stained blue regardless of the concentration of oxygen (see FIGS. 8A and B).

On the other hand, when 1% $O_2$ gas was supplied to obtain hypoxic conditions, a cell stained significantly strong was seen among the A549 cells to which the 3-0 protein was added (see FIGS. 8C and D).

Figure 8:
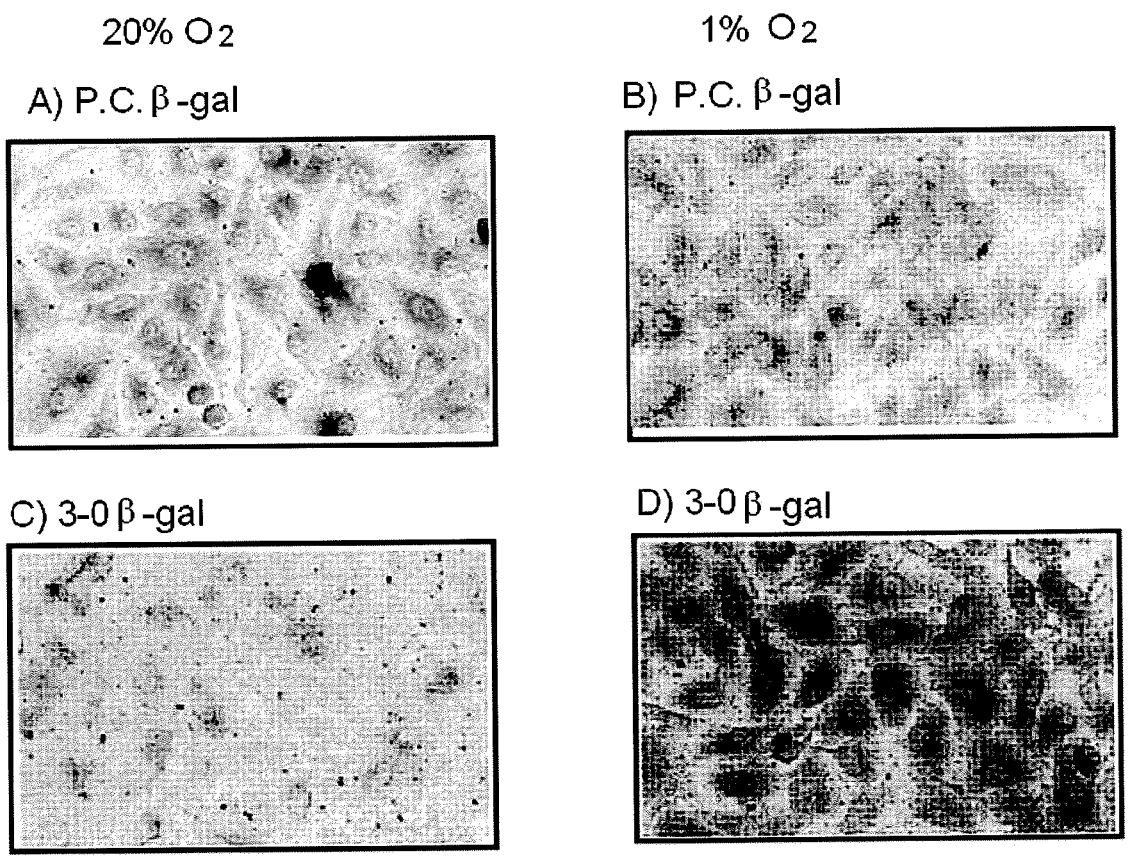
FIG. 8 shows photos showing the results of X-gal staining.

Note that in FIG. 8, A and B show cells to which P.C. β-gal was introduced, and C and D show cells to which 3-0 β-gal was added. Also, A and C show cells cultured in a medium to which 20% $O_2$ gas was supplied (aerobic condition), and B and D show cells cultured in a medium to which 1% $O_2$ gas was supplied (hypoxic condition).

Example 6

Confirmation of Oxygen Concentration Dependent Stability of Fused Protein

<1> Construction of TAT-ODD-Caspase 3 Fused Protein Expression Vector (pGEX/TAT-ODD3-0-Casp3)

PCR was first carried out using the following two synthetic oligo-DNAs and pBAD/3-0 as a template to amplify DNA encoded with a TAT signal sequence derived from HIV and oxygen derivative degradation domain (ODD) derived from the HIF-1α gene. This was treated with the BamHI and EcoRI restriction enzymes and then integrated between BamHI and EcoRI of the pGEX-6P-3 plasmid (Amersham Pharmacia Biotech) to produce pGEX/TAT-ODD.

31) TAT-sense-BamHI Primer (SEQ ID NO: 52) aggatcctatggtcgtaagaaacgt

32) ODD-anti-EcoRI primer (SEQ ID NO: 53) agaattcctggaatactgtaactgt

Meanwhile, PCR was carried out using the following two synthetic oligo-DNAs and cDNA of the A549 cell strain derived from a human lung cancer as a template to amplify a human derived Caspase-3 gene. The gene was treated with the EcoRI and SalI restriction enzymes and integrated between EcoRI and SalI of pGEX/TAT-ODD to produce the pGEX/TAT-ODD3-0-wt.Casp3 plasmid for expressing the GST-TAT-ODD-wt.Caspase3 protein having an N terminus fused with a GST tag.

33) Casp-sense-EcoRI primer (SEQ ID NO: 54) agaattcatggagaacactgaaaac

34) Casp-anti-SalI primer (SEQ ID NO: 55) agtcgacttagtgataaaaatagag

Further, the Caspase 3 mutant (hereinafter, referred to as mut. Caspase3) having no apoptosis derivation activity was produced in accordance with the document of Vocero-Akbani, A. M., Heyden, N. V., Lissy, N. A., Ratner, L. and Dowdy, S. F. Killing HIV-infected cells by transduction with an HIV protease-activated caspase-3 protein. Nat. Med. 5: 29-33, 1999. This structural gene was amplified by PCR using the Casp-sense-EcoRI primer and the Casp-anti-SalI primer, treated with the EcoRI and SalI restriction enzymes, and integrated between EcoRI and SalI of pGEX/TAT-ODD to produce pGEX/TAT-ODD3-0-mut.Casp3.

<2> Purification of TAT-ODD-wt./mut.Caspase3 Fused Protein

*E. coli* BL21 (DE3) pLysS competent cells (Novagen) were transformed by using pGEX/TAT-ODD3-0-wt.Casp3 and pGEX/TAT-ODD3-0-mut.Casp3. On the following day, a single colony was picked up from each of these culture plates, planted to 10 ml of a TB medium (containing 50 µg/ml of ampicillin) and cultured with shaking at 37° C.

On the next day, 1 ml of each overnight culture was added to 200 ml of a TB medium (containing 50 µg/ml of ampicillin) and further cultured with shaking at 37° C. When the absorbance $OD_{600}$ of each culture liquid reached 0.5, IPTG was added to each culture liquid to a final concentration of 0.5 M in order to induce the expression of a fused protein, and culture was continued until the following day.

The purification of each fused protein which was expressed in large quantities was carried out in accordance with the attached protocol using the Glutathione Sepharose 4B gel (Amersham Pharmacia Biotech) and PreScission Protease (Amersham Pharmacia Biotech).

3> Study on Oxygen Concentration Dependent Apoptosis Derivation Activity

In the following operation, the NIH3T3 mouse fetal cell strain was cultured in a 5% $CO_2$ incubator at 37° C. using a Dulbecco's MEM medium (GIBCO BRL) containing 10% of FCS, 100 U/ml of penicillin, and 100 µg/ml of streptomycin (Meiji Pharmaceuticals) as an ordinary medium.

$1 \times 10^5$ NIH3T3 cells were scattered over a 6-hole multiwell dish, Cbz-LLL was added to well Nos. 4, 5, and 6 to a final concentration of 50 µM, and the same amount of dimethyl sulfoxide (DMSO) as Cbz-LL added to the well Nos. 4, 5, and 6 was added to well Nos. 1, 2 and 3. On the following day, each well was cleaned with serum-free D-MEM twice. A fused protein shown in Table 15 below was added to each well. Further, well Nos. 1, 2, and 3 were cultured by supplying 20% of $O_2$ and well Nos. 4, 5, and 6 were cultured by supplying 1% of $O_2$ for 24 hours to observe the apoptosis derivation activity depending on oxygen concentration of each fused protein.

TABLE 15

| Well No. | Fused protein | Amount of protein |
|---|---|---|
| 1, 4 | Addition of only buffer | 0 µg/30 µl |
| 2, 5 | TAT-ODD-mut.Casp3 | 7.5 µg/30 µl |
| 3, 6 | TAT-ODD-Caspase3 | 7.5 µg/30 µl |

As a result, when TAT-ODD-wt.Caspase 3 fused protein was added and culture was carried out under hypoxic conditions, particularly strong apoptosis could be observed as shown in Table 16 (well No. 6) (indicated by +++ in Table 16). It is considered that a slight amount of apoptosis observed in well Nos. 4 and 5 was obtained by the derivation of the activity of genome-derived Caspase3 by Cbz-LLL.

TABLE 16

| Well No. | Added protein | Culture conditions | Apoptosis derivation activity |
|---|---|---|---|
| 1 | — | Aerobic | − |
| 2 | TAT-ODD-mut.Casp3 | Aerobic | − |
| 3 | TAT-ODD-wt.Casp3 | Aerobic | − |
| 4 | — | Hypoxic | + |
| 5 | TAT-ODD-mut.Casp3 | Hypoxic | + |
| 6 | TAT-ODD-wt.Casp3 | Hypoxic | +++ |

Figure 9:
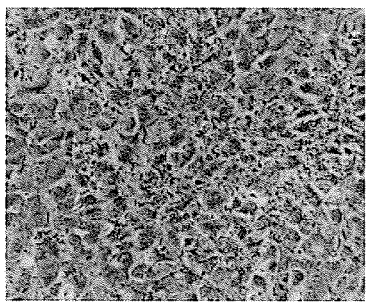
FIG. 9 shows photos showing observation of apoptosis dependent on an oxygen concentration in Example 6.
Figure 9:
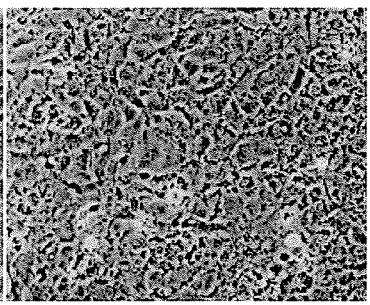
Figure 9:
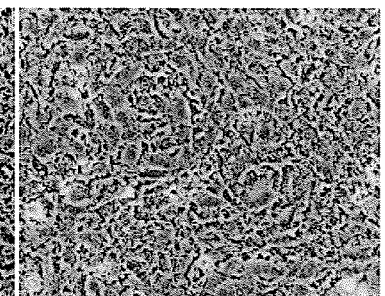
Figure 9:
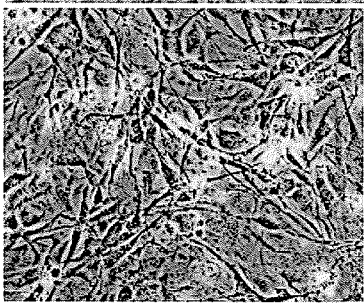
Figure 9:
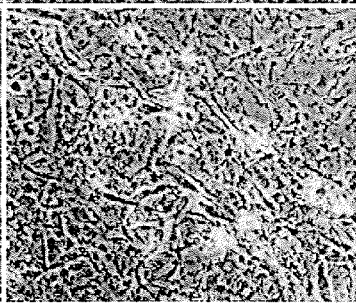
Figure 9:
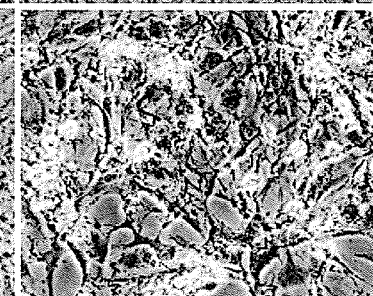

Further, the observation results of apoptosis in each well are shown in FIG. 9.

These results show that in a cell in which the TAT-ODD-Caspase3 fused protein is placed under aerobic conditions, fused protein is degraded while in a cell in which it is placed in hypoxic conditions, it is stabilized and activated to derive apoptosis.

INDUSTRIAL APPLICABILITY

The region which takes part in the stabilization of the HIF-1α protein can be identified by the present invention.

There can be provided a fused protein which comprises a protein having a region taking part in the stabilization of the specified HIF-1α protein and has stability dependent on oxygen conditions in a cell.

There can be also provided a fused protein which comprises a protein having a region taking part in the stabilization of the specified HIF-1α protein and has protein transduction activity through cell membrane and stability dependent on oxygen conditions in a cell.

Since the existence of a desired protein can be adjusted according to the amount of oxygen in a cell harboring a fused protein by the present invention, the present invention can be used for the detection of a cell under hypoxic conditions and the hindrance of the growth of a cell under hypoxic conditions.

What is claimed is:

1. An isolated polynucleotide encoding a polypeptide consisting of the amino acid sequence of SEQ ID NO: 1.

2. The polynucleotide of claim 1 consisting of SEQ ID NO: 2.

3. A method of controlling the presence of a protein in a cell harboring a gene of interest (GOI) encoding a protein of interest (POI), comprising:
   expressing the fused POI comprising a nuclear localization signal, a polypeptide (A) or (B), and a POI, when the GOI encoding the POI is inserted between a polynucleotide encoding the polypeptide (A) or (B), and the polynucleotide encoding the nuclear localization signal, wherein said polypeptide (A) or (B) is:
   (A) a polypeptide having the amino acid sequence of SEQ ID NO: 1; or
   (B) a polypeptide having an amino acid sequence comprising at least 16 contiguous amino acid residues in the amino acid sequence of SEQ ID NO: 1,
   wherein the polypeptide (B) imparts stability dependent on an oxygen concentration to the fused POI.

4. The method according to claim 3, wherein the fused POI is controlled such that it exists in a cell under hypoxic conditions and does not exist under aerobic conditions.

5. A fusion protein comprising:
   a polypeptide (A) or (B1);
   a polypeptide (C) or (D) having a TAT signal sequence (TAT) from HIV; and
   a protein of interest (POI), wherein the fusion protein has transduction activity through a cell membrane and stability dependent on an oxygen concentration in a cell, wherein polypeptide (A) or (B1) is:

(A) a polypeptide having the amino acid sequence of SEQ ID NO: 1;

(B1) a polypeptide consisting of whole or part of contiguous amino acid residues 24 to 79 of SEQ ID NO: 39, said polypeptide comprising an amino acid sequence consisting of at least 16 contiguous amino acid residues in the amino acid sequence of SEQ ID NO: 1, wherein said polypeptide imparts stability dependent on an oxygen concentration to said POI, when said POI is fused to a fusion protein comprising polypeptide (B1) and said polypeptide of TAT to form a fused POI;

and wherein (C) or (D) is:

(C) a polypeptide having the amino acid sequence of SEQ ID NO: 4; or (D) a polypeptide having an amino acid sequence comprising at least 9 contiguous amino acid residues in the amino acid sequence of SEQ ID NO: 4 and imparting protein transduction activity through a membrane to the fusion protein.

6. The fusion protein of claim 5, wherein said fusion protein exists more stably in a cell under hypoxic conditions than under aerobic conditions.

7. The fusion protein of claim 5, wherein said POI is a labeling protein or a cytotoxic protein.

8. A method of controlling the presence of a fusion protein in a cell, comprising:
transducing the fusion protein of claim 5 into a cell from outside of the cell; and
controlling the stability of the fusion protein according to an oxygen concentration in the transduced cell.

9. The method of claim 8, wherein the fusion protein is more stable in a cell under hypoxic conditions than under aerobic conditions.

10. A fusion protein comprising:
a nuclear localization signal;
a polypeptide having protein transduction activity through a cell membrane;
a protein of interest (POI); and
a polypeptide consisting of the amino acid sequence of SEQ ID NO: 1,
wherein the fusion protein has protein transduction activity through a cell membrane and stability dependent on an oxygen concentration in a cell.

11. The fusion protein of claim 10, wherein the polypeptide having protein transduction activity through a cell membrane is a TAT signal sequence from HIV, (C) or (D) and wherein (C) or (D) is:

(C) a polypeptide having the amino acid sequence of SEQ ID NO: 4;

(D) a polypeptide having an amino acid sequence comprising at least 9 contiguous amino acid residues in the amino acid sequence of SEQ ID NO: 4 and imparting protein transduction activity through a membrane to the fusion protein.

12. The fusion protein of claim 10, wherein said fusion protein exists more stably in a cell under hypoxic conditions than under aerobic conditions.

13. The fusion protein of claim 10, wherein said POI is a labeling protein or a cytotoxic protein.

14. A method of controlling the presence of a fusion protein in a cell, comprising:
transducing the fusion protein of claim 10 into a cell from outside of the cell; and
controlling stability of the fusion protein according to an oxygen concentration in the transduced cell.

15. The method of claim 14, wherein the fusion protein is more stable in a cell under hypoxic conditions than under aerobic conditions.

16. A vector comprising a polynucleotide encoding a polypeptide having the amino acid sequence of SEQ ID NO: 1 and further comprising, a polynucleotide encoding a nuclear localization signal, wherein the vector is capable of expressing a fusion protein comprising the nuclear localization signal, the polypeptide having the amino acid sequence of SEQ ID NO: 1, and a protein of interest (POI), wherein a gene of interest (GOI) encoding the POI is inserted between the polynucleotide encoding the polypeptide having the amino acid sequence of SEQ ID NO: 1, and the polynucleotide encoding the nuclear localization signal.

17. A cell comprising the vector of claim 16.

18. The cell of claim 17, wherein said cell is a microorganism.

19. The cell of claim 18, wherein said microorganism is *Escherichia coli*.

20. The vector of claim 16 wherein the GOI is operably fused to said polynucleotide encoding the polypeptide having the amino acid sequence of SEQ ID NO: 1, and the polynucleotide encoding the nuclear localization signal.

21. The vector of claim 20 wherein the fused POI is unstable under aerobic conditions.

22. The vector of claim 20, wherein the POI is a labeling protein or a cytotoxic protein.

23. A method of controlling an amount of a protein of interest (POI) in a cell, comprising:
introducing the vector of claim 20 into the cell;
subjecting the cell to more hypoxic or more aerobic conditions; and
expressing the fusion protein from the vector, wherein the amount of POI in the fusion protein is higher under the more hypoxic conditions than under the more aerobic conditions.

24. A method of inhibiting growth of a cell under hypoxic conditions, comprising:
introducing the vector of claim 20 into the cell, in which said POI is a cytotoxic protein; and
expressing the fused POI encoded by the vector in the cell under hypoxic conditions.

25. A method of detecting a cell which is under hypoxic conditions, comprising:
introducing the vector of claim 20 into a cell;
expressing the fusion protein from the vector; and
determining an amount of the POI in the fusion protein in the cell, wherein the amount of said POI determined being significantly greater than an amount observed under aerobic conditions indicates that the cell is under hypoxic conditions.

26. The method of claim 25, wherein the POI is a labeling protein.

27. A vector, which comprises:
a polynucleotide encoding a nuclear localization signal; and
a polynucleotide encoding a polypeptide (A) or (B);
wherein said polypeptide (A) or (B), comprises:

(A) a polypeptide having the amino acid sequence of SEQ ID NO: 1; or (B) a polypeptide consisting of whole or part of contiguous amino acid residues 24 to 79 of SEQ ID NO: 39, said polypeptide comprising an amino acid sequence consisting of at least 16 contiguous acid residues in the amino acid sequence of SEQ ID NO: 1, wherein said polypeptide (B) imparts stability dependent on an oxygen concentration to a polypeptide of interest (POI), when said POI is fused to a fusion protein comprising polypeptide (B) and said nuclear localization signal to form a fused POI, and wherein said vector is capable of expressing a fusion protein comprising the nuclear localization signal, the polypeptide (A) or (B), and a POI, when a gene of interest (GOI) encoding the POI is inserted between the polynucleotide encoding the nuclear localization signal, and the polynucleotide encoding the polypeptide (A) or (B).

28. The vector of claim 27, wherein the fusion protein exists more stably in a cell under hypoxic conditions than under aerobic conditions.

29. The vector of claim 27, wherein the polynucleotide encoding the polypeptide (A) or (B) has the nucleotide sequence consisting of whole or a part of contiguous nucleotides 71 to 246 of SEQ ID NO: 38, said polynucleotide encoding an amino acid sequence consisting of at least 16 contiguous amino acid residues in the amino acid sequence of SEQ ID NO: 1.

30. The vector of claim 27, wherein the polynucleotide encoding the polypeptide (C) or (D) has the nucleotide sequence of SEQ ID NO: 5 or part thereof, said polynucleotide encoding at least 9 contiguous amino acid residues in the amino acid sequence of SEQ ID NO: 4.

31. The vector of claim 27, which further comprises the GOI encoding a protein of interest (POI).

32. The vector of claim 31, wherein the POI is a labeling protein or a cytotoxic protein.

33. A method of inhibiting growth of a cell under hypoxic conditions, comprising:
introducing the vector of claim 31 into the cell in which said POI is a cytotoxic protein; and
expressing the fused POI encoded by the vector in the cell under hypoxic conditions.

34. A method of detecting a cell, which is under hypoxic conditions, comprising:
introducing the vector of claim 31 into a cell,
expressing the fusion protein from the vector, and
determining an amount of the POI in the fusion protein in the cell, wherein the amount of said POI determined being significantly greater than an amount observed under aerobic conditions indicates that the cell is under hypoxic conditions.

35. The method of claim 34, wherein the POI is a labeling protein.

36. The vector of claim 27, which further comprises a polypeptide having protein transduction activity through a membrane.

37. The vector of claim 36, wherein the polypeptide having protein transduction activity through a cell membrane is a TAT signal sequence from HIV comprising (C) or (D), and wherein (C) or (D) is:
(C) a polypeptide having the amino acid sequence of SEQ ID NO: 4; or
(D) a polypeptide having an amino acid sequence comprising at least 9 contiguous amino acid residues in the amino acid sequence of SEQ ID NO: 4 and imparting protein transduction activity through a membrane to the fusion protein.

38. The vector of claim 36, which further comprises a GOI encoding a protein of interest (POI).

39. The vector of claim 38, wherein the protein of interest (POI) is a labeling protein or a cytotoxic protein.

40. A method of detecting a cell, which is under hypoxic conditions, comprising:
introducing the vector of claim 38 into a cell,
expressing the fusion protein from the vector, and
determining an amount of the POI in the fusion protein in the cell, wherein the amount of said POI determined being significantly greater than an amount observed under aerobic conditions indicates that the cell is under hypoxic conditions.

41. The method of claim 40, wherein the POI is a labeling protein.

42. A vector which comprises:
a polynucleotide encoding a polypeptide (A) or (B1); and
a polynucleotide encoding a polypeptide (C) or (D) having a TAT signal sequence (TAT) from HIV,
wherein said polypeptide (A) or (B1) is:
(A) a polypeptide having the amino acid sequence of SEQ ID NO: 1; or
(B1) a polypeptide consisting of whole or part of contiguous amino acid residues 24 to 79 of SEQ ID NO: 39, said polypeptide comprising an amino acid sequence consisting of at least 16 contiguous amino acid residues in the amino acid sequence of SEQ ID NO: 1, wherein said polypeptide imparts stability dependent on an oxygen concentration to a protein of interest (POI) when said POI is fused to a fusion protein comprising polypeptide (A) or (B1) and said polypeptide TAT to form a fused POI,
and wherein (C) or (D) is:
(C) a polypeptide having the amino acid sequence of SEQ ID NO: 4; or
(D) a polypeptide having an amino acid sequence comprising at least 9 contiguous amino acid residues in the amino acid sequence of SEQ ID NO: 4 and imparting protein transduction activity through a membrane to the fusion protein and wherein said vector is capable of expressing a fusion protein comprising the polypeptide (C) or (D), the polypeptide (A) or (B1), and a POI when a gene of interest (GOI) encoding the POI is inserted between the polynucleotide encoding the polypeptide (C) or (D), and the polynucleotide encoding the polypeptide (A) or (B1).

43. The vector of claim 42, wherein the fusion protein exists more stably in a cell under hypoxic conditions than under aerobic conditions.

44. The vector of claim 42, wherein the polynucleotide encoding the polypeptide (A) or (B1) has the nucleotide sequence consisting of whole or a part of contiguous nucleotides 71 to 246 of SEQ ID NO: 38, said polynucleotide encoding an amino acid sequence consisting of at least 16 contiguous amino acid residues in the amino acid sequence of SEQ ID NO: 1.

45. The vector of claim 42, wherein the polynucleotide encoding the polypeptide (C) or (D) has the nucleotide sequence of SEQ ID NO: 5 or part thereof, said polynucleotide encoding at least 9 contiguous amino acid residues in the amino acid sequence of SEQ ID NO: 4.

46. The vector of claim 42, which further comprises the gene of interest (GOI) encoding a protein of interest (POI).

47. The vector of claim 46, wherein the protein of interest (POI) is a labeling protein or a cytotoxic protein.

* * * * *